(12) United States Patent
Kim et al.

(10) Patent No.: US 7,371,859 B2
(45) Date of Patent: May 13, 2008

(54) PNA MONOMER AND PRECURSOR

(75) Inventors: Sung Kee Kim, Daejeon (KR); Hyunil Lee, Daejeon (KR); Jong Chan Lim, Daejeon (KR); Hoon Choi, Daejeon (KR); Jae Hoon Jeon, Daejeon (KR); Sang Youl Ahn, Daejeon (KR); Sung Hee Lee, Suwon (KR); Won Jun Yoon, Seoul (KR)

(73) Assignee: Panagene, Inc., Daejeon (KR)

( * ) Notice: Subject to any disclaimer, the term of this patent is extended or adjusted under 35 U.S.C. 154(b) by 321 days.

(21) Appl. No.: 11/182,935

(22) Filed: Jul. 15, 2005

(65) Prior Publication Data

US 2006/0030709 A1   Feb. 9, 2006

(51) Int. Cl.
  C07D 405/14   (2006.01)
  C07D 407/14   (2006.01)
  C07D 409/14   (2006.01)
  C07D 417/14   (2006.01)
  C07D 239/54   (2006.01)
  C07D 241/18   (2006.01)
(52) U.S. Cl. ................... 544/310; 544/357; 544/309
(58) Field of Classification Search ............... 544/310, 544/357, 309
  See application file for complete search history.

(56) References Cited

U.S. PATENT DOCUMENTS

| | | | |
|---|---|---|---|
| 4,204,870 | A | 5/1980 | Chapman et al. |
| 5,539,083 | A | 7/1996 | Cook et al. |
| 6,063,569 | A | 5/2000 | Gildea et al. |
| 6,133,444 | A | 10/2000 | Coull et al. |
| 6,172,226 | B1 | 1/2001 | Coull et al. |
| 2003/0195332 | A1 | 10/2003 | Kim et al. |
| 2004/0102450 | A1 | 5/2004 | Ewing et al. |

FOREIGN PATENT DOCUMENTS

| | | |
|---|---|---|
| DE | 2135543 | 1/1973 |
| WO | WO 92/20702 | 11/1992 |
| WO | WO 00/02899 | 1/2000 |

OTHER PUBLICATIONS

Akaji et al., *Tetrahedron Lett.*, 33(22):3177-3180(1992).
Betts et al., *Science*, 270:1838-1841(1995).
Blankemeyer-Menge et al., *Tetrahedron Lett.*, 31(12):1701-1704(1990).
Breipohl et al., *Bioorg. Med. Chem. Lett.*, 6(6):665-670(1996).
Breipohl, et al., *Tetrahedron*, 53(43):14671-14686(1997).
Carpino, *J. Am. Chem. Soc.*, 115:4397-4398(1993).
Castro et al., *Tetrahedron Lett.*, 14:1219-1222(1975).
Christensen et al., *J. Pepi. Sci.*, 3:175-183(1995).
Coste et al., *Tetrahedron Lett.*, 31(2):205-208(1990).
Coste et al., *Tetrahedron Lett.*, 31(5)669-672(1990).
Coste et al., *Tetrahedron Lett.*, 32(17):1967-1970(1991).
Dourtoglou et al., *Synthesis*, 572-574(1984).
Dueholm et al., *J. Org. Chem.*, 59:5767-5773(1994).
Dueholm et al., *New J. Chem.*, 21:19-31(1997).
Egholm et al., *J. Am. Chem. Soc.*, 114:1895-1897(1992).
Egholm et al., *Nature*, 365:566-568(1993).
Egholm et al., *J. Chem. Soc. Chem. Commun.*, 800-801(1993).
Ehrlich et al., *Tetrahedron Lett.*, 34(30):4781-4784(1993).
Englisch et al., *Angew. Chem. Int. Ed. Engl.*, 30(6):613-629(1991).
Finn et al., *Nucleic Acid Research*, 24(17):3357-3363(1996).
Hyrup et al., *J. Am. Chem. Soc.*, 116:7964-7970(1994).
Kim et al., *J. Am. Chem. Soc.*, 115(15):6477-6481(1993).
Kirstgen et al., *J. Chem. Soc. Chem. Commun.*, 1870-1871(1987).
Knorr et al., *Tetrahedron Lett.*, 30(15):1927-1930(1989).
Knudsen et al., *Nucleic Acids Res.*, 24(3):494-500(1996).

(Continued)

*Primary Examiner*—Venkataraman Balasubramanian
(74) *Attorney, Agent, or Firm*—JHK Law; Joseph Hyosuk Kim

(57) ABSTRACT

This application relates to monomers of the general formula (I) for the preparation of PNA (peptide nucleic acid) oligomers and provides method for the synthesis of both predefined sequence PNA oligomers and random sequence PNA oligomers:

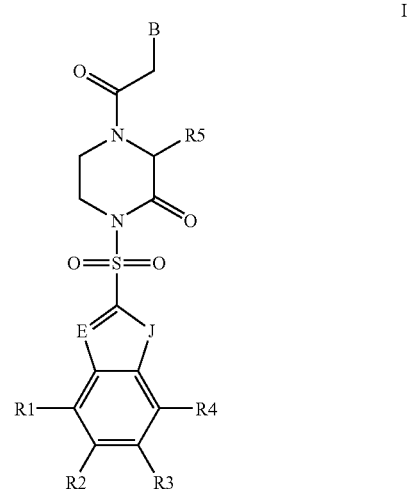

wherein
E is nitrogen or C—R'; J is sulfur or oxygen;
R', R1, R2, R3, R4 is independently H, halogen, alkyl, nitro, nitrile, alkoxy, halogenated alkyl, halogenated alkoxy, phenyl or halogenated phenyl,
R5 is H or protected or unprotected side chain of natural or unnatural α-amino acid; and
B is a natural or unnatural nucleobase, wherein when said nucleobase has an exocyclic amino function, said function is protected by protecting group which is labile to acids but stable to weak to medium bases in the presence of thiol.

13 Claims, 18 Drawing Sheets

OTHER PUBLICATIONS

Leijon et al., *Biochemistry*, 33:9820-9825(1994).
Mesmaeker et al., *Curr. Opinion Struct. Biol.*, 5:343-355(1995).
Nielsen, *Curr. Opin. Biotech.*, 12:16-20(2001).
Nielsen et al., *Science*, 254:1497-1500(1991).
Orum et al., *BioTechniques*, 19(3):472-480(1995).
Peyman et al., *Angew. Chem. Int. Ed. Engl.*, 35(22):2636-2638(1996).
Puschl et al., *Tetrahedron Lett.*, 39:4707-4710(1998).
Stetsenko et al., *Tetrahedron Lett.* 37(20):3571-3574(1996).
Thomson et al., *Tetrahedron*, 51(22):6197-6194(1995).
Tomac et al., *J. Am. Chem. Soc.*, 118:5544-5552(1996).
Uhlman et al., *Angew. Chem. Int. Ed. Engl.*, 35(22):2632-2635(1996).
Will et al., *Tetrahedron*, 51(44):12069-12082(1995).
Wittung et al., *J. Am. Chem. Soc.*, 118:7049-7054(1996).

X = F, Cl, Br, I

H₂N-CTCGTTTCCA-H

A

B

H₂N-TCGTGTCGTA-H

A

B

H₂N-ACCAGCGGCA-H

H₂N-TCTTCTAGTG-H

H₂N-GTGCTCCTCC-H

A B

H₂N-GTGCATGATG-H

A B

H₂N-CCCTACTGTG-H

A

B

H₂N-CTCATTTCCA-H

A

B

H₂N-ACCCTACTGT-H

A  B

SEQUENCE LISTING

```
<160> NUMBER OF SEQ ID NOS: 9

<210> SEQ ID NO 1
<211> LENGTH: 10
<212> TYPE: DNA
<213> ORGANISM: Artificial
<220> FEATURE:
<223> OTHER INFORMATION: PNA Oligomer

<400> SEQUENCE: 1
ctcgtttcca                                                            10

<210> SEQ ID NO 2
<211> LENGTH: 10
<212> TYPE: DNA
<213> ORGANISM: Artificial
<220> FEATURE:
<223> OTHER INFORMATION: PNA Oligomer

<400> SEQUENCE: 2
tcgtgtcgta                                                            10

<210> SEQ ID NO 3
<211> LENGTH: 10
<212> TYPE: DNA
<213> ORGANISM: Artificial
<220> FEATURE:
<223> OTHER INFORMATION: PNA Oligomer

<400> SEQUENCE: 3
accagcggca                                                            10

<210> SEQ ID NO 4
<211> LENGTH: 10
<212> TYPE: DNA
<213> ORGANISM: Artificial
<220> FEATURE:
<223> OTHER INFORMATION: PNA Oligomer
```

-continued

```
<400> SEQUENCE: 4
tcttctagtg                                                              10

<210> SEQ ID NO 5
<211> LENGTH: 10
<212> TYPE: DNA
<213> ORGANISM: Artificial
<220> FEATURE:
<223> OTHER INFORMATION: PNA Oligomer

<400> SEQUENCE: 5
gtgctcctcc                                                              10

<210> SEQ ID NO 6
<211> LENGTH: 10
<212> TYPE: DNA
<213> ORGANISM: Artificial
<220> FEATURE:
<223> OTHER INFORMATION: PNA Oligomer

<400> SEQUENCE: 6
gtgcatgatg                                                              10

<210> SEQ ID NO 7
<211> LENGTH: 10
<212> TYPE: DNA
<213> ORGANISM: Artificial
<220> FEATURE:
<223> OTHER INFORMATION: PNA Oligomer

<400> SEQUENCE: 7
ccctactgtg                                                              10

<210> SEQ ID NO 8
<211> LENGTH: 10
<212> TYPE: DNA
<213> ORGANISM: Artificial
<220> FEATURE:
<223> OTHER INFORMATION: PNA Oligomer

<400> SEQUENCE: 8
ctcatttcca                                                              10

<210> SEQ ID NO 9
<211> LENGTH: 10
<212> TYPE: DNA
<213> ORGANISM: Artificial
<220> FEATURE:
<223> OTHER INFORMATION: PNA Oligomer

<400> SEQUENCE: 9
accctactgt                                                              10
```

PNA MONOMER AND PRECURSOR

BACKGROUND OF THE INVENTION

1. Field of the Invention

The present invention relates to monomers suitable for the preparation of PNA oligomers. The present invention also relates to precursors to the monomers and methods of making the PNA monomers from the precursors. Further, the invention relates to methods of making PNA oligomers using the PNA monomers.

2. General Background and State of the Art

In the last two decades, attempts to optimize the properties of oligonucleotide by modification of the phosphate group, the ribose ring, or the nucleobase have resulted in a lot of discoveries of new oligonucleotide derivatives for the application in the fields of DNA diagnostics, therapeutics in the form of antisense and antigene, and the basic research of molecular biology and biotechnology (U. Englisch and D. H. Gauss, *Angew. Chem. Int. Ed. Engl.* 1991, 30, 613-629; A. D. Mesmaeker et al. *Curr. Opinion Struct. Biol.* 1995, 5, 343-355; P. E. Nielsen, *Curr. Opin. Biotechl.*, 2001, 12, 16-20.). The most remarkable discovery is peptide nucleic acid which was reported by the Danish group of Nielsen, Egholm, Buchardt, and Berg (P. E. Nielsen et al., *Science*, 1991, 254, 1497-1500). PNA is DNA analogue in which an N-(2-aminoethyl)glycine polyamide replaces the phosphate-ribose ring backbone, and methylene-carbonyl linker connects natural as well as unnatural nucleo-bases to central amine of N-(2-aminoethyl)glycine. Despite radical change to the natural structure, PNA is capable of sequence specific binding to DNA as well as RNA obeying the Watson-Crick base pairing rule. PNAs bind with higher affinity to complementary nucleic acids than their natural counterparts, partly due to the lack of negative charge on backbone, a consequently reduced charge-charge repulsion, and favorable geometrical factors (S. K. Kim et al., *J. Am. Chem. Soc.*, 1993, 115, 6477-6481; B. Hyrup et al., *J. Am. Chem. Soc.*, 1994, 116, 7964-7970; M. Egholm et al., *Nature*, 1993, 365, 566-568; K. L. Dueholm et al., *New J. Chem.*, 1997, 21, 19-31; P. Wittung et al., *J. Am. Chem. Soc.*, 1996, 118, 7049-7054; M. Leijon et al., *Biochemistry*, 1994, 9820-9825.). Also it was demonstrated that the thermal stability of the resulting PNA/DNA duplex is independent of the salt concentration in the hybridization solution (H. Orum et al., *BioTechniques*, 1995, 19, 472-480; S. Tomac et al., *J. Am. Chem. Soc.*, 1996, 118, 5544-5552.). And PNAs can bind in either parallel or antiparallel fashion, with antiparallel mode being preferred (E. Uhlman et al., *Angew. Chem. Int. Ed. Engl.*, 1996, 35, 2632-2635.).

A mismatch in a PNA/DNA duplex is much more destabilizing than a mismatch in a DNA/DNA duplex. A single base mismatch results in 15° C. and 11° C. lowering of the Tm of PNA/DNA and DNA/DNA, respectively. Homopyrimidine PNA oligomers and PNA oligomers with a high pyrimidine/purine ratio can bind to complementary DNA forming unusually stable PNA2/DNA triple helices (P. E. Nielsen et al., *Science*, 1991, 254, 1497-1500; L. Betts et al., *Science*, 1995, 270, 1838-1841; H. Knudsen et al., *Nucleic Acids Res.*, 1996, 24, 494-500.). Although PNAs have amide bonds and nucleobases, PNAs show great resistance to both nuclease and protease. In contrast to DNA, which depurinates on treatment with strong acids and hydrolyses in alkali hydroxides, PNAs are completely acid stable and sufficiently stable to weak bases.

Generally, PNA oligomers are synthesized using the well established solid phase peptide synthesis protocol. New strategies for monomers have been developed independently by several groups to optimize PNA oligomer synthesis. The preparation of PNA monomers can be divided into the synthesis of a suitably protected N-aminoethylglycine and a suitably protected nucleobase acetic acid derivatives, which is followed by coupling both.

The first synthetic strategy reported for PNA oligomer synthesis was Merrifield solid phase synthesis using t-Boc/benzyloxycarbonyl protecting group strategy wherein the backbone amino group protected with the t-Boc and the exocyclic amino groups of the nucleobases are protected with the benzyloxycarbonyl (P. E. Nielsen et al., *Science*, 1991, 254, 1497-1500; M. Egholm et al., *J. Am. Chem. Soc.*, 1992, 114, 9677-9678; M. Egholm et al., *J. Am. Chem. Soc.*, 1992, 114, 1895-1897; M. Egholm et al., *J. Chem. Soc. Chem. Commun.*, 1993, 800-801; K. L. Dueholm et al., *J. Org. Chem.*, 1994, 59, 5767-5773; WO 92/20702). PNA monomers protected with t-Boc/benzyloxycarbonyl are now commercially available but are inconvenient to use because repeated treatment with TFA is required for t-Boc deprotection and the harsh HF or trifluoromethanesulfonic acid treatment required for cleavage from the resin and deprotection of benzyloxycarbonyl group from exocyclic amine of nucleobases. Thus, this strategy is not compatible with the synthesis of many types of modified PNA oligomers such as PNA-DNA chimera. Furthermore, the use of hazardous acids, such as HF or trifluoromethanesulfonic acid, is not commercially embraced in view of safety concerns for the operator and the corrosive effect on automation equipment and lines. In addition, the t-Boc/benzyloxycarbonyl protection strategy is differential strategy which is defined as a system of protecting groups wherein the protecting groups are removed by the same type of reagent or condition, but rely on the different relative rates of reaction to remove one group over the other. For example, in the t-Boc/benzyloxycarbonyl protecting strategy, both protecting groups are acid labile, but benzyloxycarbonyl group requires a stronger acid for efficient removal. When acid is used to completely remove the more acid labile t-Boc group, there is a potential that a percentage of benzyloxycarbonyl group will also be removed contemporaneously. Unfortunately, the t-Boc group must be removed, from amino group of backbone during each synthetic cycle for the synthesis of oligomer. Thus TFA is strong enough to prematurely deprotect a percentage of the side chain benzyloxycarbonyl group, thereby introducing the possibility of oligomer branching and reducing the overall yield of desired product.

In another effort to find a milder deprotecting method for PNA oligomer synthesis that would be compatible with DNA oligomer synthesis, several research groups have developed PNA monomers protected with Mmt/acyl wherein the backbone amino group protected with the Mmt and the exocyclic amino groups of the nucleobases are protected with an acyl group such as benzoyl, anisoyl, and t-butyl benzoyl for cytosine and adenine, or isobutyryl, acetyl for guanine (D. W. Will et al., *Tetrahedron*, 1995, 51, 12069-12082; P. J. Finn et al., *Nucleic Acid Research*, 1996, 24, 3357-3363; D. A. Stetsenko et al., *Tetrahedron Lett.* 1996, 3571-3574; G. Breipohl et al., *Tetrahedron*, 1997, 14671-14686.).

Alternative PNA monomers protected with Fmoc/benzhydryloxycarbonyl are also commercially available wherein the backbone amino group protected with the Fmoc and the exocyclic amino groups of the nucleobases are protected with the benzhydryloxycarbonyl (J. M. Coull, et al., U.S. Pat. No. 6,133,444). But Fmoc/benzhydryloxycarbonyl strategy has several drawbacks such as side reaction during the Fmoc deprotection process and instability of monomer in solution. The most critical side reaction is the migration of the nucleobase acetyl group from the secondary amino function to the free N-terminal amino function of aminoethylglycine backbone under Fmoc deprotection condition (L. Christensen et al., *J. Pept. Sci.* 1995, 1, 175-183). The N-acetyl transfer reactions in every cycles during oligomer synthesis result in accumulation of side products which are hard to separate due to similar polarity and same molecular weight. Also the Fmoc protecting group is very unstable in the presence of trace amine. Thus, the selection of the solvent for the PNA monomers should be cautious. Generally, N-methylpyrrolidone of high quality is recommended. This requires higher cost in the synthesis of PNA oligomer.

The synthesis of PNA oligomers using Fmoc/benzyloxycarbonyl (S. A. Thomson et al., *Tetrahedron*, 1995, 6179-6194.) and Fmoc/Mmt (G. Breipohl et al., *Bioorg. Med. Chem. Lett.*, 1996, 6, 665-670.) protected monomer has also been reported. However, all of these methods have serious drawbacks in terms of monomer solubility and preparation, harsh reaction condition, and side reactions either during monomer synthesis and/or PNA oligomer synthesis.

In other efforts to find new monomers, cyclic monomers were reported by ISIS and Biocept. The first strategy developed by ISIS replaces protected backbone by morpholinone (U.S. Pat. No. 5,539,083), but the strategy has serious drawback in that the hydroxy functional group generated by coupling reaction should be converted to amine functional group in every elongation step during oligomer synthesis. Alternatively, the protected aminoethylglycine part is replaced by N-t-Boc-piperazinone (WO 00/02899). However, this strategy also has several drawbacks in terms of monomer reactivity in oligomerization and the same problems as seen in linear t-Boc strategy as described above.

Despite recent advances, there remains a need for new monomer that increases yield, lowers synthetic cost, and is suitable for automatic and parallel synthesis.

SUMMARY OF THE INVENTION

The present invention provides novel monomers for increased efficiency, high yield, and convenience during synthesis of PNA oligomers. Another object is to provide PNA monomers that can be conveniently applied to instrumentation such as automated synthesizer for synthesis of PNA oligomers. The novel monomers according to the present invention are compounds having general formula I:

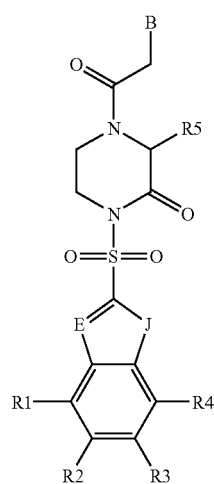

wherein

E may be nitrogen or C—R',

J may be sulfur or oxygen,

R', R1, R2, R3, R4 may be independently H, halogen such as F, Cl, Br or I, $CF_3$, alkyl, preferably $C_1$-$C_4$ alkyl, nitro, nitrile, alkoxy, preferably $C_1$-$C_4$ alkoxy, halogenated (such as F, Cl, Br and I) alkyl, preferably halogenated $C_1$-$C_4$ alkyl, or halogenated (such as F, Cl, Br and I) alkoxy, preferably halogenated $C_1$-$C_4$ alkoxy, phenyl, or halogenated (such as F, Cl, Br and I) phenyl, R5 may be H or protected or unprotected side chain of natural or unnatural α-amino acid, and B may be a natural or unnatural nucleobase, wherein when said nucleobase has an exocyclic amino function, said function is protected by protecting group which is labile to acids but stable to weak to medium bases in the presence of thiol. In another embodiment, B may be thymine (T), cytosine (C), adenine (A), or guanine (G).

Further in particular, the protecting group for the exocyclic amino function of B has a general formula:

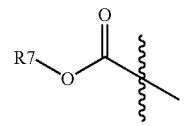

The group-represented by R7 may have a general formula:

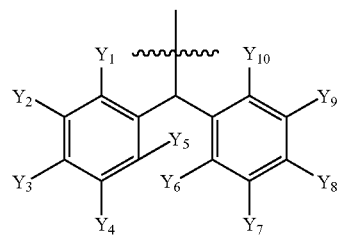

The residue represented by $Y_1$-$Y_{10}$ is independently selected from hydrogen, halogen, such as F, Cl, Br, alkyl, preferably methyl, ethyl, t-butyl, and alkoxy, such as methoxy, ethoxy, and t-butyloxy.

In another embodiment, R7 may have a general formula;

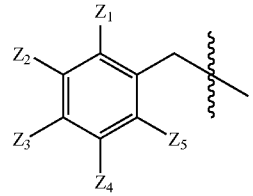

The residue represented by $Z_1$-$Z_5$ is independently selected from hydrogen halogen, such as F, Cl, Br, alkyl, preferably methyl, ethyl, t-butyl, and alkoxy, such as methoxy, ethoxy, and t-butyloxy, and methylene dioxy of adjacent two residues.

In another embodiment, R7 may have a general formula;

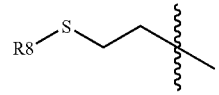

The residue represented by R8 may be alkyl or phenyl.

Further in particular, the protecting group of B may be benzyloxycarbonyl, benzhydryloxycarbonyl, 4-methoxybenzyloxycarbonyl, 3,4-dimethoxybenzyloxycarbonyl, piperonyloxycarbonyl, or 2-methylthioethoxycarbonyl.

The invention is also directed to nucleobase B, which may be protected by piperonyloxycarbonyl derivatives.

In particular, the invention is directed to a cytosine moiety that is protected by piperonyloxycarbonyl derivatives having a general formula:

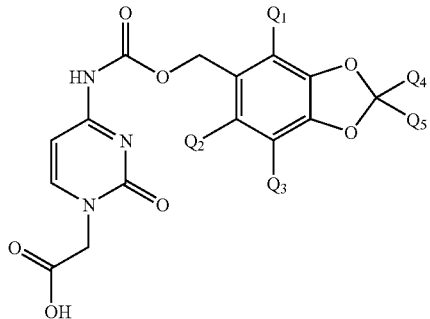

The residue represented by $Q_1$-$Q_5$ may be independently selected from hydrogen, halogen, such as F, Cl, Br, and I, nitro, alkyl, such as methyl, ethyl, and t-butyl, and alkoxy, such as methoxy, ethoxy, and t-butyloxy.

The invention is also directed to an adenine moiety that is protected by piperonyloxycarbonyl derivatives having a general formula:

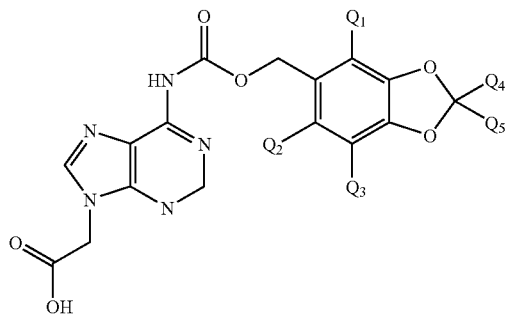

wherein
$Q_1$, $Q_2$, $Q_3$, $Q_4$ and $Q_5$ are as defined above.

The invention is also directed to a guanine moiety that is protected by piperonyloxycarbonyl derivatives having a general formula:

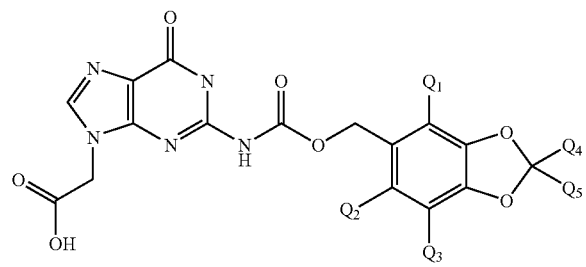

wherein
$Q_1$, $Q_2$, $Q_3$, $Q_4$ and $Q_5$ are as defined above.

The present invention further provides for methods of preparing compounds of general formula I from compounds of general formula V.

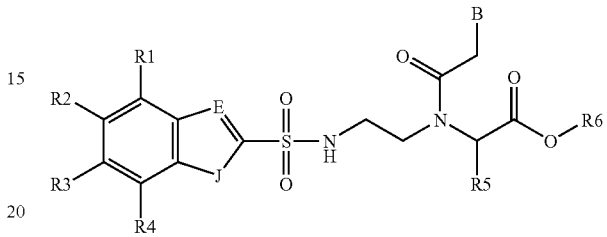

wherein
E, J, R1, R2, R3, R4, R5 and B are as defined above,
the protecting group of B when said nucleobase of B has an exocyclic amino function is also as described above, and
R6 may be H, alkyl, preferably ($C_1$-$C_4$) alkyl (such as methyl, ethyl, and t-butyl), or aryl.

In another embodiment, the invention provides for compounds of general formula V and their preparation methods from compounds of general formula II.

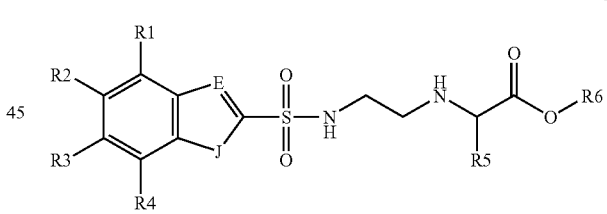

wherein
E, J, R1, R2, R3, R4, R5, and R6 are as defined above.

Also, the present invention provides compounds of formula II and their preparation methods.

In another embodiment, the invention is directed to a method of making the compound of formula V, comprising coupling reaction of a compound of formula II with a nucleobase acetic acid moiety in the presence of non-nucleophilic organic base and a coupling reagent that is customarily used in peptide synthesis.

The present invention further provides methods of preparing compounds of formula I from compounds of general formula IV.

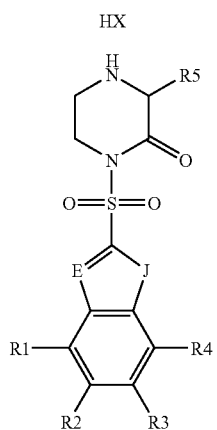

wherein

E, J, R1, R2, R3, R4, and R5 are as defined above, and HX is organic or inorganic acid.

The present invention also provides compounds of general formula IV and their free acid form, and their preparation methods.

The present invention further provides methods of preparing compounds of general formula IV from compounds of general formula II.

The invention is also directed to a method of making the compound of formula I, comprising coupling reaction of a compound of formula IV with a nucleobase acetic acid moiety in the presence of non-nucleophilic organic base and a coupling reagent that is customarily used in peptide synthesis.

The invention is also directed to a method of making the compound of formula I, comprising cyclizing a compound of formula VI in the presence of a coupling reagent that is customarily used in peptide synthesis or mixed anhydride.

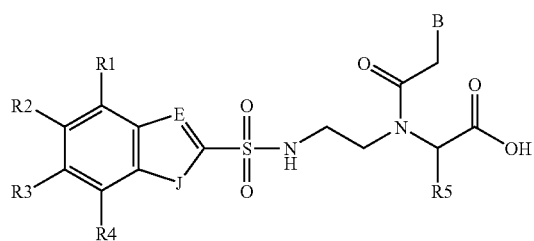

The entities represented by E, J, R1, R2, R3, R4, R5, and B are as defined above. The protecting group of B when said nucleobase of B has an exocyclic amino function is also as set forth, above.

The invention is directed to a compound of formula II, for which its residues are defined as above. In particular, the R5 residue may be H or protected or unprotected side chain of natural α-amino acid. In other embodiments, the compound of formula II may have the following configuration: R1, R2, R3, and R4 may be H, E is nitrogen, and J is sulfur. In other embodiments, R1, R3, and R4 may be H, R2 may be Cl, E is nitrogen, and J is sulfur. In other embodiments, R3 and R4 may be H, R1 may be Cl, R2 may be methoxy, E is nitrogen, and J is sulfur.

The invention is also directed to a method of making the compound of formula II, comprising reacting benzothiazole-2-sulfonylchloride, benzoxazole-2-sulfonylchloride benzo[b]thiophene-2-sulfonylchloride, or benzofuran-2-sulfonylchloride derivative with 2-aminoethylglycine ester in the presence of non-nucleophilic organic base. The invention is further directed to a compound having formula IV and its free acid form. The residues for formula IV are as defined above. In particular, the R5 residue may be H or protected or unprotected side chain of natural α-amino acid. In other embodiments, the compound of formula IV may have the following configuration: R1, R2, R3, and R4 may be H; E is nitrogen and J is sulfur. In other embodiments, R1, R3, and R4 may be H, R2 may be Cl, E is nitrogen, and J is sulfur. In other embodiments, R3 and R4 may be H, R1 may be Cl, R2 may be methoxy, E is nitrogen, and J is sulfur.

The invention is further directed to a method of making the compound of formula IV, comprising cyclizing a compound of formula III in the presence of a coupling reagent that is customarily used in pep tide synthesis or mixed anhydride, followed by deprotection of a protection group such as t-Boc in acid.

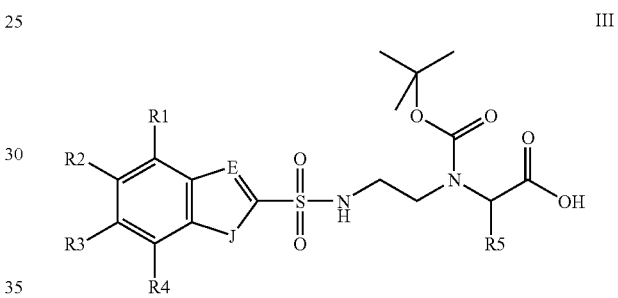

The entities represented by E, J, R1, R2, R3, R4, and R5 are as defined above.

The invention is also directed to a method of making PNA oligomer, comprising linking together the compound of formula I.

It is to be understood that the "R" groups, and E and J designations cited above apply to all of the compounds of formulae I-VI. It is also to be understood that the designations also apply to the compounds as they undergo the processes of the invention.

These and other objects of the invention will be more fully understood from the following description of the invention, the referenced drawings attached hereto and the claims appended hereto. It is further to be understood that the chemical formulae as labeled in the figures serve as representative embodiments. The inventive chemical formulae are discussed throughout the specification. The recited chemical formulae in the figures are not meant to limit the scope of the recited compounds in any way.

BRIEF DESCRIPTION OF THE DRAWINGS

The present invention will become more fully understood from the detailed description given herein below, and the accompanying drawings which are given by way of illustration only, and thus are not limitative of the present invention, and wherein.

DETAILED DESCRIPTION OF THE PREFERRED EMBODIMENTS

Figure 1:
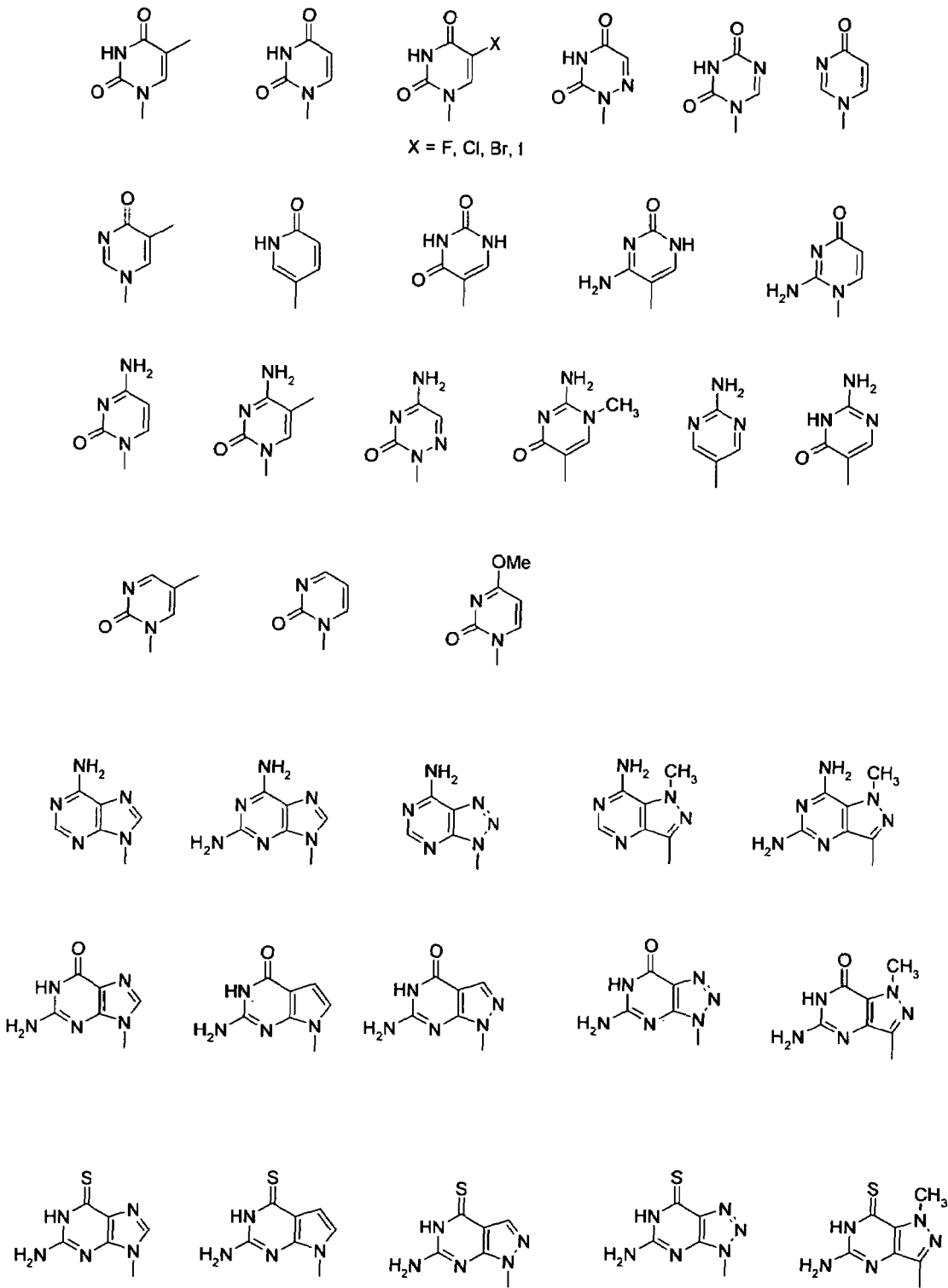
FIG. 1 shows a chart of the chemical structures of naturally and non-naturally occurring nucleobases useful for DNA recognition.

It is to be understood that the formulae depicted in the drawings are merely exemplified versions, and where a particular formula is referred to in the claims, the version discussed in the text of the specification is meant.

Figure 2:
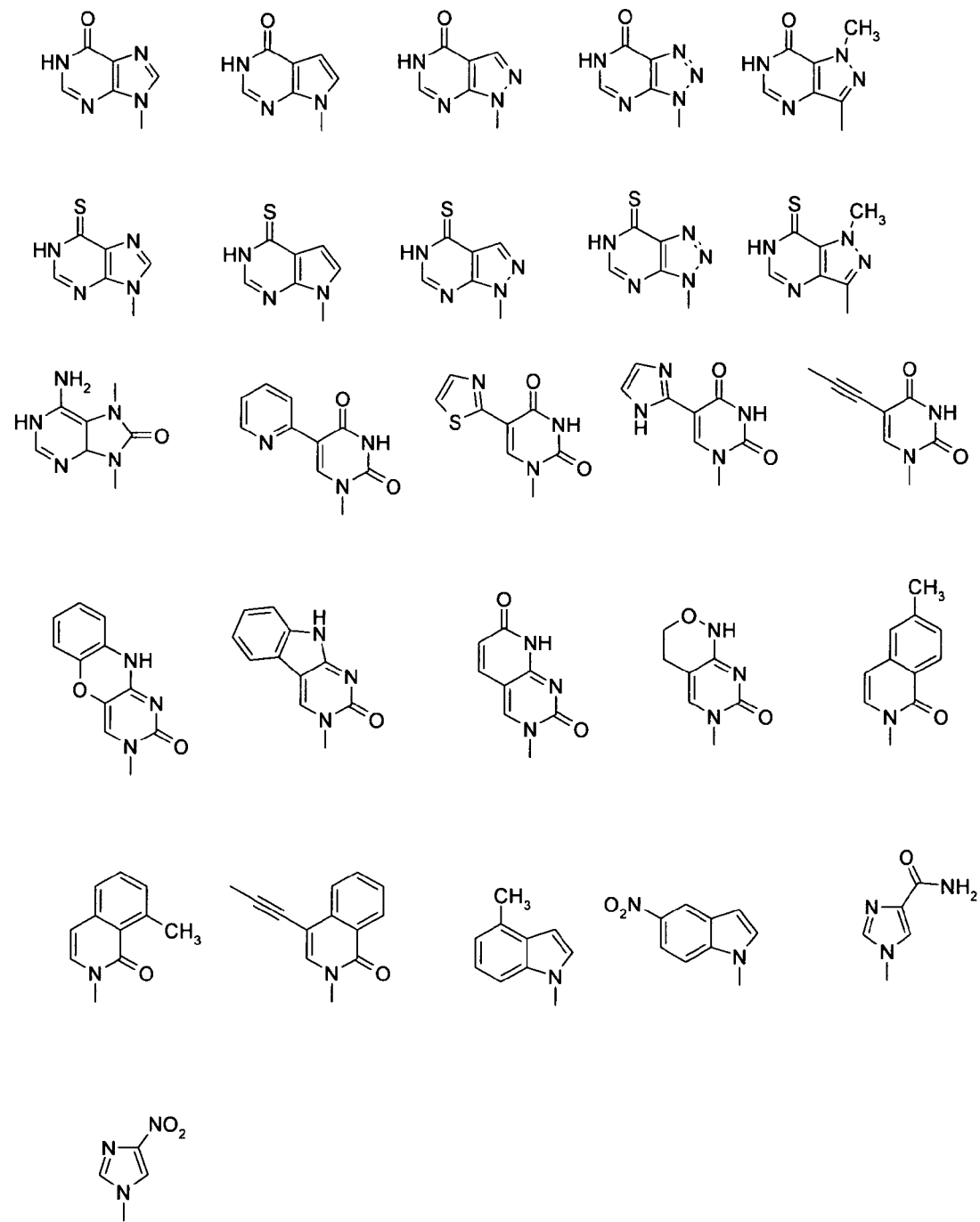
FIG. 2 shows another chart of the chemical structures of naturally and non-naturally occurring nucleobases useful for DNA recognition.
Figure 3:
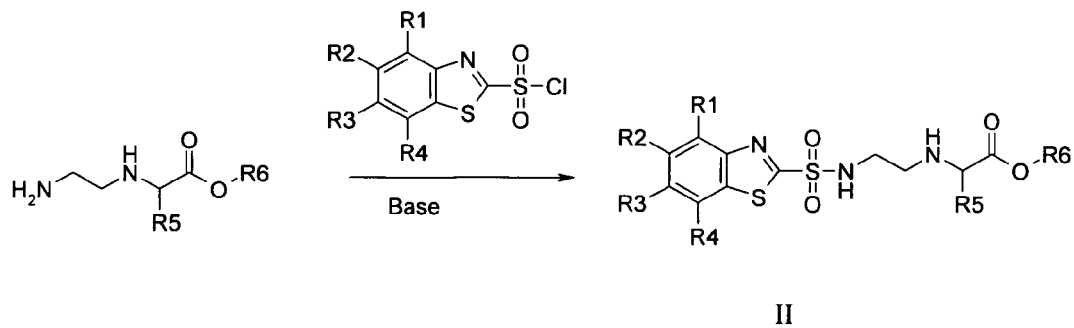
FIG. 3 shows a schematic representation of the synthesis of protected backbone.

In the present invention, benzothiazole-2-sulfonyl, benzo[b]thiophene-2-sulfonyl, benzoxazole-2-sulfonyl, or benzofuran-2-sulfonyl group of compounds having general formula I play an important role not only as protecting groups of amine of backbone but also as activating groups for coupling reaction. The monomers having described characteristics are useful for the synthesis of PNA oligomers by manual or automated synthesizer and the preparation of PNA oligomer library by combinatorial chemistry. Nucleobase B in the general formula I is naturally attached at the position found in nature, i.e., position 1 for thymine or cytosine, and position 9 for adenine or guanine, as well as for non-naturally occurring nucleobase (nucleobase analog), or nucleobase binding moiety. Some nucleobases and illustrative synthetic nucleobases are shown in FIG. 1 and FIG. 2.

Preparation of Protected Backbones

The first step for the preparation of novel monomers having general formula I is synthesis of N-[2-(benzothiazole, benzoxazole, benzo[b]thiophene, or benzofuran-2-sulfonylamino)-ethyl]-glycine derivatives having the formula II:

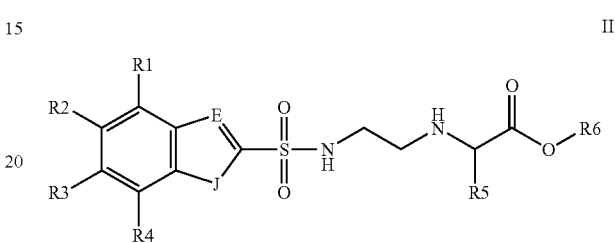

wherein E is nitrogen and J is sulfur for N-[2-(benzothiazole-2-sulfonylamino)-ethyl]-glycine derivatives; E is nitrogen and J is oxygen for N-[2-(benzoxazole-2-sulfonylamino)-ethyl]-glycine derivatives; E is C—R' and J is sulfur for N-[2-(benzo[b]thiophene-2-sulfonylamino)-ethyl]-glycine derivatives; E is C—R' and J is oxygen for N-[2-(benzofuran-2-sulfonylamino)-ethyl]-glycine derivatives; and R', R1, R2, R3, R4, R5, and R6 are as defined above.

Derivatives having formula II are generally synthesized by selective reaction of primary amine of 2-aminoglycine derivatives with sulfonyl chloride compounds having the general formula:

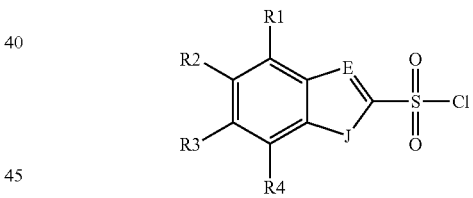

wherein E is nitrogen and J is sulfur for benzothiazole-2-sulfonyl chloride derivatives; E is nitrogen and J is oxigen for benzoxazole-2-sulfonyl chloride derivatives; E is C—R' and J is sulfur for benzo[b]thiophene-2-sulfonyl chloride derivatives; E is CH and J is oxygen for benzofuran-2-sulfonyl chloride derivatives; and R', R1, R2, R3, and R4 are as defined above.

For an example of preparing derivatives having formula II, N-[2-(Benzothiazole-2-sulfonylamino)-ethyl]-glycine derivatives are synthesized by selective reaction of primary amine of 2-aminoglycine derivatives prepared by known methods (for instance, where R1 is H, see S. A. Thomson et al., Tetrahedron, 1995, 6179-6194; where R5 is a side chain of a protected or unprotected natural or unnatural amino acid, see A. Puschl et al., Tetrahedron Lett., 1998, 39, 4707-4710). Benzothiazole-2-sulfonyl chloride derivatives are prepared by known methods (E. Vedejs, et al., J. Am. Chem. Soc., 1996, 118, 9796-9797.).

The coupling reaction for the preparation of N-[2-(benzothiazole, benzoxazole, benzo[b]thiophene, or benzofuran- 2-sulfonylamino)-ethyl]-glycine derivatives is performed by slow addition of benzothiazole-2-sulfonyl chloride, benzoxazole-2-sulfonyl chloride, benzo[b]thiophene-2-sulfonyl chloride, or benzofuran-2-sulfonyl chloride to a solution of N-(2-aminoethyl)-glycine derivatives in the presence of non-nucleophilic organic base at ambient temperature. Examples of solvents of above reaction include without limitation water, toluene, benzene, ethylacetate, tetrahydrofuran, diisopropylether, diethylether, dichloromethane, chloroform, carbon tetrachloride, and acetonitrile. Preferred solvent is dichloromethane. Examples of non-nucleophilic organic bases include, but are not limited to, triethylamine, tripropylamine N,N-diisopropylethylamine, N-methylmorpholine, and N-ethylmorpholine. Preferred non-nucleophilic organic base is triethylamine. After completion of the reaction by monitoring by thin layer chromatography (TLC), the reaction mixture is washed with water, dried, and evaporated in reduced pressure to give the desired product.

Figure 4:
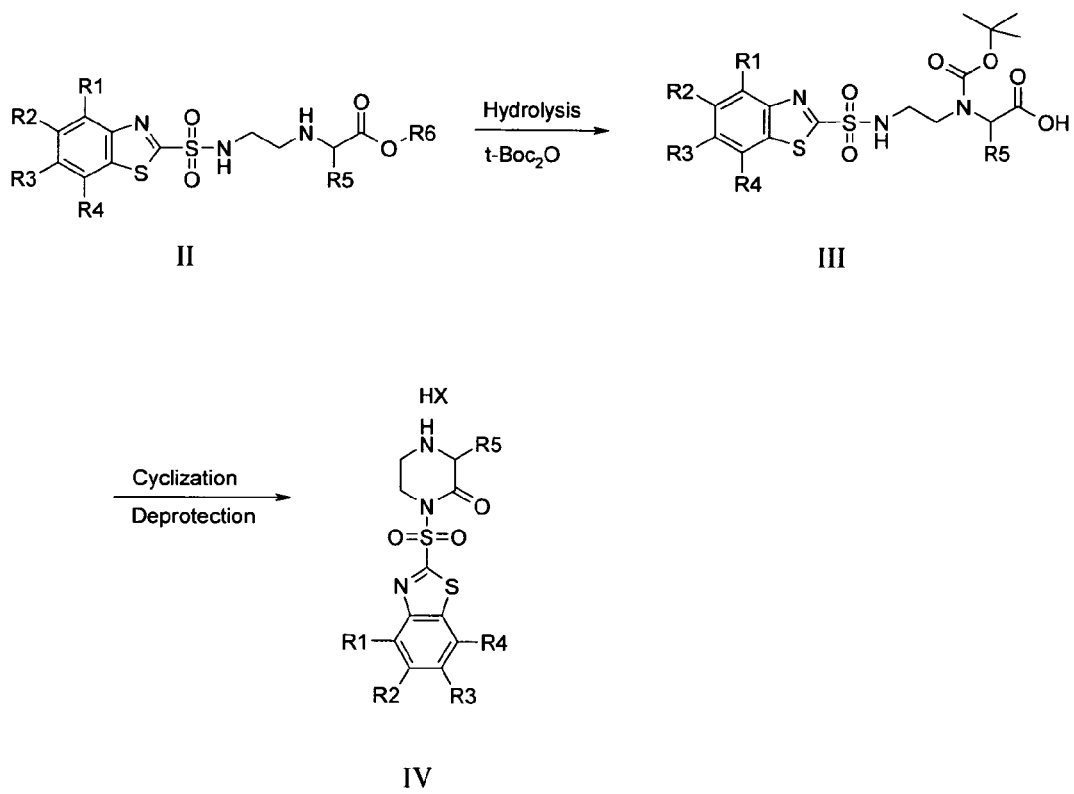
FIG. 4 shows a schematic representation of the synthesis of protected piperazinone as a precursor for monomer.

Preparation of 1-(benzothiazole, benzoxazole, benzo[b]thiophene or benzofuran-2-sulfonyl)-piperazin-2-ones The first precursor synthons having formula IV for synthesis of monomers having general formula I are prepared from N-[2-(benzothiazole, benzoxazole, benzo[b]thiophene, or benzofuran-2-sulfonylamino)-ethyl]-glycine derivatives having the formula II by hydrolysis, protection of secondary amine, cyclization, and deprotection of protecting group of secondary amine (FIG. 4).

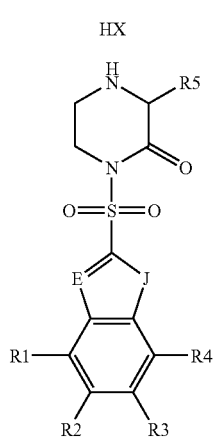

IV

The entities represented by E, J, R1, R2, R3, R4, R5, and HX may be as defined above.

First, N-[2-(benzothiazole, benzoxazole, benzo[b]thiophene, or benzofuran-2-sulfonylamino)-ethyl]-glycine derivatives having the formula II are converted to corresponding acids by adding excess hydroxide ion source. Preferred R6 in the formula II is methyl or ethyl. Examples of hydroxide ion sources include, but are not limited to, lithium hydroxide, sodium hydroxide, and potassium hydroxide. Preferred hydroxide ion source is lithium hydroxide. The reaction mixture; without work-up is then treated with a protecting group such as di-t-butyl dicarbonate to protect secondary amine to obtain a compound having the general formula:

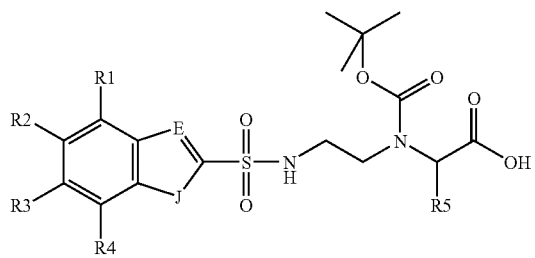

III

The entities represented by E, J, R1, R2, R3, R4, and R5 are as defined above.

Preferred hydrolysis reaction is carried out by adding an aqueous solution of lithium hydroxide (2 equivalent) to a solution of N-[2-(benzothiazole, benzoxazole, benzo[b]thiophene, or benzofuran-2-sulfonylamino)-ethyl]-glycine ester derivative at ambient temperature. After completion of the reaction by TLC analysis, an aqueous solution of lithium hydroxide (additional 1 equivalent) is added to the reaction mixture. The reaction mixture is stirred for sufficient time. Then the excess di-t-butyl dicarbonate is removed by extraction with ethylacetate. The aqueous solution is then acidified, extracted with dichloromethane, dried, and evaporated in reduced pressure to yield a solid. Examples of solvents of above reaction are aqueous tetrahydrofuran, aqueous dioxane, and aqueous 1,2-dimethoxyethane. Preferred solvent is aqueous tetrahydrofuran.

Second, the cyclization reaction of carboxylic acids having general formula III and followed by deprotection of t-Boc produces piperazinone derivatives having general formula IV. The cyclization reaction occurs simultaneously during activation of carboxylic acid. The activation of carboxylic acid can be conducted by general coupling reagent for peptide synthesis at ambient temperature. Examples of coupling reagents include, but are not limited to, HATU, HOAt, HODhbt (L. A. Carpino et al., *J. Am. Chem. Soc.*, 1993, 115, 4397-4398), HAPyU, TAPipU (A. Ehrlich et al., *Tetrahedron Lett.*, 1993, 4781-4784), HBTU (V. Dourtoglou et al., *Synthesis*, 1984, 572-574), TBTU, TPTU, TSTU, TNTU (R. Knorr et al., *Tetrahedron Lett.*, 1989, 1927-1930), TOTU, BOP (B. Castro et al., *Tetrahedron Lett.*, 1975, 1219-1222), PyBOP (J. Coste et al., *Tetrahedron Lett.*, 1990, 205-208), BroP (J. Coste et al., *Tetrahedron Lett.*, 1990, 669-672), PyBroP (J. Coste et al., *Tetrahedron Lett.*, 1991, 1967-1970), BOI (K. Akaji et al., *Tetrahedron Lett.*, 1992, 3177-3180), MSNT (B. Blankemeyer-Menge et al., *Tetrahedron Lett.*, 1990, 1701-1704), TDO (R. Kirstgen et al., *J. Chem. Soc., Chem. Commun.*, 1987, 1870-1871), DCC, EDCI, CDI (H. A. Staab, *Justus Liebigs Ann. Chem.*, 1957, 609, 75.), HOBt (W König et al., *Chem. Ber.*, 1970, 103, 788, 2024, 2034), HOSu (E. Wunsch et al., *Chem. Ber.*, 1966, 99, 110), NEPIS (R. B. Woodward et al., *J. Am. Chem. Soc.;* 1961, 83, 1010), BBC (S. Chen et al., *Tetrahedron Lett.* 1992, 33, 647), BDMP (P, Li et al., *Chem. Lett.*, 1999, 1163), BOMI (P, Li et al., *Tetrahedron Lett.*, 1999, 40, 3605), AOP (L. A Carpino et al., *Tetrahedron Lett.*, 1994, 35, 2279), BDP (S. Kim et al., *Tetrahedron Lett.*, 1985, 26, 1341), PyAOP (F. Albericio et al., *Tetrahedron Lett.* 1997, 38, 4853), TDBTU (R. Knorr et al., *Tetrahedron Lett.* 1989, 30, 1927), BEMT (P. Li et al., *Tetrahedron Lett.* 1999, 40, 8301), BOP-Cl (J. Diago-Meseguer et al., *Synthesis* 1980, 547), BTFFH, TFFH (A. El-Faham et al. *Chem.*

*Lett.*, 1998, 671), CIP (K. Akaji, et al., *Tetrahedron Lett.*, 1994, 35, 3315), DEPBT (H. Li et al. *Organic Lett.* 1999, 1, 91), Dpp-Cl (R. Ramage et al., *J. Chem. Soc., Perkin Trans* 1, 1985, 461), EEDQ (B, Belleau et al., *J. Am. Chem. Soc.*, 1968, 90, 1651), FDPP (S Chen et al., *Tetrahedron Lett.*, 1991, 32, 6711), HOTT, TOTT (M. A. Bailén et al., *J. Org. Chem.* 1999, 64, 8936), PyCloP (J. Coste et al., *Tetrahedron Lett.*, 1991, 32, 1967 and J. Coste et al., *J. Org. Chem.*, 1994, 59, 2437). The solvents may be selected from tetrahydrofuran, dichloromethane, chloroform, DMF, and N-methylpyrrolidone. Preferred solvent is DMF.

Alternatively, the activation of carboxylic acid can be conducted by formation of mixed anhydride using alkyl chloroformate or alkanoyl chloride with non-nucleophilic organic base. Examples of alkyl haloformates or alkanoyl chlorides include, but are not limited to, methyl chloroformate, ethyl, chloroformate, propyl chloroformate, butyl chloroformate, isobutyl chloroformate, pivaloyl chloride, and adamantine carboxyl chloride. The most preferred acid chloride is isobutyl chloroformate. The cyclization reaction using isobutyl chloroformate is carried out by slowly adding isobutyl chloroformate to a reaction solution of carboxylic acid having general formula III and non-nucleophilic organic base in an anhydrous appropriate solvent at the temperature between −30° C. and 10° C. Examples of non-nucleophilic organic bases include, but are not limited to, triethylamine, tripropylamine, N,N-diisopropylethylamine, N-methylmorpholine, and N-ethylmorpholine. Preferred non-nucleophilic organic base is N-methylmorpholine. Examples of anhydrous appropriate solvents include, but, are not limited to, acetonitrile, chloroform, dichloromethane, 1,2-dimethoxy ethane, diethyl ether, diisoproyl ether, and tetrahydrofuran. Preferred solvents are dichloromethane and tetrahydrofuran. The most preferred reaction temperature is in which the reaction mixture is allowed to slowly warm to 0° C. after completing addition of isobutyl chloroformate at −20° C.

With reference to FIG. 4, the t-Boc group is deprotected in the presence of acid. Examples of acids include, but are not limited to, HCl, HBr, HF, HI, nitric acid, sulfuric acid, methanesulfonic acid, TFA, and trifluoromethanesulfonic acid. Preferred acid is, TFA. The solvents used in the deprotection reaction may include without limitation dichloromethane, chloroform, carbon tetrachloride, ethyl acetate, toluene, and benzene. Preferred is dichloromethane.

Synthesis of PNA Monomer

Figure 5:
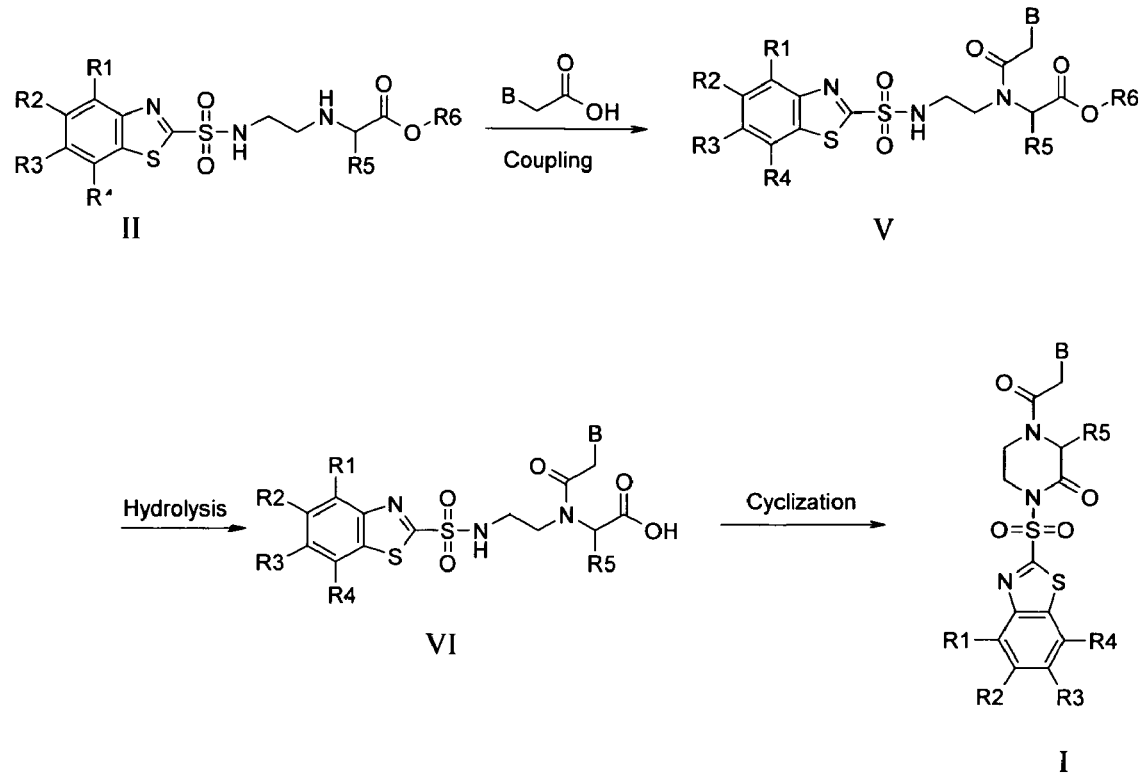
FIG. 5 shows a schematic representation of the synthesis of PNA monomer.

According to a method of this invention, PNA monomers having general formula I may be synthesized by at least two methods. With reference to FIG. 5, the first approach to PNA monomer syntheses is a method that introduces protected or unprotected nucleobase acetic acid moieties to protected linear backbone prior to cyclization reaction. Alternatively, PNA monomers may be synthesized by beginning with cyclization of protected linear backbone, followed by coupling of protected or unprotected nucleobase acetic acid moieties to create desired products.

Method 1

The linear moieties having general formula V are prepared from protected linear backbone having general formula II by acylation of nucleobase acetic acid moieties using coupling reagents as shown in FIG. 5.

With reference to FIG. 5, the coupling reaction was conducted by addition of coupling reagent to the mixture of protected linear backbone having general formula II, nucleobase acetic acid moieties, and non-nucleophilic organic base in anhydrous appropriate solvent. Examples of coupling reagents include, but are not limited to, HATU, HOAt, HODhbt, HAPyU, TAPipU, HBTU, TBTU, TPTU, TSTU, TNTU, TOTU, BOP, PyBOP, BroP, PyBroP, BOI, MSNT, TDO, DCC, EDCI, CDI, HOBt, HOSu, NEPIS, BBC, BDMP, BOMI, AOP, BDP, PyAOP, TDBTU, BOP-Cl, CIP, DEPBT, Dpp-Cl, EEDQ, FDPP, HOTT, TOTT, PyCloP. Preferred coupling reagent is PyBOP. Examples of non-nucleophilic organic bases include, but are not limited to, triethylamine, tripropylamine, N,N-diisopropylethylamine, N-methylmorpholine, and N-ethylmorpholine. Preferred non-nucleophilic organic base is N,N-diisopropylethylamine. Examples of anhydrous appropriate solvents include, but are not limited to, chloroform, dichloromethane, 1,2-dimethoxyethane, tetrahydrofuran, DMF, and N-methylpyrrolidone. Preferred solvent is DMF.

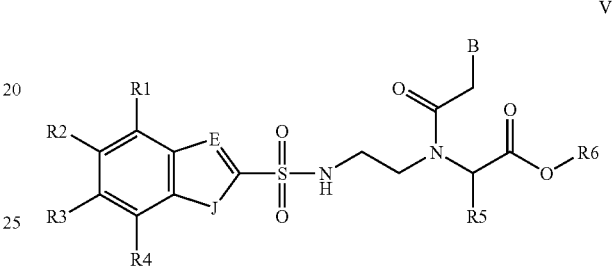

V

The entities represented by E, J, R1, R2, R3, R4, R5, R6, and B are as defined above.

Compounds having the general formula V are converted to corresponding acids such as formula VI by adding an excess of hydroxide ion source. Preferably, R6 may be a methyl, ethyl or t-butyl. Examples of hydroxide ion sources include, but are not limited to, lithium hydroxide, sodium hydroxide, and potassium hydroxide. Preferred hydroxide ion source is lithium hydroxide.

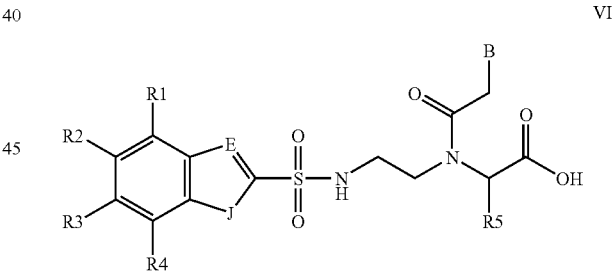

VI

The entities represented by E, J, R1, R2, R3, R4, R5, and B are as defined above.

Further, with reference to FIG. 5, the cyclization reaction of carboxylic acids produces PNA monomers having the general formula I by simultaneous reaction during activation of carboxylic acid. The activation of carboxylic acid may be conducted by general coupling reagent for peptide synthesis at ambient temperature. Examples of coupling reagents include, but are not limited to, HATU, HOAt, HODhbt, HAPyU, TAPipU, HBTU, TBTU, TPTU, TSTU, TNTU, TOTU, BOP, PyBOP, BroP, PyBroP, BOI, MSNT, TDO, DCC, EDCI, CDI, HOBt, HOSu, NEPIS, BBC, BDMP, BOMI, AOP, BDP, PyAOP, TDBTU, BOP-Cl, CIP, DEPBT, Dpp-Cl, EEDQ, FDPP, HOTT, TOTT, PyCloP. Preferred coupling reagent is PyBOP. Examples of non-nucleophilic organic bases include, but are not limited to, triethylamine, tripropylamine, N,N-diisopropylethylamine, N-methylmorpholine, and N-ethylmorpholine. Preferred non-nucleophilic organic base is N,N-diisopropylethylamine. The solvents may be without limitation selected from tetrahydrofuran, dichloromethane, chloroform, DMF, or N-methylpyrrolidone. Preferred solvent is DMF.

Alternatively, the activation of carboxylic acid can be conducted by formation of mixed anhydride using alkyl chloroformate or alkanoyl chloride with non-nucleophilic organic base. Examples of alkyl haloformates or alkanoyl chlorides include, but are not limited to, methyl chloroformate, ethyl chloroformate, propyl chloroformate, butyl chloroformate, isobutyl chloroformate, pivaloyl chloride, and adamantine carboxyl chloride. The most preferred acid chloride is isobutyl chloroformate. The cyclization reaction using isobutyl chloroformate is carried out by slowly adding isobutyl chloroformate to a reaction solution of carboxylic acid and non-nucleophilic organic base in an anhydrous appropriate solvent at a temperature between −30° C. and 10° C. Examples of non-nucleophilic organic bases include, but are not limited to, triethylamine, tripropylamine, N,N-diisopropylethylamine, N-methylmorpholine, and N-ethylmorpholine. Preferred non-nucleophilic organic base is N-methylmorpholine. Examples of anhydrous appropriate solvents include, but are not limited to, acetonitrile, chloroform, dichloromethane, 1,2-dimethoxyethane, diethyl ether, diisoproyl ether, and tetrahydrofuran. Preferred solvents are dichloromethane and tetrahydrofuran. Preferred reaction temperature is in which the reaction mixture is allowed to slowly warm to about 0° C. after completing addition of isobutyl chloroformate at −20° C.

Method 2

As an alternative method, PNA monomers according to this invention may be prepared by coupling of protected or unprotected nucleobase acetic acid moieties to cyclic precursor having the general formula IV:

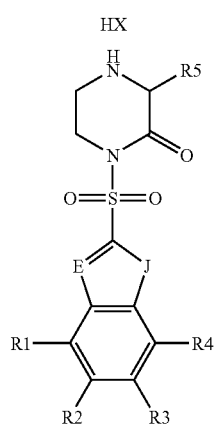

IV

The entities represented by E, J, R1, R2, R3, R4, and R5 are as defined above.

Figure 6:
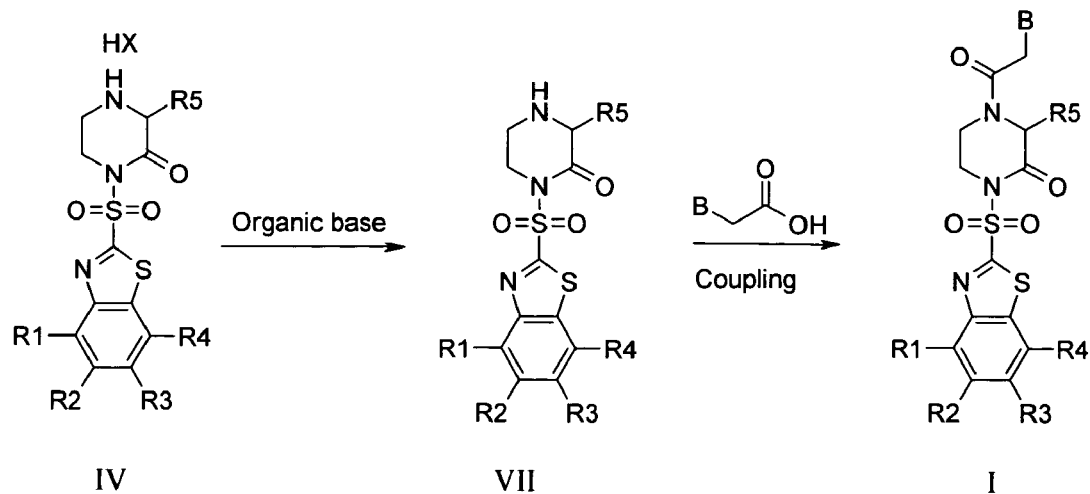
FIG. 6 shows a schematic representation of the alternative synthesis of PNA monomer.

With reference to FIG. 6, the coupling reaction of cyclic precursor with protected or unprotected nucleobase acetic acid moieties is carried out by using general coupling reagent for peptide synthesis and non-nucleophilic organic bases at ambient temperature. Examples of coupling reagents include, but are not limited to, HATU, HOAt, HODhbt, HAPyU, TAPipU, HBTU, TBTU, TPTU, TSTU, TNTU, TOTU, BOP, PyBOP, BroP, PyBroP, BOI, MSNT, TDO, DCC, EDCI, CDI, HOBt, HOSu, NEPIS, BBC, BDMP, BOMI, AOP, BDP, PyAOP, TDBTU, BOP-Cl, CIP, DEPBT, Dpp-Cl, EEDQ, FDPP, HOTT, TOTT, PyCloP. Preferred coupling reagent is PyBOP. Examples of non-nucleophilic organic bases include, but are not limited to, triethylamine, tripropylamine, N,N-diisopropylethylamine, N-methylmorpholine, and N-ethylmorpholine. Preferred non-nucleophilic organic base is N,N-diisopropylethylamine. The solvent may be without limitation tetrahydrofuran, dichloromethane, chloroform, DMF, or N-methylpyrrolidone. Preferred solvent is DMF.

Nucleobases and Protecting Group

Examples of nucleobases of this invention include, but are not limited to, adenine, cytosine, guanine, thymine, uridine, 2,6-diaminopurine, and naturally or non-naturally occurring nucleobases as depicted in FIG. 1 and FIG. 2. Preferred nucleobases are adenine, cytosine, guanine, and thymine. Nucleobases may be protected by protecting group for the syntheses of PNA oligomers. Protecting groups may be, but are not limited to, Boc, adamantyloxycarbonyl, benzyloxycarbonyl (P. E. Nielsen et al., *Science*, 1991, 254, 1497-1500; M. Egholm et al., *J. Am. Chem. Soc.*, 1992, 114, 9677-9679; M. Egholm et al., *J. Am. Chem. Soc.*, 1992, 114, 1895-1897; M. Egholm et al., *J. Chem. Soc. Chem. Commun.*, 1993, 800-801; K. L. Dueholm et al., *J. Org. Chem.*, 1994, 59, 5767-5773; WO 92/20702), 4-methoxybenzyloxycarbonyl, 3,4-dimethoyxbenzyloxycarbonyl, benzhydryloxycarbonyl (U.S. Pat. No. 6,133,444), piperonyloxycarbonyl derivatives, 2-methylthioethoxycarbonyl (U.S. Pat. No. 6,063,569), Mmt (G. Breipohl et al., *Bioorg. Med. Chem. Lett.*, 1996, 6, 665-670), or acid labile protecting group (T. W. Greene and P. G. M. Wuts, Protective Group in Organic Synthesis, 3$^{rd}$ Edition, pp 494–653).

Synthesis of T-Monomer

T-monomer is a compound having general formula I-t:

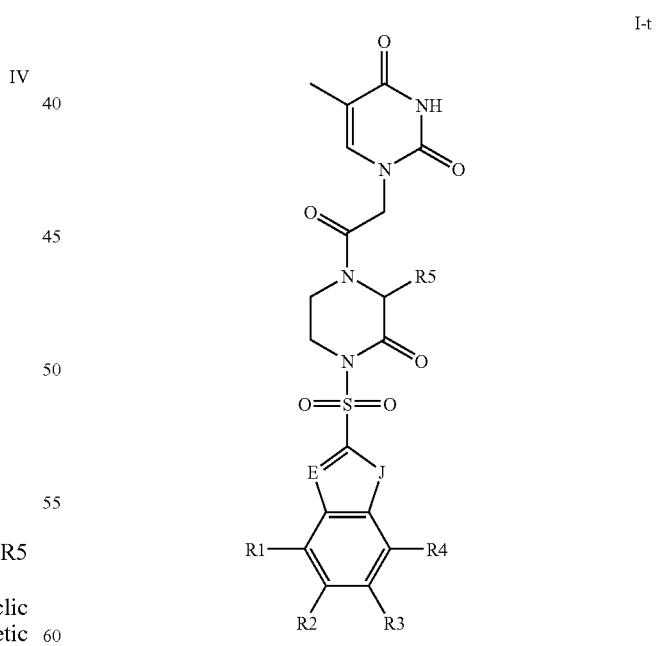

I-t

The entities represented by E, J, R1, R2, R3, R4, and R5 are as defined above. Preferably E is nitrogen, and J is sulfur.

The precursor for T-monomer, (thymin-1-yl)-acetic acid (shown below), is prepared by known methods (K. L. Dueholm et. al., *J. Org. Client.*, 1994, 59, 5767-5773; WO 92/20702).

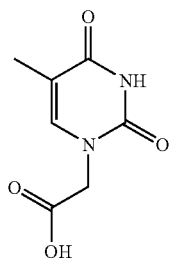

Figure 8:
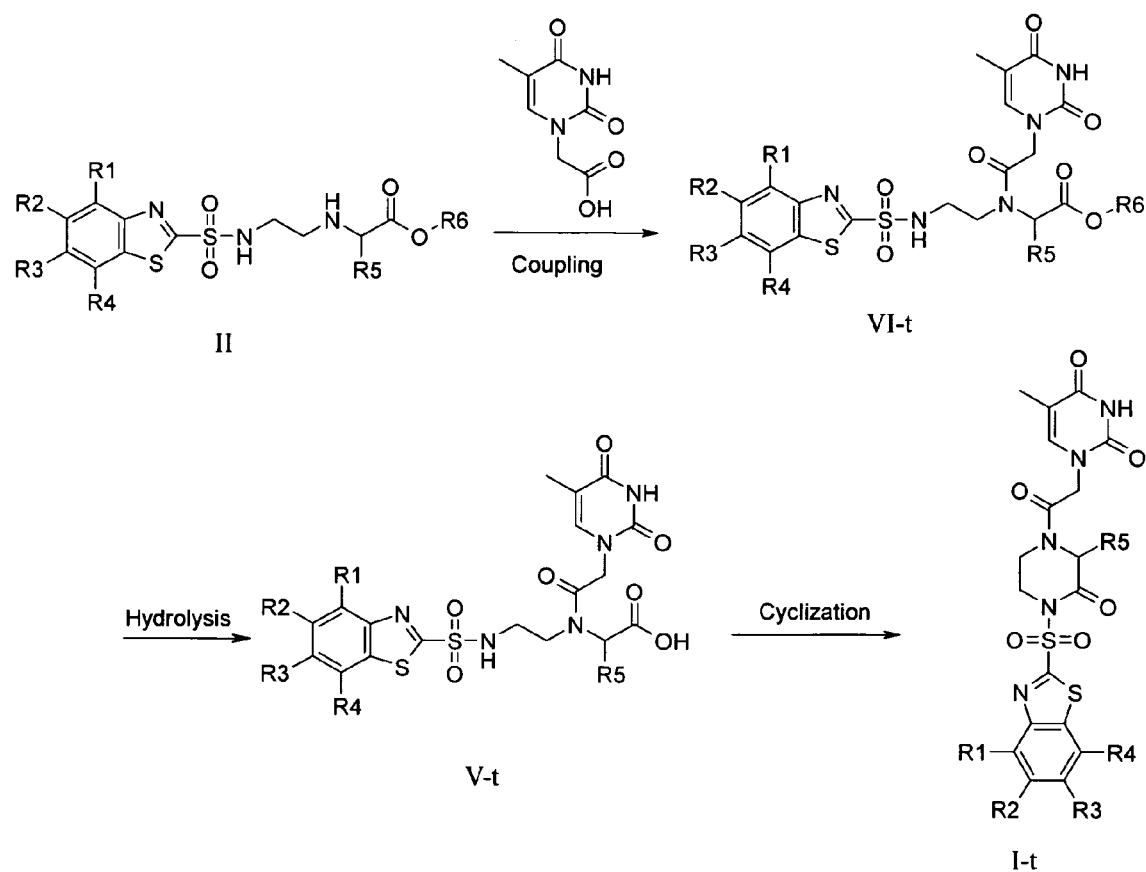
FIG. 8 shows a schematic representation of the synthesis of PNA thymine monomer.

With reference to FIG. 8, the compounds of general formula V-t are prepared by coupling reaction of (thymin-1-yl)-acetic acid with benzothiazole-2-sulfonyl, benzoxazole-2-sulfonyl, benzo[b]thiophene-2-sulfonyl or benzofuran-2-sulfonyl group protected backbone ester having general formula II in the presence of coupling reagent to afford the compound having general formula:

V-t

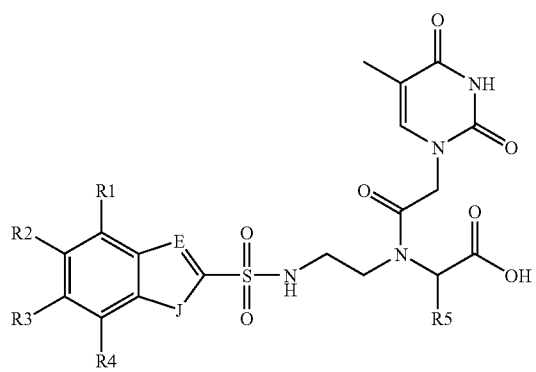

The entities represented by E, J, R1, R2, R3, R4, R5, and R6 are as defined above. Preferably E is nitrogen, and J is sulfur.

Preferred R6 is methyl, ethyl or t-butyl.

The compounds having the general formula V-t are converted to corresponding acids by adding an excess hydroxide ion source to afford the compound having general formula VI-t.

VI-t

The entities represented by E, J, R1, R2, R3, R4, and R5 are as defined above. Preferably E is nitrogen, and J is sulfur.

With reference to FIG. 8, the cyclization reaction of carboxylic acids produces PNA T-monomers having general formula I-t by simultaneous reaction during activation of carboxylic acid. The activation of carboxylic acid may be conducted by general coupling reagent for peptide synthesis or mixed anhydride. The reaction conditions and reagents are the same as described above.

Figure 9:
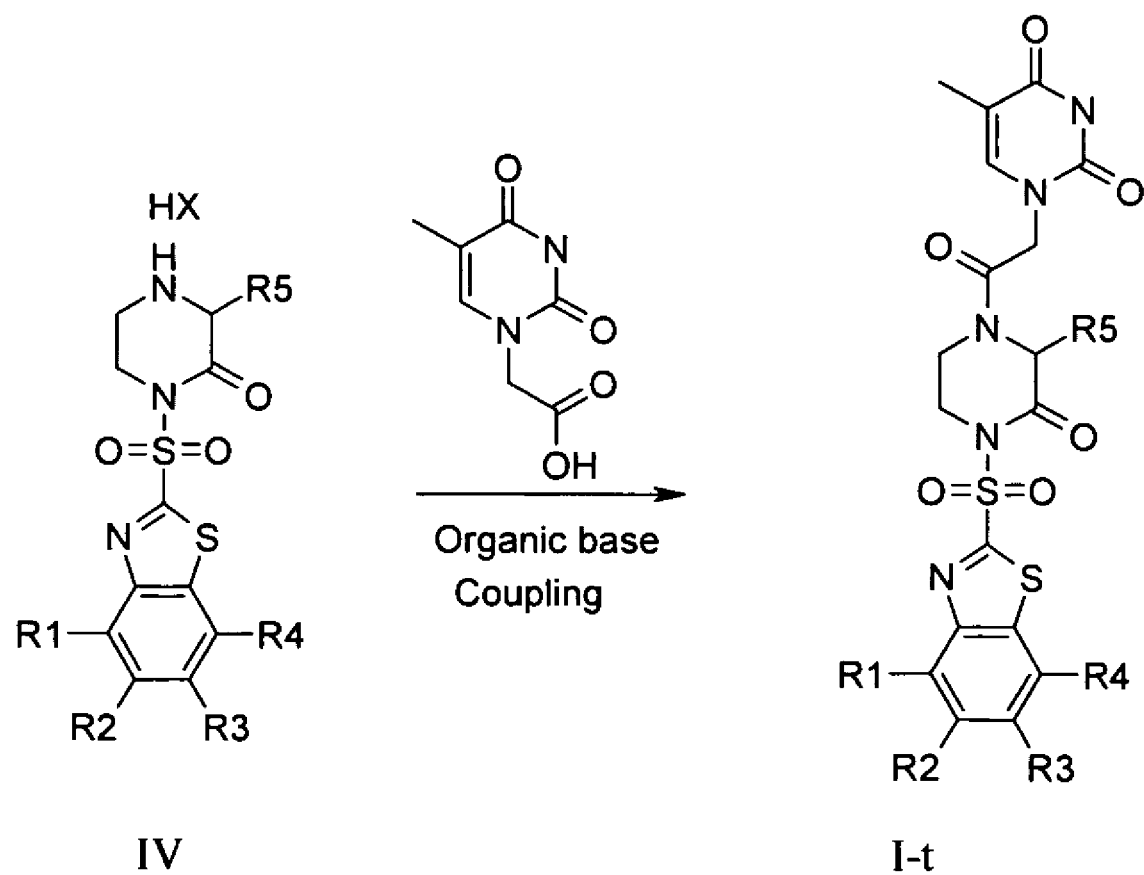
FIG. 9 shows a schematic representation of the alternative synthesis of PNA thymine monomer.

Alternatively, as seen in FIG. 9, PNA T-monomers can be prepared by coupling (thymin-1-yl)-acetic acid to piperazinone derivatives having general formula IV. The reaction conditions and reagents are the same as described above.

Synthesis of C-Monomer

C-monomer is a compound having general formula I-c:

I-c

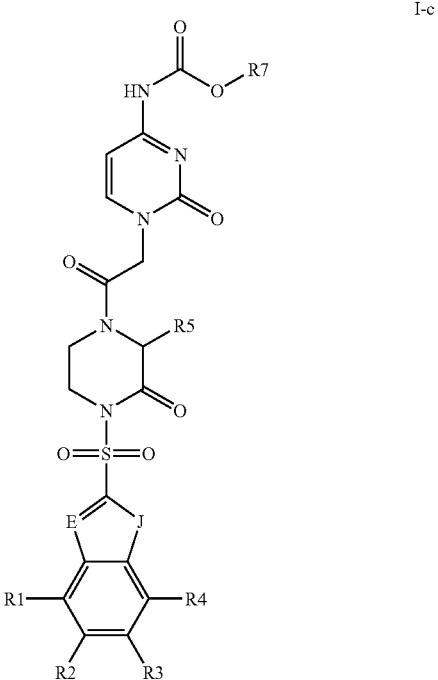

The entities represented by E, J, R1, R2, R3, R4, R5, and R7 are as defined above. Preferably E is nitrogen, and J is sulfur.

Figure 7:
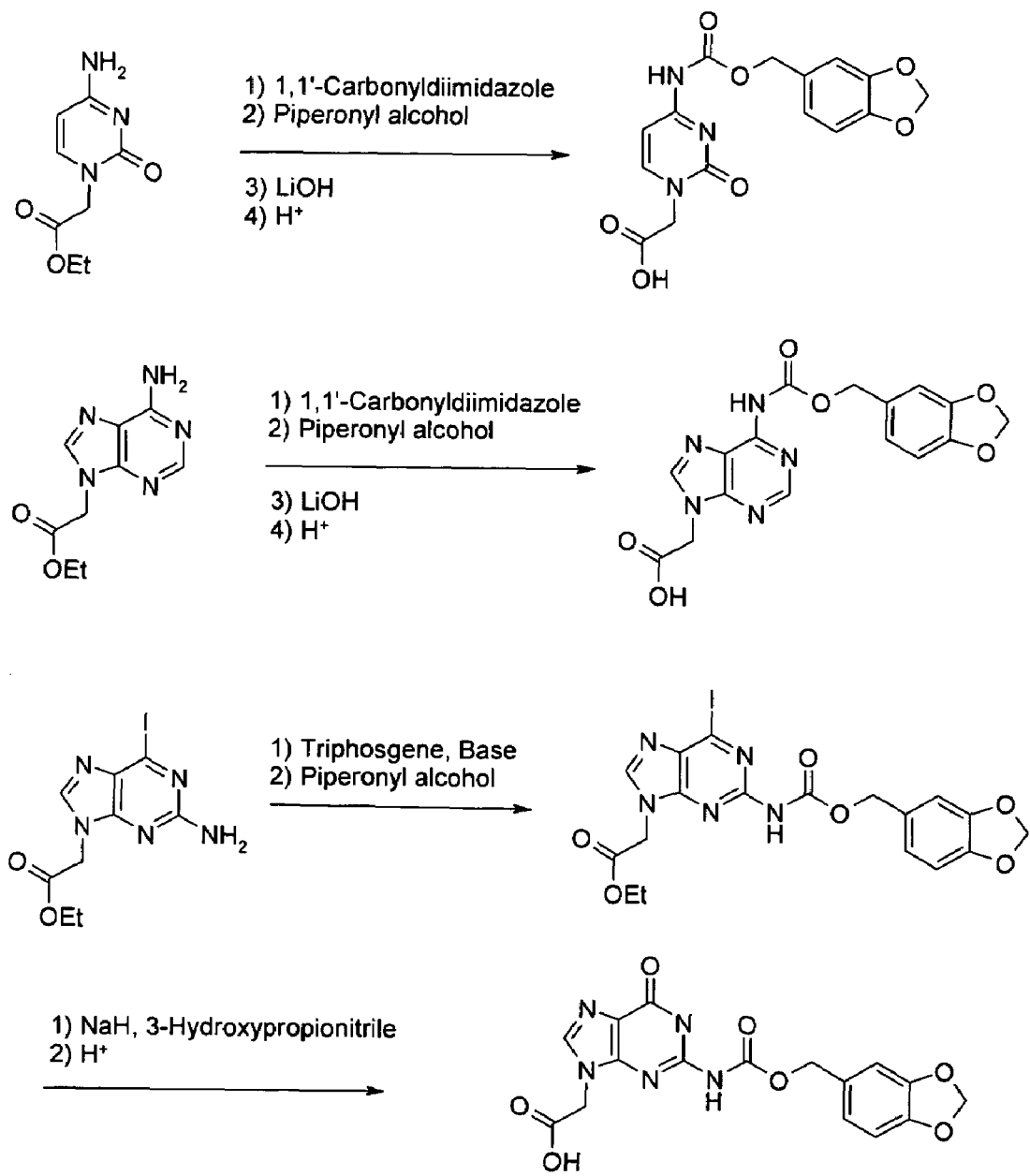
FIG. 7 shows schemes of preparation of nucleobases protected with piperonyloxycarbonyl.

The precursors for PNA C-monomers, suitably protected (cytosin-1-yl)-acetic acids (shown below), are prepared by the method according to the scheme as depicted in FIG. 7 and known methods such as described in U.S. Pat. Nos. 6,133,444; 6,063,569; Dueholm, et al., *J. Org. Chem.,* 1994, 59, 5767-5773; and WO 92/20702, which are incorporated by reference herein in their entirety, or modifications thereof.

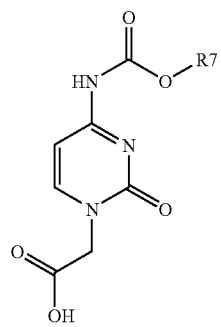

R7 may be methyl, ethyl, benzyl, benzhydryl, 4-methoxybenzyl, 3,4-dimethoxybenzyl, piperonyl derivatives, or 2-methylthioethyl group.

Figure 10:
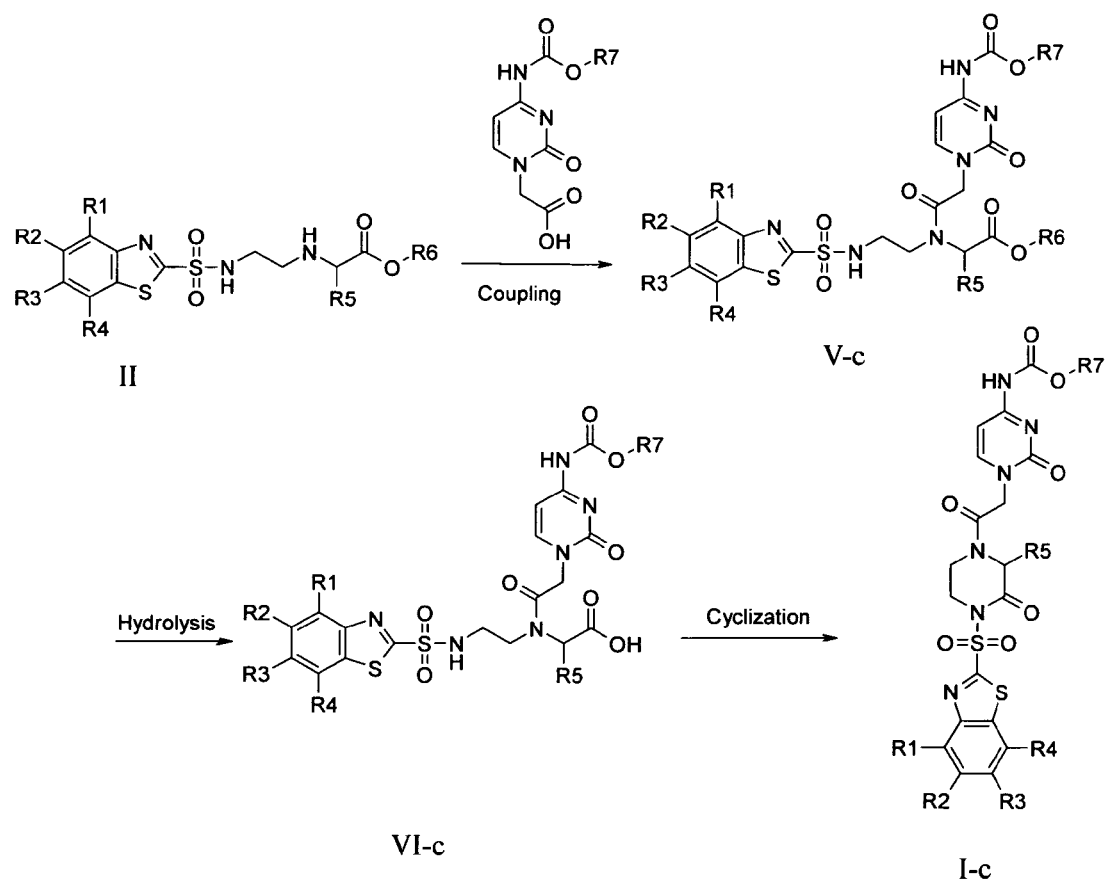
FIG. 10 shows a schematic representation of the synthesis of PNA cytosine monomer

With reference to FIG. 10, PNA C-monomer is prepared by coupling reaction of suitably protected (cytosin-1-yl)-acetic acids with a benzothiazole-2-sulfonyl, benzoxazole-2-sulfonyl, benzo[b]thiophene-2-sulfonyl or benzofuran-2-sulfonyl group protected backbone ester having general formula II in the presence of coupling reagent to afford the compound having general formula:

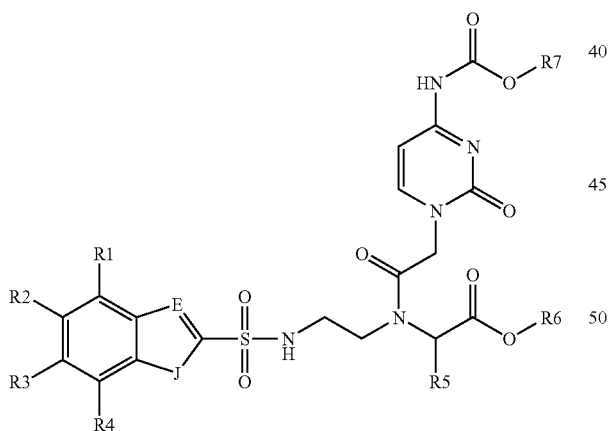

V-c

The entities represented by E, J, R1, R2, R3, R4, R5, R6, and R7 are as defined above. Preferably E is nitrogen, and J is sulfur.

The compounds having the general formula V-c are converted to corresponding acids by adding an excess of hydroxide ion source to obtain a compound having general formula VI-c:

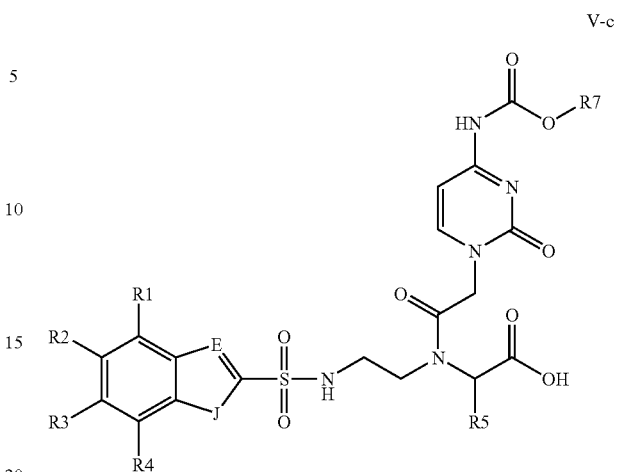

V-c

The entities represented by E, J, R1, R2, R3, R4, R5, and R7 are as defined above. Preferably E is nitrogen, and J is sulfur.

With reference to FIG. 10, the cyclization reaction of carboxylic acids produces PNA monomers having the general formula I-c by simultaneous reaction during activation of carboxylic acid. The activation of carboxylic acid may be conducted by general coupling reagent for peptide synthesis or mixed anhydride. The reaction conditions and reagents are the same as described above.

Figure 11:
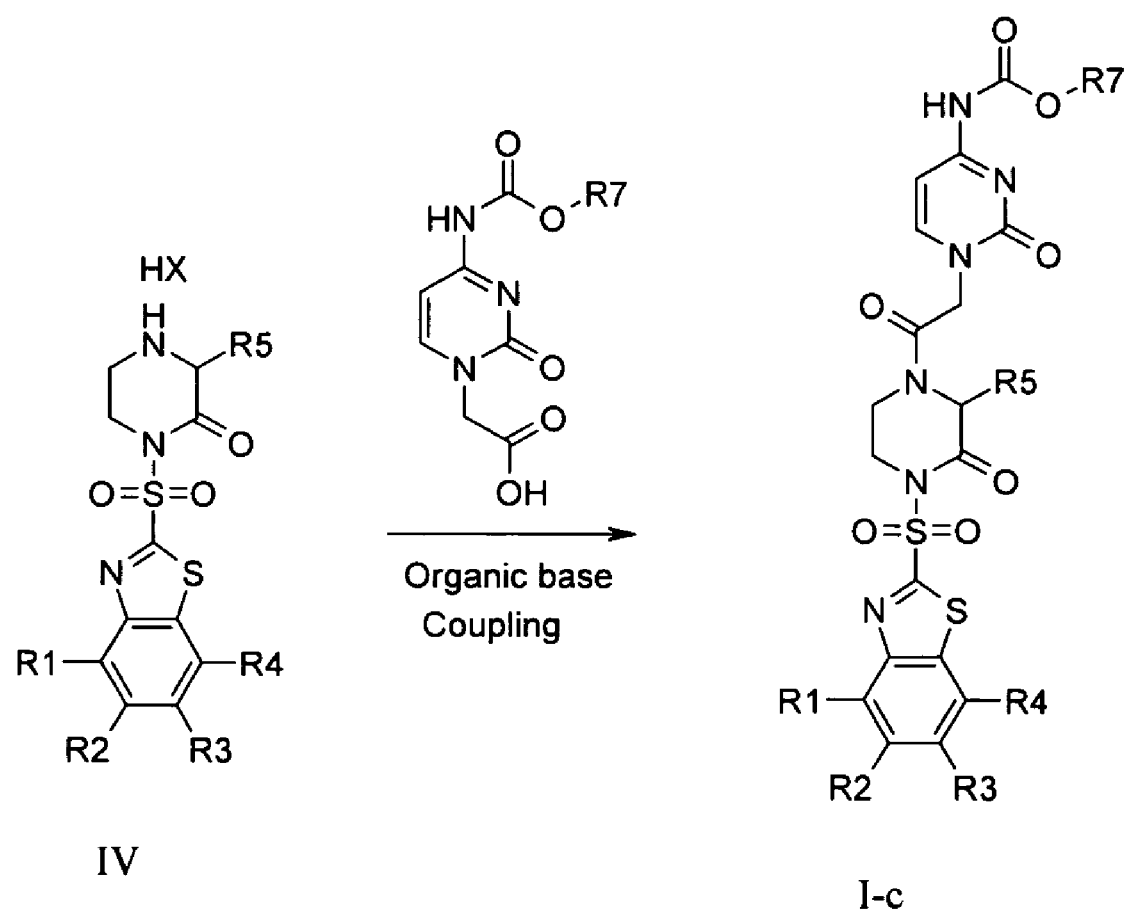
FIG. 11 shows a schematic representation of the alternative synthesis of PNA cytosine monomer.

Alternatively, as seen in FIG. 11, PNA C-monomer can be prepared by coupling suitably protected (cytosin-1-yl)-acetic acids to piperazinone derivatives having general formula IV. The reaction conditions and reagents are the same as described above.

Synthesis of A-monomer

A-monomer is a compound having general formula I-a:

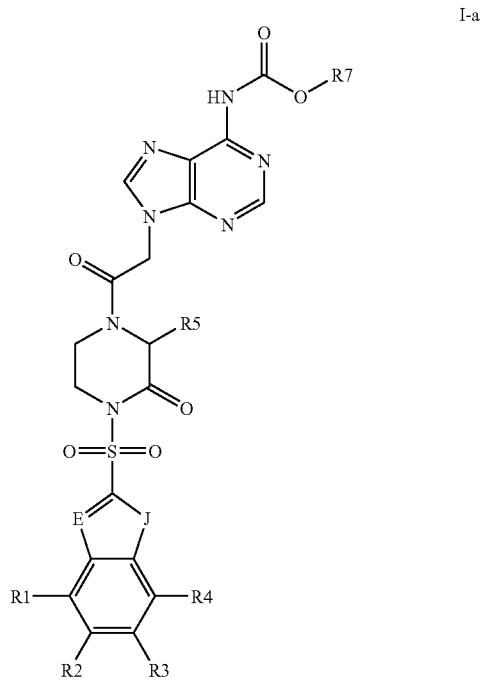

I-a

The entities represented by E, J, R1, R2, R3, R4, R5, and R7 are as defined above. Preferably E is nitrogen, and J is sulfur.

The precursors for PNA A-monomers, suitably protected (adenin-9-yl)-acetic acids (shown below), are prepared by the method according to the scheme as depicted in FIG. 7 and known methods such as described in U.S. Pat. No. 6,133,444; and S. A. Thomson et al., *Tetrahedron*, 1995, 6179-6194, which are incorporated by reference herein in their entirety, or modifications thereof.

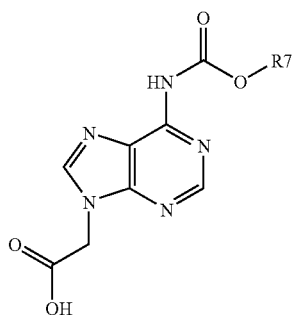

R7 is selected from methyl, ethyl, benzyl, benzhydryl, 4-methoxybenzyl, 3,4-dimethoxybenzyl, piperonyl derivatives, and 2-methylthioethyl group.

Figure 12:
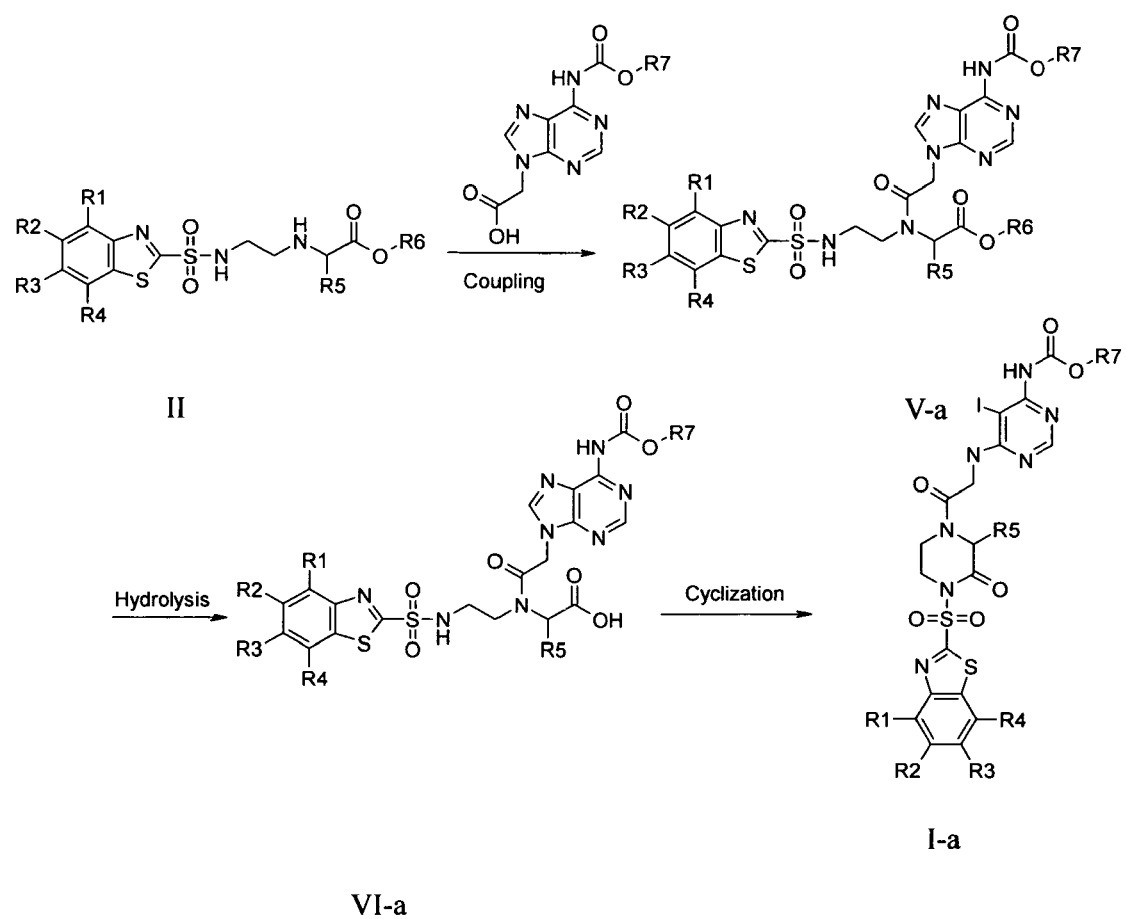
FIG. 12 shows a schematic representation of the synthesis of PNA adenine monomer.

With reference to FIG. 12, PNA C-monomer is prepared by coupling reaction of suitably protected (adenin-9-yl)-acetic acids with a benzothiazole-2-sulfonyl, benzoxazole-2-sulfonyl, benzo[b]thiophene-2-sulfonyl or benzofuran-2-sulfonyl group protected backbone ester having, general formula II in the presence of coupling reagent to obtain the compound having general formula V-a:

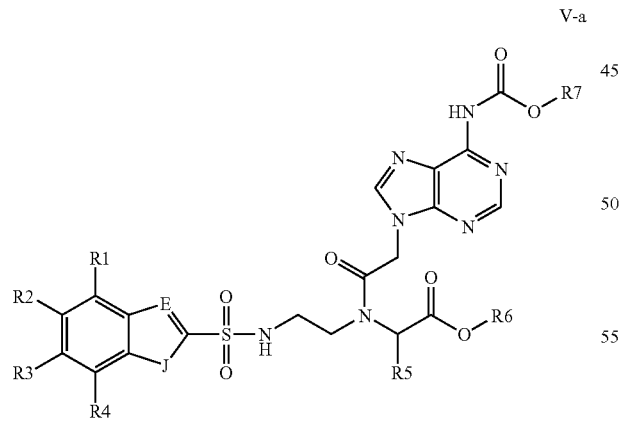

The entities represented by E, J, R1, R2, R3, R4, R5, R6, and R7 are as defined above. Preferably E is nitrogen, and J is sulfur.

The compounds having the general formula V-a are converted to corresponding acids by adding an excess hydroxide ion source to afford the compound having general formula VI-a:

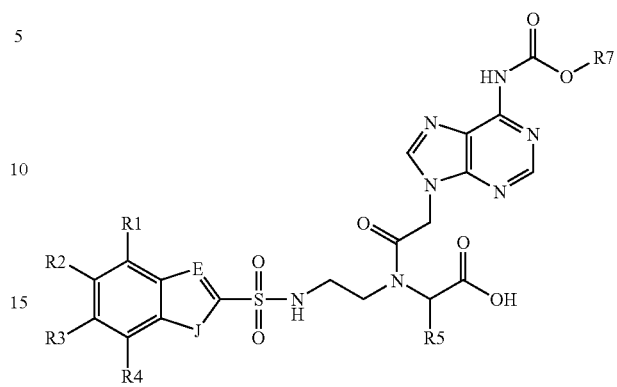

The entities represented by E, J, R1, R2, R3, R4, R5, and R7 are as defined above. Preferably E is nitrogen, and J is sulfur.

With reference to FIG. 12, the cyclization reaction of carboxylic acids produces PNA monomers having the general formula I-a by simultaneous reaction during activation of carboxylic acid. The activation of carboxylic acid can be conducted by general coupling reagent for peptide synthesis or mixed anhydride. The reaction conditions and reagents are the same as described above.

Figure 13:
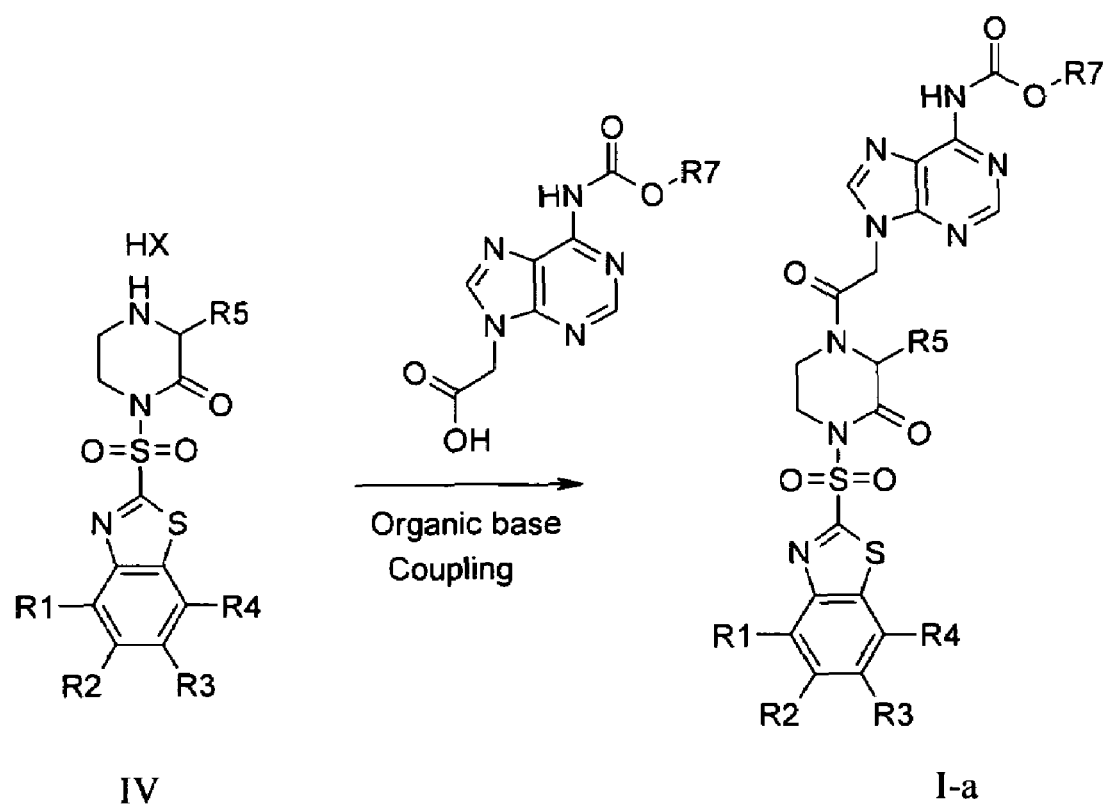
FIG. 13 shows a schematic representation of the alternative synthesis of PNA adenine monomer.

Alternatively, as seen in FIG. 13, PNA A-monomer can be prepared by coupling suitably protected (adenin-9-yl)-acetic acids to piperazinone derivatives having general formula IV. The reaction conditions and reagents are the same as described above.

Synthesis of G-monomer

G-monomer is a compound having general formula I-g:

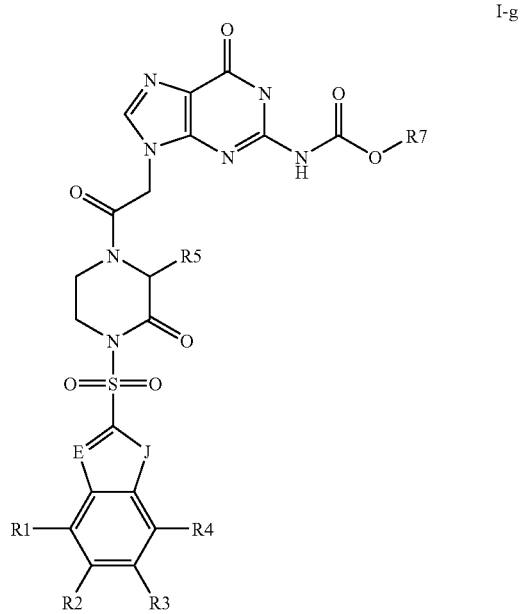

The entities represented by E, J, R1, R2, R3, R4, R5, and R7 are as defined above. Preferably E is nitrogen, and J is sulfur.

The precursors for PNA G-monomers, suitably protected (guanin-9-yl)-acetic acids, (shown below), are prepared by the method according to the scheme depicted in FIG. 7 and known methods such as described in U.S. Pat. No. 6,172,226, or modifications thereof.

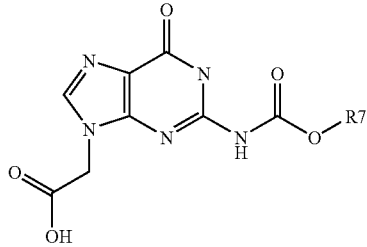

R7 may be methyl, ethyl, benzyl, benzhydryl, 4-methoxybenzyl, 3,4-dimethoxybenzyl, piperonyl derivatives, or 2-methylthioethyl group.

Figure 14:
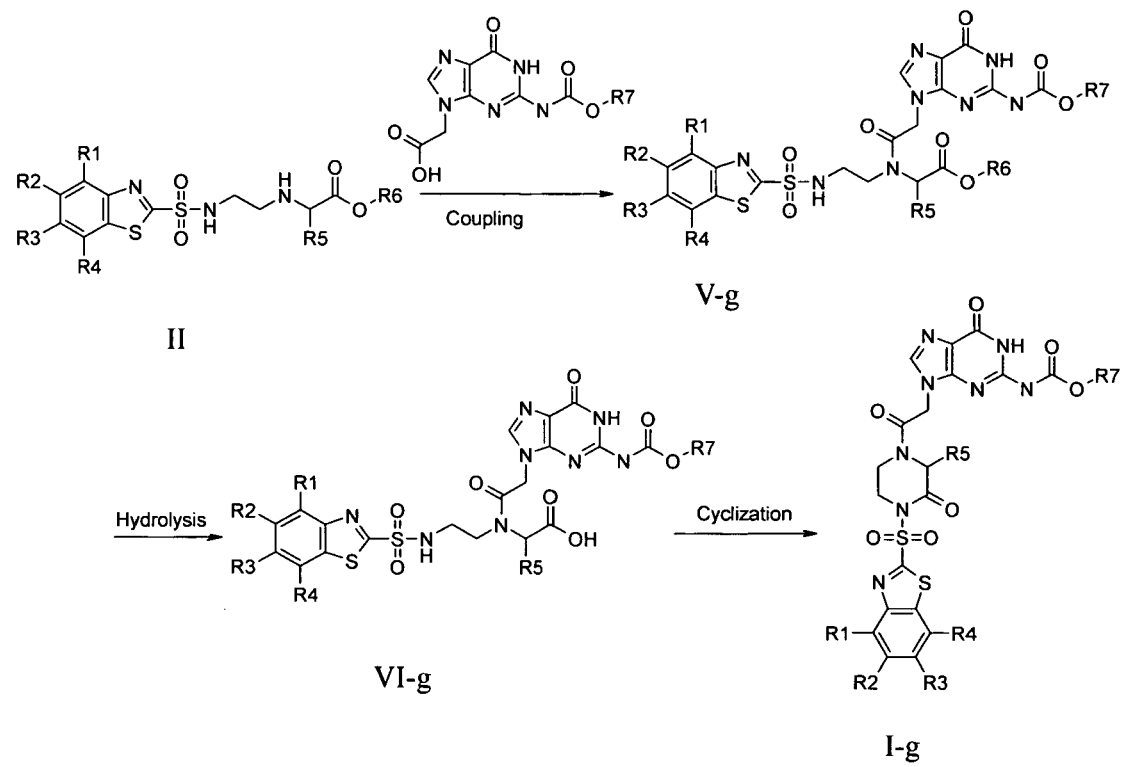
FIG. 14 shows a schematic representation of the synthesis of PNA guanine monomer.

With reference to FIG. 14, PNA G-monomer is prepared by coupling reaction of suitably protected (guanin-9-yl)-acetic acids with a benzothiazole-2-sulfonyl, benzoxazole-2-sulfonyl, benzo[b]thiophene-2-sulfonyl or benzofuran-2-sulfonyl group protected backbone ester having general formula II in the presence of coupling reagent to afford the compound having general formula V-g:

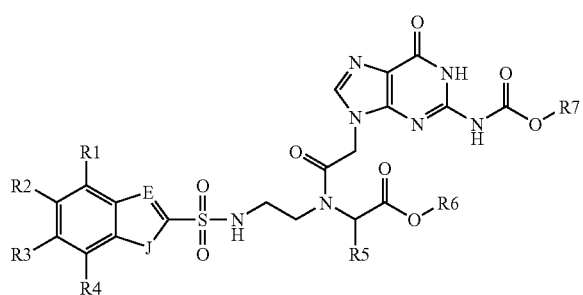

The entities represented by E, J, R1, R2, R3, R4, R5, R6, and R7 are as defined above. Preferably E is nitrogen, and J is sulfur.

The compounds having the general formula V-g are converted to corresponding acids by adding an excess hydroxide ion source to afford the compound having general formula VI-g:

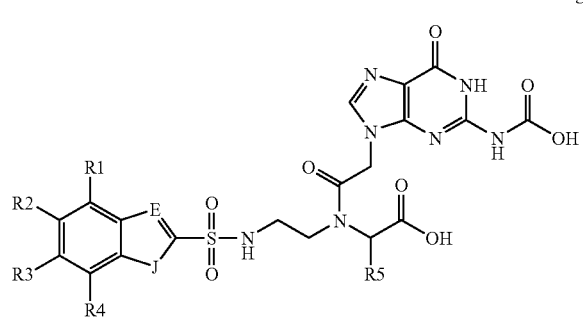

The entities represented by E, J, R1, R2, R3, R4, R5, and R7 are as defined above. Preferably E is nitrogen, and J is sulfur.

With reference to FIG. 14, the cyclization reaction of carboxylic acids produces PNA monomers having the general formula I-g by simultaneous reaction during activation of carboxylic acid. The activation of carboxylic acid can be conducted by general coupling reagent for peptide synthesis or mixed anhydride. The reaction conditions and reagents are the same as described above.

Figure 15:
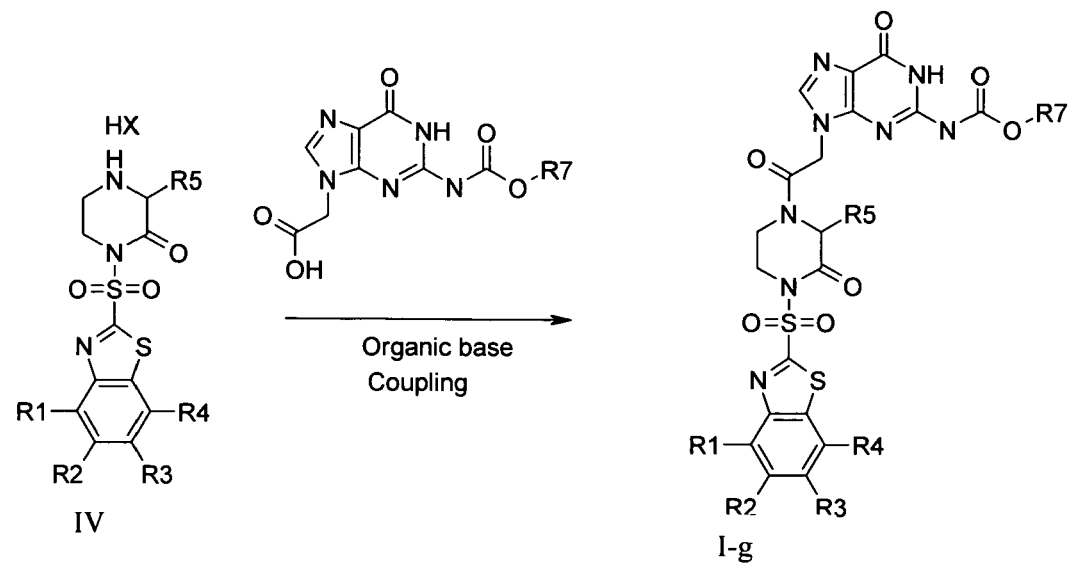
FIG. 15 shows a schematic representation of the alternative synthesis of PNA guanine monomer.
Figure 16:
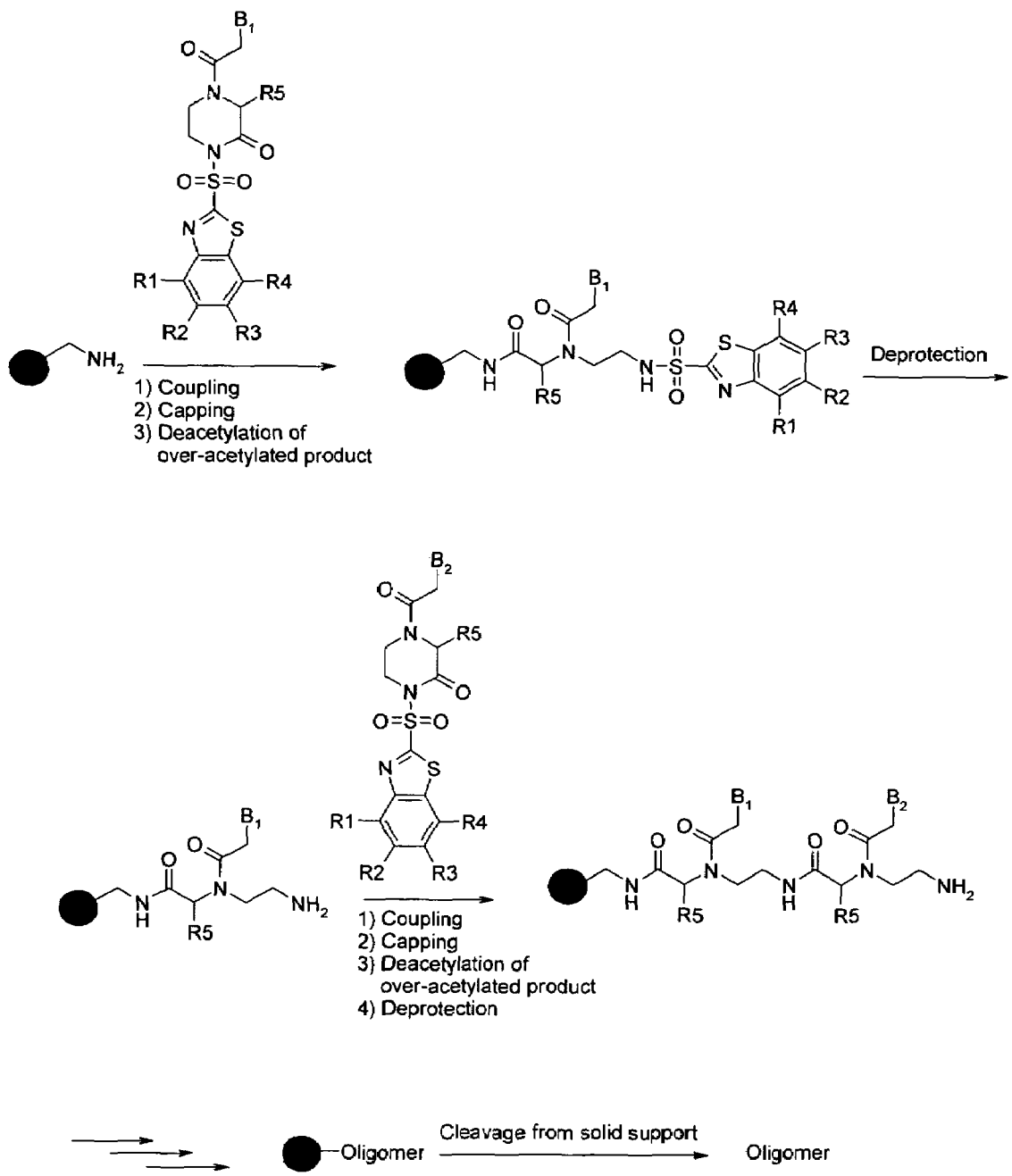
FIG. 16 shows a schematic representation of the PNA oligomer synthesis from PNA monomers.

Alternatively, as seen in FIG. 15, PNA G-monomer can be prepared by coupling suitably protected (guanin-9-yl)-acetic acids to piperazinone derivatives having general formula IV. The reaction conditions and reagents are the same as described above.

Synthesis of PNA oligomers

Various combinatorial synthetic methods already reported in chemical literature are generally applicable to PNA oligomer synthesis using the monomers of this invention. These methods include, but are not limited to, solid phase synthesis and solution phase synthesis. After the PNA monomers have been synthesized in the manner described above, PNA oligomers are constructed by solid phase synthesis on a suitable support material such as, but not limited to, polystyrene, polyoxyethylene-modified polystyrene, such as, for example Tentagel® or Controlled Pore Glass, which is provided with anchoring group which latently contains cleavable amine functional group. In solid phase synthesis, the first PNA monomer of this invention is incorporated by coupling reaction to solid support. The next step is systematic elaboration of desired PNA oligomer sequence. This elaboration includes repeated deprotection/coupling/capping cycles. The backbone protecting group on the last coupled monomer, benzothiazole-2-sulfonyl, benzoxazole-2-sulfonyl, benzo[b]thiophene-2-sulfonyl or benzofuran-2-sulfonyl group, is quantitatively removed by treatment with suitable thiol in the presence of organic base to liberate terminal free amine. Once the synthesis of PNA oligomer has been completed, the oligomers are cleaved from the solid support and nucleobase protecting groups are simultaneously removed by incubation for 1-2 h. at about room temperature in TFA containing cresol as a cation scavenger.

Following is an example of a general reaction cycle that may be used for the synthesis of PNA oligomers, and is not meant to limit the invention in any way, such as in the sequence of steps, since any oligomer synthesis method may be generally used so long as the inventive PNA monomer is employed.

1. Removing protecting group from resin to activate amine functional group.
2. Incorporating amino-acid, linker, or PNA monomer having terminal protected amine group to resin.
3. Washing.
4. Capping with acetic anhydride in the presence of organic base.
5. Washing.
6. Cleavage over reacted acetyl group in sulfonamide.
7. Washing.
8. Deprotecting sulfonyl group.
9. Washing.
10. Adding monomer.
11. Returning to No. 3 and repeating No. 4-No. 11.

In the course of the coupling reaction of monomer for the oligomer synthesis reaction, the acylating reaction can be accelerated by using a catalyst such as but not limited to mercury acetate, tetramethylammonium fluoride, tetraethylammonium fluoride, tetrabutylammonium fluoride, benzyltrimethylammonium fluoride, cesium fluoride, tributylphosphine, triphenylphosphine. Preferred catalyst is tetrabutylammonium fluoride. Also, the reaction rate depends on the solvent used and reaction temperature. Examples of solvents include, but are not limited to, DMF, N-methylpyrrolidone, dimethoxyethane, dichloromethane, 1,2-dichloroethane, DMSO, tetrahydrofuran, hexamethylphophoramide, tetramethylene sulfone, isopropyl alcohol, ethyl alcohol, and mixture of selected solvents. Preferred solvent is DMF. The N-terminal amino protecting group is cleaved by using thiol with organic base in solvent. Examples of thiols include, but are not limited to, $C_2$~$C_{20}$ alkanethiol, 4-methoxytoluenethiol, 4-methylbenzenethiol, 3,6-dioxa-1,8-octanethiol, 4-chlorotoluenethiol, benzylmercaptane, N-acetylcysteine, N-(t-Boc)cysteine methyl ester, methyl 3-mercaptopropionate, 4-methoxybenzene thiol. Examples of organic bases include, but are not limited to, triethylamine, N,N-diisopropyethylamine, piperidine, N-methylmorpholine, and 1,8-diazabicyclo[5,4,0]undec-7-one. Preferred organic base is N,N-diisopropyethylamine.

List of Abbreviations.

t-Boc tert-Butyloxycarbonyl

AOP O-(7-azabenzotriazol-1-yl)-tris(dimethylamino)phosphonium

BBC 1-benzotriazol-1-yloxy-bis(pyrrolidino)uronium hexafluorophosphate

BDMP 5-(1H-benzotriazol-1-yloxy)-3,4-dihydro-1-methyl 2H-pyrrolium hexachloroanitimonate BDP benzotriazol-1-yl diethyl phosphate BEMT 2-bromo-3-ethyl-4-methyl thiazolium tetrafluoroborate BTFFH bis(tetramethylenefluoroformamidinium) hexafluorophosphate BOMI benzotriazol-1-yloxy-N,N-dimethylmethaniminium hexachloroantimonate BOI 2-(benzotriazol-1-yl)oxy-1,3-dimethyl-imidazolinium hexafluorophosphate BOP benzotriazolyl-1-oxy-tris(dimethylamino)phophonium hexafluorophosphate BOP-Cl bis(2-oxo-3-oxazolidinyl)phosphinic chloride BroP bromotris(dimethylamino)phophonium hexafluorophosphate CDI carbonyldiimidazole CIP 2-chloro-1,3-dimethylimidazolidinium hexafluorophosphate DMF dimethylformamide DCC 1,3-dicyclohexylcarbodiimide DEPBT 3-(diethoxyphosphoryloxy)-1,2,3-benzotriazin-4(3H)-one Dpp-Cl diphenylphosphinic chloride EDCI 1-ethyl-3-(3'-dimethylaminopropyl)carbodiimide hydrochloride EEDQ 2-ethoxy-1-ethoxycarbonyl-1,2-dihydroquinoline Fmoc 9-fluorenylmethyloxycarbonyl FDPP pentafluorophenyl diphenylphosphinate HAPyU O-(7-azabenzotriazol-1-yl)-1,1,3,3-bis(tetramethylene)uranium hexafluorophosphate HATU O-(7-azabenzotriazol-1-yl)-1,1,3,3-tetramethyluranium hexafluorophosphate HBTU O-(benzotriazol-1-yl)-1,1,3,3-tetramethyluranium hexafluorophosphate HOBt hydroxybenzotriazole HOAt 1-hydroxy-7-azabenzotriazole HODhbt 3-hydroxy-3,4-dihydro-4-oxo-1,2,3-benzotriazine HOSu hydroxysuccinimide HOTT S-(1-oxido-2-pyridinyl)-1,1,3,3-tetramethylthiouronium hexafluorophosphate MSNT 2,4,6-mesitylenesulfonyl-3-nitro-1,2,4-triazolide Mmt 4-methoxyphenyldiphenylmethyl NEPIS N-ethyl-5-phenylisoxazolium-3'-sulfonate PyAOP 7-azobenzotriazolyoxytris(pyrrolidino)phosphonium hexafluorophosphate PyBOP benzotriazolyl-1-oxy-tripyrrolidinophosphonium hexafluorophosphate PyBroP bromotripyrrolidinophosphonium hexafluorophosphate PyCloP chlorotris(pyrrolydino)phophonium hexafluorophosphate TAPipU O-(7-azabenzotriazol-1-yl)-1,1,3,3-bis(pentamethylene)uranium tetrafluoroborate TBTU O-(benzotriazol-1-yl)-1,1,3,3-tetramethyluranium tetrafluoroborate TDO 2,5-diphenyl-2,3-dihydro-3-oxo-4-hydroxythiophene dioxide TFA trifluoroacetic acid TFFH tetramethylfluoroformamidinium hexafluorophosphate TOTT S-(1-oxido-2-pyridinyl)-1,1,3,3-tetramethylthiouronium tetrafluoroborate TDBTU 2-(3,4-dihydro-4-oxo-1,2,3-benzotriazin-3-yl)-1,1,3,3-tetramethyluronium tetrafluoroborate TNTU O-[(5-norbonene-2,3-dicarboximido)-1,1,3,3-tetramethyluronium tetrafluoroborate TOTU O-[(cyano(ethoxycarbonyl)methylene)amino]-1,1,3,3-tetramethyluronium tetrafluoroborate TPTU O-(1,2-dihydro-2-oxo-1-pyridyl-1,1,3,3-tetramethyluronium tetrafluoroborate TSTU O-(N-succinimidyl)-1,1,3,3-tetramethyluronium tetrafluoroborate This invention is more specifically illustrated by following Examples, which are not meant limit the invention, unless otherwise noted.

EXAMPLES

Example 1

N-[2-(Benzothiazole-2-sulfonylamino)-ethyl]-glycine ethyl ester

To a solution of N-(2-aminoethyl)-glycine ethyl ester 2HCl (1.10 g, 5.0 mmol), prepared as described by Will (D. W. Will et al., *Tetrahedron*, 1995, 51, 12069.), in dichloromethane (50 mL) was slowly added triethylamine (2.02 g, 20 mmol) at room temperature. Then benzothiazole-2-sulfonyl chloride (1.19 g 5.0 mmol) in dichloromethane (10 mL) was added to the reaction mixture at room temperature for 5 min. The resulting reaction mixture was stirred for additional 2 h. at room temperature and washed with water (30 mL). The organic layer was dried over $MgSO_4$ and filtered. The filtrate was evaporated to remove solvent to give desired product (1.60 g, 92%) as a solid. $^1$H NMR (500 MHz; DMSO-$d_6$) δ 8.28 (d, 1H), 8.19 (d, 1H), 7.69~7.63 (m, 2H), 4.03 (q, 2H), 3.24 (s, 2H), 3.13 (t, 2H), 2.62 (t, 2H), 1.15 (t, 3H).

Example 2

[2-(5-Chloro-benzothiazole-2-sulfonylamino)-ethyl]-glycine ethyl ester

The title compound (657 mg, 87%) was synthesized by the reaction of N-(2-aminoethyl)-glycine ethyl ester 2HCl (398 mg, 2.0 mmol) with 5-chloro-benzothiazole-2-sulfonyl chloride (536 mg, 2.0 mmol) as per the procedure of example 1. $^1$H NMR (500 MHz; DMSO-$d_6$) δ 8.32 (d, 1H), 8.31 (s, 1H), 7.71 (d, 1H), 4.02 (q, 2H), 3.25 (s, 2H), 3.14 (t, 2H), 2.62 (t, 2H), 1.15 (t, 3H).

Example 3

[2-(4-Chloro-5-methoxy benzothiazole-2-sulfonylamino)-ethyl]-glycine ethyl ester The title compound (726 mg, 89%) was synthesized by the reaction of N-(2-aminoethyl)-glycine ethyl ester 2HCl (398 mg, 2.0 mmol) with 4-chloro-5-methoxy-benzothiazole-2-sulfonyl chloride (596 mg, 2.0 mmol) as per the procedure of Example 1. $^1$H NMR (500 MHz; DMSO-$d_6$) δ 8.18 (d, 1H), 7.57 (d, 1H), 4.00 (q, 2H), 3.97 (s, 3H), 3.22 (s, 2H), 3.14 (t, 2H), 2.62 (t, 2H), 1.13 (t, 3H).

Example 4

N-[2-(Benzothiazole-2-sulfonylamino)-ethyl]-alanine ethyl ester

N-(2-Aminoethyl)-alanine ethylester 2HCl, prepared as described by Puschl (A. Puschl et al., *Tetrahedron*, 1998, 39, 4707.), was reacted with benzothiazole-2-sulfonyl chloride as per the procedure of Example 1 to give the title compound. $^1$H NMR (500 MHz; DMSO-$d_6$) δ 8.27 (d, 1H), 8.18 (d, 1H), 7.69~7.62 (m, 2H), 4.01 (q, 2H), 3.17 (q, 1H), 3.13 (t, 2H), 2.61 (m, 1H), 2.49 (m; 1H), 1.13 (t, 3H), 1.06 (d, 3H).

Example 5

N-[2-(Benzothiazole-2-sulfonylamino)-ethyl]-N-(tert-butoxycarbonyl)-glycine

To a solution of N-[2-(benzothiazole-2-sulfonylamino)-ethyl]-glycine ethyl ester (6.87 g, 20 mmol) in tetrahydrofuran (50 mL) was added a solution of LiOH (1.64 g, 40 mmol) dissolved in water (30 mL). After stirring for 1 hour at room temperature, di-t-butyl dicarbonate (6.55 g, 30 mmol) was added to the reaction mixture. The resulting reaction mixture was stirred for 30 min. and then a solution of LiOH (0.82 g, 0.02 mol) in water (15 mL) was added. After completion of the reaction by TLC, the precipitate was removed by filtration and tetrahydrofuran was removed in vacuo. The residual solution was washed with ethyl ether (100 mL). The aqueous layer was acidified to pH 3 by adding 2N HCl and extracted with dichloromethane (100 mL). The organic layer was dried over MgSO$_4$ and filtered. The filtrate was concentrated in vacuo to afford the desired product (7.88 g, 95%). $^1$H NMR (500 MHz; DMSO-$d_6$) δ 8.73 (d, 1H), 8.19 (dd, 1H), 7.71~7.63 (m, 2H), 3.84 (s, 1H), 3.79 (s, 1H), 3.30~3.22 (m, 4H), 1.34 (s, 4.5H), 1.28 (s, 4.5H).

Example 6

N-[2-(5-Chloro-benzothiazole-2-sulfonylamino)-ethyl]-N-(tert-butoxycarbonyl)-glycine The title compound (607 mg, 90%) was synthesized from N-[2-(5-chloro-benzothiazole-2-sulfonylamino)-ethyl]-glycine ethyl ester (567 g, 1.5 mmol) as per the procedure of Example 5. $^1$H NMR (500 MHz; DMSO-$d_6$) δ 8.80 (br, 1H), 8.33 (d, 1H), 8.32 (s, 1H), 7.72 (d, 1H), 3.84 (s, 1H), 3.80 (s, 1H), 3.29 (m, 2H), 3.23 (m, 2H), 1.35 (s, 4.5H), 1.28 (s, 4.5H).

Example 7

N-[2-(4-Chloro-5-methoxy-benzothiazole-2-sulfonylamino)-ethyl]-N-(tert-butoxycarbonyl)-glycine The title compound (655 mg, 91%) was synthesized from N-[2-(4-chloro-5-methoxy-benzothiazole-2-sulfonylamino)-ethyl]-glycine ethyl ester (612 g, 1.5 mmol) as per the procedure of Example 5. $^1$H NMR (500 MHz; DMSO-$d_6$) δ 8.83 (br, 1H), 8.20 (d, 1H), 7.58 (d, 1H), 3.98 (s, 3H), 3.83 (s, 1H), 3.79 (s, 1H), 3.32-3.23 (m, 4H), 1.34 (s, 4.5H), 1.25 (s, 4.5H).

Example 8

N-[2-(Benzothiazole-2-sulfonylamino)-ethyl]-N-(tert-butoxycarbonyl)-alanine

The title compound was synthesized from N-[2-(benzothiazole-2-sulfonylamino)-ethyl]-alanine ethyl ester as per the procedure of Example 5. $^1$H NMR (500 MHz; DMSO-$d_6$) δ 8.85 (brs, 1H), 8.28 (d, 1H), 8.18 (dd, 1H), 7.71~7.64 (my 2H), 4.33 (q, 0.5H), 4.07 (q, 1H), 3.34~3.15 (m, 4H), 1.34 (s, 4.5H), 1.32 (s, 4.5H), 1.29 (d, 2H).

Example 9

1-(Benzothiazole-2-sulfonyl)-piperazin-2-one trifluoroacetic acid salt

To a solution of N-[2-(benzothiazole-2-sulfonylamino)-ethyl]-N-(tert-butoxycarbonyl)-glycine (8.30 g, 20 mmol) in dichloromethane (100 mL) was added dicyclohexyl carbodiimide (5.16 g, 25 mmol). After stirring for 2 hours at room temperature, the precipitate was removed by filtration. The filtrate was concentrated to approximately 30 mL and cooled to 0° C. To a cold solution was added trifluoroacetic acid (20 mL). The mixture was stirred for 2 h at the same temperature and ethyl ether (100 mL) was slowly added. The precipitate product was filtered off, washed with ethyl ether, and dried in vacuo to afford white solid (6.58 g, 80%). $^1$H-NMR (500 MHz DMSO-$d_6$) δ 8.36 (m, 1H), 8.25 (m, 1H), 7.76~7.70 (m, 2H), 4.17 (t, 2H), 3.96 (s, 2H), 3.56 (t, 2H).

Example 10

1-(5-Chloro-benzothiazole-2-sulfonyl)-piperazin-2-one trifluoroacetic acid salt

The title compound (342 mg, 78%) was synthesized from N-[2-(5-chloro-benzothiazole-2-sulfonylamino)-ethyl]-N-(tert-butoxycarbonyl)-glycine (540 mg, 1.2 mmol) as per the procedure of Example 9. $^1$H-NMR (500 MHz; DMSO-$d_6$) δ 9.55 (br, 2H), 8.40 (d, 1H), 8.39 (d, 1H), 7.79 (dd, 1H), 4.16 (t, 2H), 3.97 (s, 2H), 3.57 (t, 2H).

Example 11

1-(4-Chloro-5-methoxy-benzothiazole-2-sulfonyl)-piperazin-2-one trifluoroacetic acid salt The title compound (389 mg, 82%) was synthesized from N-[2-(4-chloro-5-methoxy-benzothiazole-2-sulfonylamino)-ethyl]-N-(tert-butoxycarbonyl)-glycine (576 mg, 1.2 mmol) as per the procedure of Example 9. $^1$H-NMR (500 MHz; DMSO-$d_6$) δ 8.28 (d, 1H), 7.68 (d, 1H), 4.16 (dd, 2H), 3.99 (s, 3H), 3.96 (s, 2H), 3.56 (dd, 2H).

Example 12

1-(Benzothiazole-2-sulfonyl)-3-methyl-piperazin-2-one trifluoroacetic acid salt The title compound was synthesized from N-[2-(benzothiazole-2-sulfonylamino)-ethyl]-N-(tert-butoxycarbonyl)-alanine as per the procedure of Example 9. $^1$H-NMR (500 MHz; DMSO-d$_6$) δ 9.80 (brs, 2H), 8.35 (m, 1H), 8.25 (m, 1H), 7.75~7.70 (m, 2H), 4.31~4.25 (m, 2H), 4.17 (m, 1H), 3.70 (m, 1H), 3.55 (m, 1H), 1.34 (d, 3H).

Example 13

[4-N-(Piperonyloxycarbonyl)-cytosin-1-yl]-acetic acid ethyl ester

The reaction mixture of (cytosin-1-yl)-acetic acid (3.94 g, 20 mmol) and 1,1'-carbonyldiimidazole (4.86 g, 30 mmol) in DMF was stirred for 25 min. at 100° C. Then, piperonyl alcohol (6.08 g, 40 mmol) was added to the reaction mixture. The resulting reaction mixture was allowed to cool to room temperature for 2 h. The solvent was removed in vacuo and the residue was dissolved in ethyl acetate (100 mL). The solution was washed with water (100 mL×2), dried over MgSO$_4$, and filtered. The filtrate was concentrated in vacuo and treated with ethyl ether to afford white solid. The solid was filtered off and dried in vacuo to give the desired product (7.20 g, 96%). $^1$H-NMR (500 MHz; DMSO-d$_6$) δ 10.77 (s, 1H), 8.04 (d, 1H), 7.04 (d, 1H), 7.00 (s, 1H), 6.92 (s, 2H), 6.02 (s, 2H), 5.09 (s, 2H), 4.61 (s, 2H), 4.15 (q, 2H), 1.19 (t, 3H).

Example 14

[6-N-(Piperonyloxycarbonyl)-adenin-9-yl]-acetic acid ethyl ester

The title compound (6.8 g, 85%) was synthesized from (adenin-9-yl)-acetic acid ethyl ester (4.42 g, 20 mmol) as per the procedure of Example 13. $^1$H-NMR (500 MHz; DMSO-d$_6$) δ 10.65 (s, 1H), 8.62 (s, 1H), 8.44 (s, 1H), 7.05 (s, 1H), 6.95 (d, 1H), 6.92 (d, 1H), 6.03 (s, 2H), 5.20 (s, 2H), 5.12 (s, 2H), 4.18 (q, 2H), 1.22 (t, 3H).

Example 15

(2-Amino-6-iodopurin-9-yl)-acetic acid ethyl ester

To a solution of 2-amino-6-iodo-purine (78.3 g, 0.3 mol) in DMF (1960 mL) was added ethyl bromoacetate (55.1 g, 0.33 mol) and potassium carbonate (82.9 g, 0.6 mol). The resulting reaction mixture was stirred for 12 h at room temperature. The reaction mixture was concentrated to small volume (about 150 mL) in vacuo and the residue was dissolved in water. The solid was filtered off, washed with water and ethyl ether, and dried in vacuo to give the titled compound (98.4 g, 95%). $^1$H-NMR (500 MHz; DMSO-d$_6$) δ 8.06 (s, 1H), 6.90 (br.s, 2H), 4.94 (s, 2H), 4.17 (q, 2H), 1.22 (t, 3H).

Example 16

[2-(Piperonyloxycarbonyl)-amino-6-iodopurine-9-yl]-acetic acid ethyl ester

To a solution of (2-amino-6-iodopurine-9-yl)-acetic acid ethyl ester (3.47 g, 10 mmol) in tetrahydrofuran (40 mL) was added triphosgene (1.20 g, 4 mmol) at 0° C. After stirring for additional 30 min, N,N-diisopropylethylamine (3.30 g) was slowly added and the reaction mixture was stirred for 30 min at 0° C. Then, piperonyl alcohol (2.30 g, 15 mmol) was added and the resulting reaction mixture was allowed to warm to room temperature and stirred for additional 1.5 h. To the resulting mixture was added water (50 mL) and ethyl alcohol (50 mL). The solution was concentrated to about 100 mL to precipitate solid. The solid was filtered off, washed with ethyl alcohol, and dried in vacuo to give the desired product (2.40 g, 46%). $^1$H NMR (500 MHz; DMSO-d$_6$) δ 10.77 (s, 0.5H), 10.69 (s, 0.5H), 8.49 (s, 0.5H), 8.45 (s, 0.5H), 7.01 (s, 1H); 6.94 (d, 1H), 6.91 (d, 1H), 6.02 (s, 2H), 5.11 (s, 1H), 5.07 (s, 2H), 5.06 (s, 1H).

Example 17

[4-N-(Piperonyloxycarbonyl)-cytosin-1-yl]-acetic acid

To a suspension of [4-N-(piperonyloxycarbonyl)-cytosin-1-yl]-acetic acid ethyl ester (6.40 g, 17 mmol) in tetrahydrofuran (30 mL) and water (60 mL) was added lithium hydroxide monohydrate (1.6 g) at room temperature. After stirring 20 min, the reaction mixture was acidified by adding 1 N HCl (40 mL). The precipitated solid was filtered off, washed with water (20 mL) and ethyl alcohol (20 mL), and dried in vacuo to give the desired product (5.8 g, 98%). $^1$H-NMR (500 MHz; DMSO-d$_6$) δ 7.94 (d, 1H), 6.93 (d, 1H), 6.90 (s, 1H), 6.82 (s, 2H), 5.93 (s, 2H), 4.99 (s, 2H), 4.43 (s, 2H).

Example 18

[6-N-(Piperonyloxycarbonyl)-adenin-9-yl]-acetic acid

The title compound (3.67 g, 99%) was synthesized from [6-N-(piperonyloxycarbonyl)-adenin-9-yl]-acetic acid ethyl ester (4.00 g, 10 mmol) as per the procedure of Example 17. $^1$H NMR (500 MHz; DMSO-d$_6$) δ 10.53 (s, 1H), 8.52 (s, 1H), 8.33 (s, 1H), 6.96 (s, 1H), 6.86 (d, 1H), 6.82 (d, 1H), 5.93 (s, 2H), 5.02 (s, 2H), 4.99 (s, 2H).

Example 19

[2-N-(Piperonyloxycarbonyl)-guanin-9-yl]-acetic acid

To a suspension of 60% NaH (1.3 g, 32.5 mmol) in tetrahydrofuran (40 mL) was slowly added 3-hydroxypropionitrile (2.3 g, 29.5 mmol) for a period of 20 min. at 0° C. and the mixture was stirred for additional 30 min. To the resulting reaction mixture was slowly added [2-(piperonyloxycarbonyl)-amino-6-iodo-purine-9-yl]-acetic acid ethyl ester (2.4 g, 4.6 mmol) portion-wise in an ice bath. After the addition was completed, the ice bath was removed and stirring continued for additional 3 h. Then, water (20 mL) was added and stirred for additional 30 min. The reaction mixture was acidified to pH 3 by addition of 1 N HCl solution. After removal of tetrahydrofuran in vacuo, the solution was cooled in ice bath and the solid collected by filtration. The solid was washed with water (20 mL) and ethyl alcohol (20 mL) and dried in vacuo to give the desired product (1.4 g, 84%). $^1$H NMR (500 MHz; DMSO-$d_6$) δ 7.73 (s, 1H), 6.91 (s, 1H), 6.84 (d, 1H), 6.82 (d, 1H), 5.93 (s, 2H), 5.04 (s, 2H), 4.39 (s, 2H).

Example 20

N-[2-(Benzothiazole-2-sulfonylamino)-ethyl]-N-[(thymin-1-yl)-acetyl]-glycine ethyl ester To the mixture of N-[2-(benzothiazole-2-sulfonylamino)-ethyl]-glycine ethyl ester (1.72 g, 5 mmol), (thymin-1-yl)-acetic acid (0.92 g, 5 mmol), HOBt (0.81 g, 6 mmol), and DCC (1.24 g, 6 mmol) in DMF (15 mL) was added N,N-diisopropylethylamine (1.31 mL, 7.5 mmol) at ambient temperature. The resulting reaction mixture was stirred for 5 h at the same temperature and the solvent was removed in vacuo to 5 mL. The residue was dissolved in dichloromethane (50 mL) and the precipitate was filtered. The filtrate was washed with 1N HCl aqueous solution, saturated sodium bicarbonate solution, and brine. The organic layer was dried over magnesium sulfate and filtered. The filtrate was concentrated and the residue was triturated with ethyl alcohol. The resulting solid was filtered off and dried in vacuo to give the title compound (1.91 g, 75%) as a white solid. $^1$H NMR (500 MHz; DMSO-$d_6$) δ 11.29 (s, 0.6H), 11.28(s, 0.4H), 8.99(brs, 0.6H), 8.82(brs, 0.4H), 8.28(m, 1H) 8.18(d, 1H) 7.66(m, 2H) 7.31(s, 0.6H) 7.42(s, 0.4H) 4.66(s, 1.2H) 4.47(s, 0.8H) 4.31(s, 0.8H), 4.05(s, 1.2H), 4.04(q, 1.2H), 3.55(t, 1.2H), 3.40~3.34(m, 2.8H), 3.20(t, 0.8H), 1.73(s, 3H), 1.19(t, 1.2H), 1.14(t, 1.8H).

Example 21

N-[2-(Benzothiazole-2-sulfonylamino)-ethyl]-N-{[4-N-(benzhydryloxycarbonyl)-cytosin-1-yl]-acetyl}-glycine ethyl ester The title compound (2.99 g, 85%) was synthesized by the reaction of N-[2-(benzothiazole-2-sulfonylamino)-ethyl]-glycine ethyl ester (1.72 g, 5 mmol) and [4-N-(benzhydryloxycarbonyl)-cytosin-1-yl]-acetic acid (1.90 g, 5 mmol) as per the procedure of Example 20. $^1$H NMR (500 MHz; DMSO-$d_6$) δ 11.00 (s, 1H), 8.86 (brs, 1H), 8.27 (d, 1H), 8.18 (d, 1H), 7.89 (d, 0.6H), 7.83 (d, 0.4H), 7.68~7.61 (m, 2H), 7.45~7.26 (m, 10H), 6.94 (t, 1H), 6.79 (s, 1H), 4.81 (s, 1.2H), 4.62 (s, 0.8H), 4.35 (s, 0.8H), 4.13 (q, 0.8H), 4.06 (s, 1.2H), 4.03 (q, 1.2H), 3.59 (t, 1.2H), 3.44~3.39 (m, 2H), 3.21 (t, 0.8H), 1.19 (t, 1.2H), 1.13 (t, 1.8H).

Example 22

N-[2-(Benzothiazole-2-sulfonylamino)-ethyl]-N-{[4-N-(4-methoxybenzyloxycarbonyl)-cytosin-1-yl]-acetyl}-glycine ethyl ester The title compound (2.86 g, 87%) was synthesized by the reaction of N-[2-(benzothiazole-2-sulfonylamino)-ethyl]-glycine ethyl ester (1.72 g, 5 mmol) and [4-N-(4-methoxybenzyloxycarbonyl)-cytosin-1-yl]-acetic acid (1.67 g, 5 mmol) as per the procedure of Example 20. $^1$HNMR (500 MHz; DMSO-$d_6$) δ 10.71 (s, 1H), 8.26 (dd, 1H), 8.16 (dd, 1H), 7.90 (d, 0.6H), 7.82 (d, 0.4H), 7.68~7.60 (m, 2H), 7.34 (d, 2H), 7.00 (t, 1H), 6.93 (d, 2H), 5.10 (s, 2H), 4.82 (s, 1.2H), 4.61 (s, 0.8H), 4.34 (s, 0.8H), 4.13 (q, 0.8H), 4.05 (s, 1.2H), 4.03 (q, 1.2H), 3.74 (s, 3H), 3.56 (t, 1.2H), 3.40~3.30 (m, 2H), 3.19 (t, 0.8H), 1.19 (t, 1.2H), 1.12 (t, 1.8H).

Example 23

N-[2-(Benzothiazole-2-sulfonylamino)-ethyl]-N-{[4-N-(3,4-dimethoxybenzyloxycarbonyl)-cytosin-1-yl]-acetyl}-glycine ethyl ester The title compound (5.31 g, 81%) was synthesized by the reaction of N-[2-(benzothiazole-2-sulfonylamino)-ethyl]-glycine ethyl ester (3.26 g, 9.5 mmol) and [4-N-(3,4-dimethoxybenzyloxycarbonyl)-cytosin-1-yl]-acetic acid (3.28 g, 9.03 mmol) as per the procedure of Example 20. $^1$H NMR (500 MHz; DMSO-$d_6$) δ 10.72 (s, 1H), 8.27 (dd, 1H), 8.17 (dd, 1H), 7.90 (d, 0.6H), 7.82 (d, 0.4H), 7.69~7.62 (m, 2H), 7.02 (s, 1H), 7.00 (t, 1H), 6.94 (s, 2H), 5.09 (s, 2H), 4.80 (s, 1.2H), 4.61 (s, 0.8H), 4.34 (s, 0.8H), 4.13 (q, 0.8H), 4.05 (s, 1.2H), 4.03 (q, 1.2H), 3.75 (s, 3H), 3.74 (s, 3H), 3.58 (t, 1.2H), 3.42~3.37 (m, 2H), 3.20 (t, 0.8H), 1.20 (t, 1.2H), 1.14 (t, 1.8H).

Example 24

N-[2-(Benzothiazole-2-sulfonylamino)-ethyl]-N-{[4-N-(piperonyloxycarbonyl)-cytosin-1-yl]-acetyl}-glycine ethyl ester The title compound (2.89 g, 86%) was synthesized by the reaction of N-[2-(benzothiazole-2-sulfonylamino)-ethyl]-glycine ethyl ester (1.72 g, 5 mmol) and [4-N-(piperonyloxycarbonyl)-cytosin-1-yl]-acetic acid (1.74 g, 5 mmol) as per the procedure of Example 20. $^1$H NMR (500 MHz; DMSO-$d_6$) δ 10.65 (s, 1H), 8.80 (brs, 0.6H), 8.68 (brs, 0.4H), 8.19(d, 1H), 8.11 (d, 1H), 7.81 (d, 0.6H), 7.75 (d, 0.4H), 7.62~7.54 (m, 2H), 6.92 (t, 1H), 6.90 (s, 1H), 6.82 (s, 2H), 5.93 (s, 2H), 5.00 (s, 2H), 4.72 (s, 1.2H), 4.54 (s, 0.8H), 4.26 (s, 0.8H), 4.01 (q, 0.8H), 4.00 (s, 1.2H), 3.96 (q, 1.2H), 3.51 (t, 1.2H), 3.35~3.30 (m, 2H), 3.13 (t, 0.8H), 1.12 (t, 1.2H), 1.06 (t, 1.8H).

Example 25

N-[2-(Benzothiazole-2-sulfonylamino)-ethyl]-N-{[4-N-(2-methylthioethoxycarbonyl)-cytosin-1-yl]-acetyl}-glycine ethyl ester The title compound (2.60 g, 85%) was synthesized by the reaction of N-[2-(benzothiazole-2-sulfonylamino)-ethyl]-glycine ethyl ester (1.72 g, 5 mmol) and [4-N-(2-methylthioethoxycarbonyl)-cytosin-1-yl]-acetic acid (1.44 g, 5 mmol) as per the procedure of Example 20. $^1$H NMR (500 MHz; DMSO-$d_6$) δ 8.89 (t, 0.6H) 8.75 (t, 0.4H) 8.28 (dd, 1H) 8.19 (dd, 1H) 7.90 (d, 0.6H) 7.84 (d, 0.4H) 7.67 (m, 2H) 6.99 (m, 1H) 4.81 (s, 1.2H) 4.62 (s, 0.8H) 4.35 (s, 0.8H) 4.26 (t, 2H) 4.14 (q, 0.8H) 4.06 (s, 1.2H) 4.04 (q, 1.2H) 3.59 (t, 1.2H) 3.42 (m, 2.0H) 3.21 (q, 0.8H) 2.73 (t, 2H) 2.12 (s, 3H) 1.20 (t, 1.2H) 1.15 (t, 1.8H).

Example 26

N-[2-(Benzothiazole-2-sulfonylamino)-ethyl]-N-{[6-N-(benzhydryloxycarbonyl)-adenin-9-yl]-acetyl}-glycine ethyl ester The title compound (2.91 g, 80%) was synthesized by the reaction of N-[2-(benzothiazole-2-sulfonylamino)-ethyl]-glycine ethyl ester (1.72 g, 5 mmol) and [6-N-(benzhydryloxycarbonyl)-adenin-9-yl]-acetic acid (2.02 g, 5 mmol) as per the procedure of Example 20. $^1$H NMR (500 MHz; DMSO-$d_6$) δ 10.93 (s, 1H), 9.00 (s, 0.6H), 8.60 (s, 0.4H), 8.59 (s, 0.4H), 8.54 (s, 0.6H), 8.33(d, 1H), 8.28 (m, 1H), 8.19 (d, 1H), 7.69 (m, 2H), 7.52-7.29 (m, 10H), 6.83 (s, 1H), 5.47 (s, 1.2H), 5.37 (s, 0.8H), 4.47 (s, 0.8H), 4.18 (q, 0.8H), 4.08 (s, 1.2H), 4.03 (q, 1.2H), 3.71 (t, 1.2H), 3.61 (q, 1.2H) 3.49 (t, 0.8H) 3.42 (q, 0.8H), 1.24 (t, 1.2H), 1.13 (t, 1.8H).

Example 27

N-[2-(Benzothiazole-2-sulfonylamino)-ethyl]-N-{[6-N-(4-methoxybenzyloxycarbonyl)-adenin-9-yl]-acetyl}-glycine ethyl ester To the mixture of N-[2-(benzothiazole-2-sulfonylamino)-ethyl]-glycine ethyl ester (172 mg, 0.5 mmol), [6-N-(4-methoxybenzyloxycarbonyl)-adenin-9-yl]-acetic acid (179 mg, 0.5 mmol), and HBTU (190 mg, 0.5 mmol) in DMF (2 ml) was added diisopropylethylamine (0.09 ml, 0.5 mmol) at ambient temperature. The resulting reaction mixture was stirred for 2 h at the same temperature and 1N HCl was added to the reaction mixture. The resulting precipitate product was filtered off, washed with water, and dried in vacuo to give the title compound as a white solid (0.35 g, 97%). $^1$H NMR (500 MHz; DMSO-$d_6$) δ 8.97 (t, 0.6H) 8.76 (t, 0.4H) 8.64 (s, 0.4H) 8.60 (s, 0.6H) 8.53 (d, 1H) 8.28 (m, 1H) 8.17 (d, 1H) 7.66 (m, 2H) 7.40 (d, 2H) 6.95 (d, 2H) 5.41 (s, 1.2H), 5.20 (s, 0.8H) 5.18 (s, 2H) 4.46 (s, 0.8H) 4.18 (q, 0.8H) 4.08 (s, 1.2H) 4.03 (q, 1.2H) 3.75 (s, 3H) 3.70 (q, 1.2H) 3.48 (q, 1.2H) 3.42 (t, 0.8H) 3.22 (q, 0.8H) 1.24 (t, 1.2H) 1.13 (t, 1.8H).

Example 28

N-[2-(Benzothiazole-2-sulfonylamino)-ethyl]-N-{[6-N-(3,4-dimethoxybenzyloxycarbonyl)-adenin-9-yl]-acetyl}-glycine ethyl ester The title compound (6.28 g, 96%) was synthesized by the reaction of N-[2-(benzothiazole-2-sulfonylamino)-ethyl]-glycine ethyl ester (3.26 g, 9.5 mmol) and [6-N-(3,4-dimethoxybenzyloxycarbonyl)-adenin-9-yl]-acetic acid (3.50 g, 9.03 mmol) as per the procedure of Example 27. $^1$H NMR (500 MHz; DMSO-$d_6$) δ 10.58 (s, 1H), 8.98 (brs, 0.6H), 8.77 (brs, 0.4H), 8.57 (s, 0.4H), 8.53 (s, 0.6H), 8.29 (d, 1H), 8.27 (m, 1H), 8.17 (d, 1H), 7.65 (m, 2H), 7.08 (s, 1H), 6.98 (d, 1H), 6.94 (d, 1H), 5.35 (s, 1.2H), 5.15 (s, 0.8H), 5.12 (s, 2H), 4.45 (s, 0.8H), 4.18 (q, 0.8H), 4.07 (s, 1.2H), 4.01 (q, 1.2H), 3.75 (s, 3H), 3.74 (s, 3H), 3.70 (t, 1.2H), 3.48 (t, 1.2H), 3.42 (t, 0.8H), 3.22 (t, 0.8H), 1.23 (t, 1.2H), 1.12 (t, 1.8H).

Example 29

N-[2-(Benzothiazole-2-sulfonylamino)-ethyl]-N-{[6-N-(piperonyloxycarbonyl)-adenin-9-yl]-acetyl}-glycine ethyl ester The title compound (2.96 g, 85%) was synthesized by the reaction of N-[2-(benzothiazole-2-sulfonylamino)-ethyl]-glycine ethyl ester (1.72 g, 5 mmol) and [6-N-(piperonyloxycarbonyl)-adenin-9-yl]-acetic acid (1.86 g, 5 mmol) as per the procedure of Example 20. $^1$H NMR (500 MHz; DMSO-$d_6$) δ 10.63 (s, 1H), 8.98 (brs, 0.6H), 8.77 (brs, 0.4H), 8.57 (s, 0.4H), 8.52 (s, 0.6H), 8.29 (d, 1H), 8.27 (m, 1H), 8.17 (d, 1H), 7.65 (m, 2H), 7.04 (s, 1H), 6.94 (d, 1H), 6.90 (d, 1H), 6.01 (s, 2H), 5.36 (s, 1.2H), 5.15 (s, 0.8H), 5.10 (s, 2H), 4.45 (s, 0.8H), 4.17 (q, 0.8H), 4.07 (s, 1.2H), 4.01 (q, 1.2H), 3.70 (t, 1.2H), 3.48 (t, 1.2H), 3.41 (t, 0.8H), 3.22 (t, 0.8H), 1.23 (t, 1.2H), 1.12 (t, 1.8H).

Example 30

N-[2-(Benzothiazole-2-sulfonylamino)-ethyl]-N-{[6-N-(2-methylthioethoxycarbonyl)-adenin-9-yl]-acetyl}-glycine ethyl ester The title compound (2.77 g, 85%) was synthesized by the reaction of N-[2-(benzothiazole-2-sulfonylamino)-ethyl]-glycine ethyl ester (1.72 g, 5 mmol) and [6-N-(2-methylthioethoxycarbonyl)-adenin-9-yl]-acetic acid (1.56 g, 5 mmol); as per the procedure of Example 20. $^1$H NMR (500 MHz; DMSO-$d_6$) δ 10.59 (s, 1H), 8.97 (brs, 0.6H), 8.76 (brs, 0.4H), 8.57 (s, 0.4H), 8.52 (s, 0.6H), 8.28 (d, 1H), 8.17 (d, 1H), 7.65 (m, 2H), 5.35 (s, 1.2H), 5.14 (s, 0.8H), 4.46 (s, 0.8H), 4.17 (q, 0.8H), 4.06 (s, 1.2H), 4.02 (q, 1.2H), 3.70 (t, 1.2H), 3.47 (t, 1.2H), 3.42 (t, 0.8H), 3.21 (t, 0.8H), 2.12 (s, 3H), 1.23 (t, 1.2H), 1.12 (t, 1.8H).

Example 31

N-[2-(Benzothiazole-2-sulfonylamino)-ethyl]-N-{[2-N-(benzhydryloxycarbonyl)-guanin-9-yl]-acetyl}-glycine ethyl ester The title compound (2.61 g, 70%) was synthesized by the reaction of N-[2-(benzothiazole-2-sulfonylamino)-ethyl]-glycine ethyl ester (1.72 g, 5 mmol) and [2-N-(benzhydryloxycarbonyl)-guanin-9-yl]-acetic acid (2.10 g, 5 mmol) as per the procedure of Example 20. $^1$H NMR (500 MHz; DMSO-$d_6$) δ 11.63 (bs, 1H), 11.23 (bs, 1H), 8.27 (d, 1H), 8.17 (t, 1H), 7.80 (s, 0.6H), 7.76 (s, 0.4H), 7.65 (m, 2H), 7.50~7.25 (m, 10H), 6.86 (s, 1H), 5.12 (s, 1.2H), 4.93 (s, 0.8H), 4.44 (s, 0.8H), 4.18 (q, 0.8H), 4.08 (s, 1.2H), 4.04 (q, 1.2H), 3.65 (t, 1.2H), 3.45 (t, 1.2H), 3.41 (t, 0.8H), 3.21 (t, 0.8H), 1.23 (t, 1.2H), 1.17 (t, 1.8H).

Example 32

N-[2-(Benzothiazole-2-sulfonylamino)-ethyl]-N-{[2-N-(4-methoxybenzyloxycarbonyl)-guanin-9-yl]-acetyl}-glycine ethyl ester The title compound (2.72 g, 78%) was synthesized by, the reaction of N-[2-(benzothiazole-2-sulfonylamino)-ethyl]-glycine ethyl ester (1.72 g, 5 mmol) and [2-N-(4-methoxybenzyloxycarbonyl)-guanin-9-yl]-acetic acid (1.89 g, 5 mmol) as per the procedure of Example 20. $^1$H NMR (500 MHz; DMSO-$d_6$) δ 8.26 (dd, 1H), 8.15 (dd, 1H), 7.80 (s, 0.6H), 7.76 (s, 0.4H), 7.65 (m, 2H), 7.36 (d, 2H), 6.94 (d, 2H), 5.16 (s, 2H), 5.09 (s, 1.2H), 4.90 (s, 0.8H), 4.42 (s, 0.8H), 4.16 (q, 0.8H), 4.06 (s, 1.2H), 4.03 (q, 1.2H), 3.75 (s, 3H), 3.63(t, 1.2H), 3.43 (t, 1.2H), 3.39 (t, 0.8H), 3.20 (t, 0.8H), 1.21 (t, 1.2H), 1.12 (t, 1.8H).

Example 33

N-[2-(Benzothiazole-2-sulfonylamino)-ethyl]-N-{[2-N-(3,4-dimethoxybenzyloxycarbonyl)-guanin-9-yl]-acetyl}-glycine ethyl ester The title compound (2.48 g, 68%) was synthesized by the reaction of N-[2-(benzothiazole-2-sulfonylamino)-ethyl]-glycine ethyl ester (1.72 g, 5 mmol) and [2-N-(3,4-dimethoxybenzyloxycarbonyl)-guanin-9-yl]-acetic acid (2.02 g, 5 mmol) as pet the procedure of Example 20. $^1$H NMR (500 MHz; DMSO-$d_6$) δ 8.26 (dd, 1H), 8.14 (dd, 1H), 7.80 (s, 0.6H), 7.76 (s, 0.4H), 7.65 (m, 2H), 7.04 (s, 1H), 6.95 (m, 2H), 5.15 (s, 2H), 5.09 (s, 1.2H), 4.90 (s, 0.8H), 4.42 (s, 0.8H), 4.16 (q, 0.8H), 4.06 (s, 1.2H), 4.03 (q, 1.21H), 3.74 (s, 3H), 3.73 (s, 3H), 3.62 (t, 1.2H), 3.43 (t, 1.2H), 3.39 (t, 0.8H), 3.20 (t, 0.8H), 1.21 (t, 1.2H), 1.13 (t, 1.8H).

Example 34

N-[2-(Benzothiazole-2-sulfonylamino)-ethyl]-N-{[2-N-(piperonylyloxycarbonyl)-guanin-9-yl]-acetyl}-glycine ethyl ester The title compound (2.71 g, 76%) was synthesized by the reaction of N-[2-(benzothiazole-2-sulfonylamino)-ethyl]-glycine ethyl ester (1.72 g, 5 mmol) and [2-N-(piperonyloxycarbonyl)-guanin-9-yl]-acetic acid (1.94 g, 5 mmol) as per the procedure of Example 20. $^1$H NMR (500 MHz; DMSO-$d_6$) δ 8.27 (d, 1H), 8.15 (dd, 1H), 7.80 (s, 0.6H), 7.76 (s, 0.4H), 7.65 (m, 2H), 7.01 (s, 1H), 6.95 (s, 2H), 6.01 (s, 2H), 5.13 (s, 2H), 5.10 (s, 1.2H), 4.91 (s, 0.8H), 4.43 (s, 0.8H), 4.16 (q, 0.8H), 4.06 (s, 1.2H), 4.03 (q, 1.2H), 3.62 (t, 1.2H), 3.43 (t, 1.2H), 3.39 (t, 0.8H), 3.19 (t, 0.8H), 1.21 (t, 1.2H), 1.13 (t, 1.8H).

Example 35

N-[2-(Benzothiazole-2-sulfonylamino)-ethyl]-N-{[2-N-(2-methylthioethoxycarbonyl)-guanin-9-yl]-acetyl}-glycine ethyl ester The title compound (2.67 g, 75%) was synthesized by the reaction of N-[2-(benzothiazole-2-sulfonylamino)-ethyl]-glycine ethyl ester (1.72 g, 5 mmol) and [2-N-(2-methylthioethoxycarbonyl)-guanin-9-yl]-acetic acid (1.64 g, 5 mmol) as per the procedure of Example 20.

Example 36

N-[2-(Benzothiazole-2-sulfonylamino)-ethyl]-N-[(thymin-1-yl)-acetyl]-glycine

N-[2-(Benzothiazole-2-sulfonylamino)-ethyl]-N-[(thymin-1-yl)-acetyl]-glycine ethyl ester (5.10 g, 10 mmol) was suspended in tetrahydrofuran (20 mL) and the solution of lithium hydroxide monohydrate (1.03 g, 25 mmol) in water (20 mL) was added. The reaction mixture was stirred for 1 h. at ambient temperature. The aqueous solution was acidified by the dropwise addition of 1N HCl at 0° C. The title compound was extracted with ethyl acetate (3×10 mL), the combined extracts were dried over magnesium sulfate and filtered. The filtrate was evaporated to dryness in vacuo to afford the desired product (4.57 g, 95%). $^1$H NMR (500 MHz; DMSO-$d_6$) δ 11.30 (s, 0.6H), 11.28 (s, 0.4H), 8.88 (s, 0.6H), 8.77 (s, 0.4H), 8.27 (d, 1H), 8.18 (d, 1H), 7.69~7.64 (m, 2H), 7.31 (s, 0.6H), 7.23 (s, 0.4H), 4.64 (s, 1.2H), 4.45 (s, 0.8H), 4.21 (s, 0.8H), 3.98 (s, 1.2H), 3.52 (t, 1.2H), 3.38 (s, 2H), 3.21 (t, 0.8H), 1.73 (s, 3H).

Example 37

N-[2-(Benzothiazole-2-sulfonylamino)-ethyl]-N-{[4-N-(benzhydryloxycarbonyl)-cytosin-1-yl]-acetyl}-glycine The title compound (629 mg, 93%) was synthesized from N-[2-(benzothiazole-2-sulfonylamino)-ethyl]-N-{[4-N-(benzhydryloxycarbonyl)-cytosin-1-yl]-acetyl}-glycine ethyl ester (705 mg, 1.0 mmol) as per the procedure of Example 36. $^1$H NMR (500 MHz; DMSO-$d_6$) δ 11.00 (brs 1H), 8.90 (brs, 1H), 8.26(dd, 1H), 8.18 (d, 1H), 7.90 (d, 0.6H), 7.82 (d, 0.4H), 7.68~7.61 (m, 2H), 7.45~7.62 (m, 10H), 6.94 (dd, 1H), 6.79 (s, 1H), 4.80(s, 1.2H), 4.60 (s, 0.8H), 4.20 (s, 0.8H), 3.99 (s, 1.2H), 3.56 (t, 1.2H), 3.39(m, 2H), 3.21 (t, 0.8H).

Example 38

N-[2-(Benzothiazole-2-sulfonylamino)-ethyl]-N-{[4-N-(4-methoxybenzyloxycarbonyl)-cytosin-1-yl]-acetyl}-glycine The title compound (605 mg, 96%) was synthesized from N-[2-(benzothiazole-2-sulfonylamino)-ethyl]-N-{[4-N-(4-methoxybenzyloxycarbonyl)-cytosin-1-yl]-acetyl}-glycine ethyl ester (658 mg, 1.0 mmol) as per the procedure of Example 36. $^1$H NMR (500 MHz; DMSO-$d_6$) δ 10.75 (bs, 1H), 8.89 (t, 0.6H), 8.76 (t, 0.4H), 8.27 (d, 1H), 8.19 (d, 1H), 7.90 (d, 0.6H), 7.83 (d, 0.4H), 7.65 (m, 2H), 7.34(d, 2H), 7.00 (dd, 1H), 6.92 (d, 2H), 5.10 (s, 2H), 4.80 (s, 1.2H), 4.60 (s, 0.8H), 4.25 (s, 0.8H), 4.00 (s, 1.2H), 3.77 (s, 3H), 3.56 (t, 1.2H), 3.39 (m, 2H), 3.21 (t, 0.8H).

Example 39

N-[2-(Benzothiazole-2-sulfonylamino)-ethyl]-N-{[4-N-(3,4-dimethoxybenzyloxycarbonyl)-cytosin-1-yl]-acetyl}-glycine The title compound (607 mg, 92%) was synthesized from N-[2-(benzothiazole-2-sulfonylamino)-ethyl]-N-{[4-N-(3,4-dimethoxybenzyloxycarbonyl)-cytosin-1-yl]-acetyl}-glycine ethyl ester (689 mg, 1.0 mmol) as per the procedure of Example 36. $^1$H NMR (500 MHz; DMSO-$d_6$) δ 10.85 (brs, 1H), 8.88 (t, 0.6H), 8.75 (t, 0.4H), 8.28 (d, 1H), 8.19 (d, 1H), 7.90 (d, 0.6H), 7.83 (d, 0.4H), 7.66 (m, 2H), 7.03 (s, 1H), 7.01 (dd, 1H), 6.93 (s, 2H), 5.09 (s, 2H), 4.79 (s, 1.2H), 4.60 (s, 0.8H), 4.25 (s, 0.8H), 3.99 (s, 1.2H), 3.75 (s, 3H), 3.74 (s, 3H), 3.56 (t, 1.2H), 3.40 (m, 2H), 3.20 (dd, 0.8H).

Example 40

N-[2-(Benzothiazole-2-sulfonylamino)-ethyl]-N-{[4-N-(piperonyloxycarbonyl)-cytosin-1-yl]-acetyl}-glycine The title compound (632 mg, 92%) was synthesized from N-[2-(benzothiazole-2-sulfonylamino)-ethyl]-N-{[4-N-(piperonyloxycarbonyl)-cytosin-1-yl]-acetyl}-glycine ethyl ester (673 mg, 1.0 mmol) as per the procedure of Example 36. $^1$H NMR (500 MHz; DMSO-$d_6$) δ 10.72 (brs, 1H), 8.25 (d, 1H), 8.18 (d, 1H), 7.89 (d, 0.4H), 7.82 (d, 0.6H), 7.63 (m, 2H), 6.98 (s, 1H), 6.97 (dd, 1H), 6.90 (s, 2H), 6.00 (s, 2H), 5.06 (s, 2H), 4.77 (s, 0.8H), 4.54 (s, 1.2H), 3.90 (s, 2H), 3.58 (t, 1.2H), 3.40 (m, 1.6H), 3.20 (t, 1.2H).

Example 41

N-[2-(Benzothiazole-2-sulfonylamino)-ethyl]-N-{[4-N-(2-methylthioethoxycarbonyl)-cytosin-1-yl]-acetyl}-glycine The title compound (537 mg, 92%) was synthesized from of N-[2-(benzothiazole-2-sulfonylamino)-ethyl]-N-{[4-N-(2-methylthioethoxycarbonyl)-cytosin-1-yl]-acetyl}-glycine ethyl ester (613 mg, 1.0 mmol) as per the procedure of Example 36. $^1$H NMR (500 MHz; DMSO-$d_6$) δ 8.87 (t, 0.6H), 8.74 (t, 0.4H), 8.28 (dd, 1H), 8.19 (m, 1H), 7.90 (d, 0.6H), 7.83 (d, 0.4H), 7.66 (m, 2H), 6.98 (m, 1H), 4.80 (s, 1.2H), 4.61 (s, 0.8H), 4.26 (t, 3H), 4.25 (s, 0.8H), 4.00 (q, 1.2H), 3.57 (t, 1.2H), 3.40 (m, 2.0H), 3.22 (q, 0.8H), 2.73 (t, 2H), 2.12 (s, 3H).

Example 42

N-[2-(Benzothiazole-2-sulfonylamino)-ethyl]-N-{[6-N-(benzhydryloxycarbonyl)-adenin-9-yl]-acetyl}-glycine The title compound (631 mg, 90%) was synthesized from of N-[2-(benzothiazole-2-sulfonylamino)-ethyl]-N-{[6-N-(benzhydryloxycarbonyl)-adenin-9-yl]-acetyl}-glycine ethyl ester (729 mg, 1.0 mmol) as per the procedure of Example 36. $^1$H-NMR (500 MHz; DMSO-$d_6$) δ 11.00 (s, 1H). 9.00 (br, 1H), 8.55 (d, 1H), 8.32 (d, 1H), 8.26 (m, 1H), 8.17 (m, 1H), 7.64 (m, 2H), 7.52-7.26 (m, 10H), 6.81 (s, 1H), 5.35 (s, 1H), 5.13 (s, 1H), 4.33 (s, 1H), 4.00 (s, 1H), 3.67 (t, 1H), 3.48 (t, 1H), 3.40 (t, 1H), 3.22 (t, 1H).

Example 43

N-[2-(Benzothiazole-2-sulfonylamino)-ethyl]-N-{[6-N-(4-methoxybenzyloxycarbonyl)-adenin-9-yl]-acetyl}-glycine The title compound (596 mg, 91%) was synthesized from of N-[2-(benzothiazole-2-sulfonylamino)-ethyl]-N-{[6-N-(4-methoxybenzyloxycarbonyl)-adenin-9-yl]-acetyl}-glycine ethyl ester (683 mg, 1.0 mmol) as per the procedure of Example 36. $^1$H NMR (500 MHz; DMSO-$d_6$) δ 11.75 (brs, 1H), 8.57 (d, 1H), 8.37 (d, 1H), 8.27 (d, 1H), 8.18 (dd, 1H), 7.65 (m, 2H), 7.39 (d, 2H), 6.94 (d, 2H), 5.36 (s, 1H), 5.15 (s, 3H), 4.37 (s, 1H), 4.01 (s, 1H), 3.75 (s, 3H), 3.68 (t, 1H), 3.48 (q, 1H), 3.40 (q, 1H), 3.22 (q, 1H).

Example 44

N-[2-(Benzothiazole-2-sulfonylamino)-ethyl]-N-{[6-N-(3,4-dimethoxybenzyloxycarbonyl)-adenin-9-yl]-acetyl}-glycine The title compound (597 mg, 87%) was synthesized from of N-[2-(benzothiazole-2-sulfonylamino)-ethyl]-N-{[6-N-(3,4-dimethoxybenzyloxycarbonyl)-adenin-9-yl]-acetyl}-glycine ethyl ester (713 mg, 1.0 mmol) as per the procedure of Example 36. $^1$H NMR (500 MHz; DMSO-$d_6$) δ 11.60 (brs, 1H), 8.56 (s, 0.5H), 8.53 (s, 0.5H), 8.29 (d, 1H), 8.27 (d, 1H), 8.18 (dd, 1H), 7.64 (m, 2H), 7.08 (s, 1H), 6.98 (d, 1H), 6.94 (d, 1H), 5.34 (s, 1H), 5.13 (s, 1H), 5.12 (s, 2H), 4.36 (s, 1H), 4.00 (s, 1H), 3.76 (s, 3H), 3.74 (s, 3H), 3.67 (t, 1H), 3.48 (q, 1H), 3.40 (q, 1H), 3.22 (q, 1H).

Example 45

N-[2-(Benzothiazole-2'-sulfonylamino)-ethyl]-N-{[6-N-(piperonyloxycarbonyl)-adenin-9-yl]-acetyl}-glycine The title compound (629 mg, 94%) was synthesized from of N-[2-(benzothiazole-2-sulfonylamino)-ethyl]-N-{[6-N-(piperonyloxycarbonyl)-adenin-9-yl]-acetyl}-glycine ethyl ester (697 mg, 1.0 mmol) as per the procedure of Example 36. $^1$H NMR (500 MHz; DMSO-$d_6$) δ 11.65 (brs, 1H), 8.55 (s, 0.5H), 8.53 (s, 0.5H), 8.30 (s, 0.5H), 8.27 (s, 0.5H), 8.25 (d, 1H), 8.17 (dd, 1H), 7.64 (m, 2H), 7.04 (s, 1H), 6.94 (d, 1H), 6.90 (d, 1H), 6.01 (s, 2H), 5.34 (s, 1H), 5.09 (s, 3H), 4.20 (s, 1H), 3.98 (s, 1H), 3.67 (t, 1H), 3.49 (t, 1H), 3.41 (t, 1H), 3.23 (t, 1H).

Example 46

N-[2-(Benzothiazole-2-sulfonylamino)-ethyl]-N-{[6-N-(2-methylthioethoxycarbonyl)-adenin-9-yl]-acetyl}-glycine The title compound (560 mg, 92%) was synthesized from of N-[2-(benzothiazole-2-sulfonylamino)-ethyl]-N-{[6-N-(2-methylthioethoxycarbonyl)-adenin-9-yl]-acetyl}-glycine ethyl ester (637 mg, 1.0 mmol) as per the procedure of Example 36.

Example 47

N-[2-(Benzothiazole-2-sulfonylamino)-ethyl]-N-{[2-N-(benzhydryloxycarbonyl)-guanin-9-yl]-acetyl}-glycine The title compound (645 mg, 90%) was synthesized from of N-[2-(benzothiazole-2-sulfonylamino)-ethyl]-N-{[2-N-(benzhydryloxycarbonyl)-guanin-9-yl]-acetyl}-glycine ethyl ester (745 mg, 1 mmol) as per the procedure of Example 36. $^1$H NMR (500 MHz; DMSO-$d_6$) δ 11.68 (d, 1H), 11.26 (brs, 2H), 8.94 (t, 0.6H), 8.76 (t, 0.4H), 8.27 (d, 1H), 8.17 (m, 1H), 7.90 (s, 0.6H), 7.87 (s, 0.4H), 7.65 (m, 2H), 7.50~7.25 (m, 10H), 6.86 (s, 1H), 5.12 (s, 1.2H), 4.94 (s, 0.8H), 4.35 (s, 0.8H), 4.00 (s, 1.2H), 3.62 (m, 1.2H), 3.40 (m, 2H), 3.22 (m, 0.8H).

Example 48

N-[2-(Benzothiazole-2-sulfonylamino)-ethyl]-N-{[2-N-(4-methoxybenzyloxycarbonyl)-guanin-9-yl]-acetyl}-glycine The title compound (643 mg, 92%) was synthesized from of N-[2-(benzothiazole-2-sulfonylamino)-ethyl]-N-{[2-N-(4-methoxybenzyloxycarbonyl)-guanin-9-yl]-acetyl}-glycine ethyl ester (699 mg, 1 mmol) as per the procedure of Example 36. $^1$H NMR (500 MHz; DMSO-$d_6$) δ 8.92 (t, 0.6H), 8.76 (t, 0.4H), 8.26 (dd, 1H), 8.16 (dd, 1H), 7.80 (s, 0.6H), 7.75 (s, 0.4H), 7.67~7.61 (m, 2H), 7.36 (d, 2H), 6.94 (d, 2H), 5.16 (s, 2H), 5.08 (s, 1.2H), 4.89 (s, 0.8H), 4.33 (s, 0.8H), 4.00 (s, 1.2H), 3.74 (s, 3H), 3.60 (t, 1.2H), 3.43 (t, 0.8H), 3.38 (m, 1.2H), 3.22 (m, 0.8H).

Example 49

N-[2-(Benzothiazole-2-sulfonylamino)-ethyl]-N-{[2-N-(3,4-dimethoxybenzyloxycarbonyl)-guanin-9-yl]-acetyl}-glycine The title compound (603 mg, 86%) was synthesized from of N-[2-(benzothiazole-2-sulfonylamino)-ethyl]-N-{[2-N-(3,4-dimethoxybenzyloxycarbonyl)-guanin-9-yl]-acetyl}-glycine ethyl ester (729 mg, 1 mmol) as per the procedure of Example 36. $^1$H NMR (500 MHz; DMSO-$d_6$) δ 11.36 (s, 0.5H), 11.34 (s, 0.5H), 8.26 (d, 1H), 8.16 (dd, 1H), 7.80 (s, 0.5H), 7.75 (s, 0.5H), 7.67-7.61 (m, 2H), 7.03 (s, 1H), 6.97-6.94 (m, 2H), 5.15 (s, 2H), 5.08 (s, 1H), 4.88 (s, 1H), 4.26 (s, 1H), 3.98 (s, 1H), 3.75 (s, 3H), 3.74 (s, 3H), 3.60 (t, 1H), 3.43 (t, 1H), 3.38 (t, 1H), 3.21 (t, 1H).

Example 50

N-[2-(Benzothiazole-2-sulfonylamino)-ethyl]-N-{[2-N-(piperonyloxycarbonyl)-guanin-9-yl]-acetyl}-glycine The title compound (630 mg, 92%) was synthesized from of N-[2-(benzothiazole-2-sulfonylamino)-ethyl]-N-{[2-N-(piperonyloxycarbonyl)-guanin-9-yl]-acetyl}-glycine ethyl ester (713 mg, 1 mmol) as per the procedure of Example 36. $^1$H NMR (500 MHz; DMSO-$d_6$) δ 11.36 (s, 0.5H), 11.35 (s, 0.5H), 8.25 (d, 1H), 8.16 (dd, 1H), 7.81 (s, 0.5H), 7.76 (s, 0.5H), 7.68-7.61 (m, 2H), 7.00 (s, 1H), 6.91 (s, 2H), 6.01 (s, 2H), 5.12 (s, 2H), 5.09 (s, 1H), 4.89 (s, 1H), 4.25 (s, 1H), 3.99 (s, 1H), 3.61 (t, 1H), 3.44 (t, 1H), 3.39 (t, 1H), 3.21 (t, 1H).

Example 51

N-[2-(Benzothiazole-2-sulfonylamino)-ethyl]-N-{[2-N-(2-methylthioethoxycarbonyl)-guanin-9-yl]-acetyl}-glycine The title compound (581 mg, 93%) was synthesized from of N-[2-(benzothiazole-2-sulfonylamino)-ethyl]-N-{[2-N-(2-methylthioethoxycarbonyl)-guanin-9-yl]-acetyl}-glycine ethyl ester (653 mg, 1 mmol) as per the procedure of Example 36. $^1$H NMR (500 MHz; DMSO-$d_6$) δ 11.35 (s, 0.5H), 11.32 (s, 0.5H), 8.26 (d, 1H), 8.16 (dd, 1H), 7.82 (s, 0.5H), 7.79 (s, 0.51H), 7.67-7.61 (m, 2H), 5.08 (s, 1H), 4.90 (s, 1H), 4.33 (s, 1H), 4.30 (t, 2H), 3.99 (s, 1H), 3.62 (t, 1H), 3.45 (t, 1H), 3.39 (t, 1H), 3.20 (t, 1H), 3.13 (t, 2H), 2.51 (s, 3H).

Example 52

1-(Benzothiazole-2-sulfonyl)-4-[(thymin-1-yl)-acetyl]-piperazin-2-one

To the mixture of 1-(benzothiazole-2-sulfonyl)-piperazin-2-one trifluoroacetic acid salt (0.83 g, 2.5 mmol), (thymin-1-yl)-acetic acid (0.46 g, 2.5 mmol), and PyBOP (1.43 g, 2.75 mmol) in DMF (12 mL) was added diisopropylethylamine (0.61 ml, 3.75 mmol) at ambient temperature. The resulting reaction mixture was stirred for 4 h at the same temperature and the solvent was removed in vacuo. The residue was dissolved in dichloromethane (20 mL) and the solution was washed with water, saturated sodium bicarbonate solution, 1N HCl solution, and saline. The resulting solution was dried over magnesium sulfate and filtered. The filtrate was evaporated in vacuo. The resulting residue was recrystallized in dichloromethane-ethyl ether to afford the title compound. $^1$H NMR MHz; DMSO-$d_6$) δ 11.30 (d, 1H), 8.34 (d, 1H), 8.26 (m, 1H), 7.71 (m, 2H), 7.34 (s, 0.6H), 7.27 (s, 0.4H), 4.67 (s, 1.2H), 4.57 (s, 0.8H), 4.42 (s, 0.8H), 4.27 (s, 1.2H), 4.21 (t, 1.2H), 4.07 (t, 0.8H), 3.95 (t, 1.2H), 3.85 (t, 0.8H), 1.74 (s, 3H).

Example 53

1-(4-Chloro-5-methoxy-benzothiazole-2-sulfonyl)-4-[(thymin-1-yl)-acetyl]-piperazin-2-one The title compound was synthesized by the reaction of 1-(4-chloro-5-methoxy-benzothiazole-2-sulfonyl)-piperazin-2-one trifluoroacetic acid salt with [4-N-(benzyloxycarbonyl)-cytosin-1-yl]-acetic acid as per the procedure of Example 52. $^1$H NMR (500 MHz; DMSO-$d_6$) δ 11.30 (s, 0.6H), 11.29 (s, 0.4H), 8.27 (d, 1H), 7.66 (d, 1H), 7.33 (s, 0.6H), 7.27 (s, 0.4H), 4.67 (s, 1.2H), 4.57 (s, 0.8H), 4.42 (s, 0.8H), 4.28 (s, 1.2H), 4.21 (t, 1.2H), 4.07 (t, 0.8H), 3.99 (s, 3H), 3.95 (t, 1.2H), 3.85 (t, 0.8H).

Example 54

1-(Benzothiazole-2-sulfonyl)-4-{[4-N-(benzyloxycarbonyl)-cytosin-1-yl]-acetyl}-piperazin-2-one The title compound was synthesized by the reaction of 1-(benzothiazole-2-sulfonyl)-piperazin-2-one trifluoroacetic acid salt with [4-N-(benzyloxycarbonyl)-cytosin-1-yl]-acetic acid as per the procedure of Example 52. $^1$H NMR (500 MHz; DMSO-$d_6$) δ 10.79 (brs, 1H), 8.34 (m, 1H), 8.26 (m, 1H), 7.91 (d, 0.6H), 7.85 (d, 0.4H), 7.45~7.30 (m, 5H), 7.10 (t, 1H), 5.18 (s, 2H), 4.82 (s, 1.2H), 4.72 (s, 0.8H), 4.45 (s, 0.8H), 4.28 (s, 1.2H), 4.22 (t, 1.2H), 4.07 (t, 0.8H), 3.99 (t, 1.2H), 3.86 (t, 0.8H).

Example 55

1-(Benzothiazole-2-sulfonyl)-4-{[4-N-(benzhydryloxycarbonyl)-cytosin-1-yl]-acetyl}-piperazin-2-one The title compound was synthesized by the reaction of 1-(benzothiazole-2-sulfonyl)-piperazin-2-one trifluoroacetic acid salt with [4-N-(benzhydryloxycarbonyl)-cytosin-1-yl]-acetic acid as per the procedure of Example 52. $^1$H NMR (500 MHz; DMSO-$d_6$) δ 11.00 (brs, 1H), 8.34 (m, 1H), 8.26 (m, 1H), 7.90 (d, 0.6H), 7.84 (d, 0.4H), 7.72 (m, 2H), 7.44 (d, 4H), 7.37 (t, 4H), 7.29 (t, 2H), 6.94 (t, 1H), 6.79 (s, 1H), 4.82 (s, 1.2H), 4.72 (s, 0.8H), 4.45 (s, 0.8H), 4.28 (s, 1.2H), 4.22 (t, 1.2H), 4.07 (t, 0.8H), 3.99 (t, 1.2H), 3.86 (t, 0.8H).

Example 56

1-(Benzothiazole-2-sulfonyl)-4-{[4-N-(4-methoxybenzyloxycarbonyl)-cytosin-1-yl]-acetyl}-piperazin-2-one The title compound was synthesized by the reaction of 1-(benzothiazole-2-sulfonyl)-piperazin-2-one trifluoroacetic acid salt with [4-N-(4-methoxybenzyloxycarbonyl)-cytosin-1-yl]-acetic acid as per the procedure of Example 52. $^1$H NMR (500 MHz; DMSO-$d_6$) δ 10.70 (bs, 1H), 8.34 (m, 1H), 8.26 (m, 1H), 7.90 (d, 0.6H), 7.84 (d, 0.4H), 7.72 (m, 2H), 7.34 (d, 2H), 7.01 (t, 1H), 6.93 (d, 2H), 5.10 (s, 2H), 4.81 (s, 1.2H), 4.71 (s, 0.8H), 4.45 (s, 0.8H), 4.27 (s, 1.2H), 4.22 (t, 1.2H), 4.07 (t, 0.8H), 3.99 (t, 1.2H), 3.85 (t, 0.8H), 3.74 (s, 3H).

Example 57

1-(Benzothiazole-2-sulfonyl)-4-{[4-N-(3,4-dimethoxybenzyloxycarbonyl)-cytosin-1-yl]-acetyl}-piperazin-2-one The title compound was synthesized by the reaction of 1-(benzothiazole-2-sulfonyl)-piperazin-2-one trifluoroacetic acid salt with [4-N-(3,4-dimethoxybenzyloxycarbonyl)-cytosin-1-yl]-acetic acid as per the procedure of Example 52. $^1$H NMR (500 MHz; DMSO-$d_6$) δ 10.73 (brs, 1H), 8.34 (m, 1H), 8.26 (m, 1H), 7.90 (d, 0.6H), 7.84 (d, 0.4H), 7.71 (m, 2H), 7.03 (s, 1H), 7.02 (t, 1H), 6.94 (s, 2H), 5.09 (s, 2H), 4.82 (s, 1.2H), 4.72 (s, 0.8H), 4.45 (s, 0.8H), 4.27 (s, 1.2H), 4.21 (t, 1.2H), 4.06 (t, 0.8H), 3.99 (t, 1.2H), 3.85 (t, 0.8H), 3.75(s, 3H), 3.74 (s, 3H).

Example 58

1-(Benzothiazole-2-sulfonyl)-4-{[4-N-(piperonyloxycarbonyl)-cytosin-1-yl]-acetyl}-piperazin-2-one The title compound was synthesized by the reaction of 1-(benzothiazole-2-sulfonyl)-piperazin-2-one trifluoroacetic acid salt with [4-N-(piperonyloxycarbonyl)-cytosin-1-yl]-acetic acid as per the procedure of Example 52. $^1$H NMR (500 MHz; DMSO-$d_6$) δ 10.76 (hrs, 1H), 8.36 (m, 1H), 8.28 (m, 1H), 7.92 (d, 0.6H), 7.86 (d, 0.4H), 7.73 (m, 2H), 7.03 (t, 1H), 7.00 (s, 1H), 6.92 (s, 2H), 6.03 (s, 2H), 5.08 (s, 2H), 4.84 (s, 1.2H), 4.74 (s, 0.8H), 4.47 (s, 0.8H), 4.30 (s, 1.2H), 4.24 (t, 1.2H), 4.08 (t, 0.8H), 4.01 (t, 1.2H), 3.89 (t, 0.8H).

Example 59

1-(Benzothiazole-2-sulfonyl)-4-{[4-N-(2-methylthioethoxycarbonyl)-cytosin-1-yl]-acetyl}-piperazin-2-one The title compound was synthesized by the reaction of 1-(benzothiazole-2-sulfonyl)-piperazin-2-one trifluoroacetic acid salt with [4-N-(2-methylthioethoxycarbonyl)-cytosin-1-yl]-acetic acid as per the procedure of Example 52. $^1$H NMR (500 MHz; DMSO-$d_6$) δ 10.72 (brs, 1H), 8.34 (m, 1H), 8.26 (m, 1H), 7.90 (d, 0.6H), 7.84 (d, 0.4H), 7.72 (m, 2H), 7.01 (t, 1H), 4.82 (s, 1.2H), 4.71 (s, 0.8H), 4.45 (s, 0.8H), 4.27 (s, 1.2H), 4.26 (t, 2H), 4.22 (t, 1.2H), 4.07 (t, 0.8H), 3.99 (t, 1.2H), 3.86 (t, 0.8H), 2.73 (t, 2H), 2.11 (s, 3H).

Example 60

1-(5-Chloro-benzothiazole-2-sulfonyl)-4-{[4-N-(benzhydryloxycarbonyl)-cytosin-1-yl]-acetyl}-piperazin-2-one The title compound was synthesized by the reaction of 1-(5-chloro-benzothiazole-2-sulfonyl)-piperazin-2-one trifluoroacetic acid salt with [4-N-(benzhydryloxycarbonyl)-cytosin-1-yl]-acetic acid as per the procedure of Example 52. $^1$H NMR (500 MHz; DMSO-$d_6$) δ 10.98 (brs, 1H), 8.40 (m, 2H), 7.96 (s, 1H), 7.79 (m, 1H), 7.45 (d, 4H), 7.38 (t, 4H), 7.30 (t, 2H), 6.96 (t, 1H), 6.80 (s, 1H), 4.83 (s, 1.2H), 4.72 (s, 0.8H), 4.46 (s, 0.8H), 4.28 (s, 1.2H), 4.22 (t, 1.2H), 4.06 (t, 0.8H), 3.99 (t, 1.2H), 3.87 (t, 0.8H).

Example 61

1-(Benzothiazole-2-sulfonyl)-4-{[6-N-(benzyloxycarbonyl)-adenine-9-yl]-acetyl}-piperazin-2-one The title compound was synthesized by the reaction of 1-(benzothiazole-2-sulfonyl)-piperazin-2-one trifluoroacetic acid salt with [6-N-(benzyloxycarbonyl)-adenine-9-yl]-acetic acid as per the procedure of Example 52. $^1$H-NMR (500 MHz; DMSO-$d_6$) δ 10.81 (brs, 1H), 8.60 (d, 1H), 8.36 (m, 1H), 8.28 (m, 2H), 7.73 (m, 2H), 7.46 (d, 2H), 7.40 (t, 2H), 7.34 (t, 1H), 5.41 (s, 1.2H), 5.29 (s, 0.8H), 5.23 (s, 2H), 4.57 (s, 0.8H), 4.28 (s, 2.4H), 4.09 (m, 2.0H), 3.88 (t, 0.8H).

Example 62

1-(Benzothiazole-2-sulfonyl)-4-{[6-N-(benzhydryloxycarbonyl)-adenine-9-yl]-acetyl}-piperazin-2-one The title compound was synthesized by the reaction of 1-(benzothiazole-2-sulfonyl)-piperazin-2-one trifluoroacetic acid salt with [6-N-(benzhydryloxycarbonyl)-adenine-9-yl]-acetic acid as per the procedure of Example 52. $^1$H NMR (500 MHz; DMSO-$d_6$) δ 11.15 (brs, 1H), 8.60 (d, 1H), 8.45~8.32 (m, 2H), 8.26 (m, 1H), 7.72 (m, 2H), 7.52 (d, 4H), 7.38 (t, 4H), 7.29 (t, 2H), 6.83 (s, 1H), 5.41 (s, 1.2H), 5.30 (s, 0.8H), 4.57 (s, 0.8H), 4.28 (s, 2.4H), 4.09 (brs, 2.0H), 3.88 (t, 0.8H).

Example 63

1-(Benzothiazole-2-sulfonyl)-4-{[6-N-(4-methoxybenzyloxycarbonyl)-adenin-9-yl]-acetyl}-piperazin-2-one The title compound was synthesized by the reaction of 1-(benzothiazole-2-sulfonyl)-piperazin-2-one trifluoroacetic acid salt with [6-N-(4-methoxybenzyloxycarbonyl)-adenine-9-yl]-acetic acid as per the procedure of Example 52. $^1$H NMR (500 MHz; DMSO-$d_6$) δ 10.60 (bs, 1H), 8.59 (d, 1H), 8.34 (m, 2H), 8.27 (m, 1H), 7.72 (m, 2H), 7.38 (d, 2H), 6.94 (d, 2H), 5.40 (s, 1.2H), 5.28 (s, 0.8H), 5.14 (s, 2H), 4.56 (s, 0.8H), 4.28 (m, 2.4H), 4.09 (t, 2H), 3.87 (t, 0.8H), 3.75 (s, 3H).

Example 64

1-(Benzothiazole-2-sulfonyl)-4-{[6-N-(3,4-dimethoxybenzyloxycarbonyl)-adenin-9-yl]-acetyl}-piperazin-2-one The title compound was synthesized by the reaction of 1-(benzothiazole-2-sulfonyl)-piperazin-2-one trifluoroacetic acid salt with [6-N-(3,4-dimethoxybenzyloxycarbonyl)-adenine-9-yl]-acetic acid as per the procedure of Example 52. $^1$H NMR (500 MHz; DMSO-d$_6$) δ 10.58 (s, 1H), 8.58 (s, 0.6H), 8.56 (s, 0.4H), 8.35 (m, 1H), 8.30 (s, 0.4H), 8.27 (s, 0.6H), 8.26 (m, 1H), 7.73 (m, 2H), 7.07 (s, 1H), 6.98 (d, 1H), 6.94 (d, 1H), 5.38 (s, 1.2H), 5.27 (s, 0.8H), 5.12 (s, 2H), 4.56 (s, 0.8H), 4.28 (m, 2.4H), 4.09 (t, 2H), 3.87 (t, 0.8H), 3.76 (s, 3H), 3.74 (s, 3H).

Example 65

1-(Benzothiazole-2-sulfonyl)-4-{[6-N-(piperonyloxycarbonyl)-adenin-9-yl]-acetyl}-piperazin-2-one The title compound was synthesized by the reaction of 1-(benzothiazole-2-sulfonyl)-piperazin-2-one trifluoroacetic acid salt with [6-N-(piperonyloxycarbonyl)-adenine-9-yl]-acetic acid as per the procedure of Example 52. $^1$H NMR (500 MHz; DMSO-d$_6$) δ 10.64 (s, 1H), 8.58 (s, 0.6H), 8.57 (s, 0.4H), 8.34 (m, 1H), 8.31 (s, 0.4H), 8.28 (s, 0.6H), 8.27 (m, 1H), 7.72 (m, 2H), 7.04 (s, 1H), 6.94 (d, 1H), 6.90 (d, 1H), 6.01 (s, 2H), 5.39 (s, 1.2H), 5.28 (s, 0.8H), 5.09 (s, 2H), 4.57 (s, 0.8H), 4.29 (m, 2.4H), 4.09 (t, 2H), 3.88 (t, 0.8H).

Example 66

1-(Benzothiazole-2-sulfonyl)-4-{[6-N-(2-methylthioethoxycarbonyl)-adenine-9-yl]acetyl}-piperazin-2-one The title compound was synthesized by the reaction of 1-(benzothiazole-2-sulfonyl)-piperazin-2-one trifluoroacetic acid salt with [6-N-(2-methylthioethoxycarbonyl)-adenine-9-yl]-acetic acid as per the procedure of Example 52. $^1$H NMR (500 MHz; DMSO-d$_6$) δ 10.80 (brs, 1H), 8.61 (d, 1H), 8.42 (s, 0.6H), 8.39 (s, 0.4H), 8.35 (m, 1H), 8.27 (m, 1H), 7.73 (m, 2H), 5.42 (s, 1.2H), 5.30 (s, 0.8H), 4.57 (s, 0.8H), 4.34-4.25 (m, 4.4H), 4.09 (m, 2.0H), 3.88 (t, 0.8H), 2.79 (t, 2H), 2.13 (s, 3H).

Example 67

1-(Benzothiazole-2-sulfonyl)-4-{[2-N-(benzyloxycarbonyl)-guanin-9-yl]-acetyl}-piperazin-2-one The title compound was synthesized by the reaction of 1-(benzothiazole-2-sulfonyl)-piperazin-2-one trifluoroacetic acid salt with [2-N-(benzyloxycarbonyl)-guanin-9-yl]-acetic acid as per the procedure of Example 52. $^1$H NMR (500 MHz; DMSO-d$_6$) δ 11.35 (bs, 2H), 8.34 (m, 1H), 8.25 (m, 1H), 7.81 (s, 0.6H), 7.77 (s, 0.4H), 7.71 (m, 2H), 7.45~7.30 (m, 5H), 5.23 (s, 2H), 5.13 (s, 1.2H), 5.02 (s, 0.8H), 4.51 (s, 0.8H), 4.27 (s, 1.2H), 4.24 (t, 1.2H), 4.08 (t, 0.8H), 4.03 (t, 1.2H), 3.85 (t, 0.8H).

Example 68

1-(Benzothiazole-2-sulfonyl)-4-{[2-N-(benzhydryloxycarbonyl)-guanin-9-yl]-acetyl}-piperazin-2-one The title compound was synthesized by the reaction of 1-(benzothiazole-2-sulfonyl)-piperazin-2-one trifluoroacetic acid salt with [2-N-(benzhydryloxycarbonyl)-guanin-9-yl]-acetic acid as per the procedure of Example 52. $^1$H NMR (500 MHz; DMSO-d$_6$) δ 11.62 (bs, H), 11.24 (bs, 1H), 8.36 (m, 1H), 8.26 (m, 1H), 7.81 (s, 0.6H), 7.77 (s, 0.4H), 7.72 (m, 2H), 7.45 (d, 4H), 7.38 (t, 4H), 7.30 (t, 2H), 6.86 (s, 1H), 5.16 (s, 1.2H), 5.05 (s, 0.8H), 4.53 (s, 0.8H), 4.28 (s, 1.2H), 4.26 (t, 1.2H), 4.09 (t, 0.8H), 4.05 (t, 1.2H), 3.86 (t, 0.8H).

Example 69

1-(Benzothiazole-2-sulfonyl)-4-{[2-N-(4-methoxybenzyloxycarbonyl)-guanin-9-yl]-acetyl}-piperazin-2-one The title compound was synthesized by the reaction of 1-(benzothiazole-2-sulfonyl)-piperazin-2-one trifluoroacetic acid salt with [2-N-(4-methoxybenzyloxycarbonyl)-guanin-9-yl]-acetic acid as per the procedure of Example 52. $^1$H NMR (500 MHz; DMSO-d$_6$) δ 11.38 (bs, 2H), 8.33 (m, 1H), 8.24 (m, 1H), 7.81 (d, 0.6H), 7.77 (d, 0.4H), 7.71 (m, 2H), 7.36 (d, 2H), 6.94 (d, 2H), 5.16 (s, 2H), 5.12 (s, 1.2H), 5.02 (s, 0.8H), 4.51 (s, 0.8H), 4.26 (s, 1.2H), 4.24 (t, 1.2H), 4.08 (t, 0.8H), 4.03 (t, 1.2H), 3.85 (t, 0.8H), 3.75 (s, 3H).

Example 70

1-(Benzothiazole-2-sulfonyl)-4-{[2-N-(3,4-dimethoxybenzyloxycarbonyl)-guanin-9-yl]-acetyl}-piperazin-2-one The title compound was synthesized by the reaction of 1-(benzothiazole-2-sulfonyl)-piperazin-2-one trifluoroacetic acid salt with [2-N-(3,4-dimethoxybenzyloxycarbonyl)-guanin-9-yl]-acetic acid as per the procedure of Example 52.1H NMR (500 MHz; DMSO-d$_6$) δ 11.41 (s, 1H), 11.37 (s, 1H), 8.34 (m, 1H), 8.24 (m, 1H), 7.81 (s, 0.6H), 7.77 (s, 0.4H), 7.71 (m, 2H), 7.04 (s, 1H), 6.95 (d, 1H), 6.94 (d, 1H), 5.15 (s, 2H), 5.13 (s, 1.2H), 5.02 (s, 0.8H), 4.51 (s, 0.8H), 4.27 (s, 1.2H), 4.24 (t, 1.2H), 4.07 (t, 0.8H), 4.03 (t, 1.2H), 3.84 (t, 0.8H), 3.75 (s, 3H), 3.74 (s, 3H).

Example 71

1-(Benzothiazole-2-sulfonyl)-4-{[2-N-(piperonyloxycarbonyl)-guanin-9-yl]-acetyl}-piperazin-2-one The title compound was synthesized by the reaction of 1-(benzothiazole-2-sulfonyl)-piperazin-2-one trifluoroacetic acid salt with [2-N-(piperonyloxycarbonyl)-guanin-9-yl]-acetic acid as per the procedure of Example 52. $^1$H NMR (500 MHz; DMSO-d$_6$) δ 11.40 (brs, 2H), 8.36 (m, 1H), 8.27 (m, 1H), 7.84 (s, 0.6H), 7.78 (s, 0.4H), 7.73 (m, 2H), 7.02 (s, 1H), 6.93 (s, 2H), 6.04 (s, 2H), 5.15 (m, 3.2H), 5.05 (s, 0.8H), 4.55 (s, 0.8H), 4.30 (s, 1.2H), 4.27 (t, 1.2H), 4.11 (t, 0.8H), 4.07 (t, 1.2H), 3.88 (t, 0.8H).

Example 72

1-(Benzothiazole-2-sulfonyl)-4-{[2-N-(2-methylthioethoxycarbonyl)-guanin-9-yl]-acetyl}-piperazin-2-one The title compound was synthesized by the reaction of 1-(benzothiazole-2-sulfonyl)-piperazin-2-one trifluoroacetic acid salt with [2-N-(2-methylthioethoxycarbonyl)-guanin-9-yl]-acetic acid as per the procedure of Example 52. $^1$H NMR (500 MHz; DMSO-$d_6$) δ 11.41 (brs, 1H), 11.35 (brs, 1H), 8.35 (m, 1H), 8.25 (m, 1H), 7.82 (d, 0.6H), 7.78 (d, 0.4H), 7.72 (m, 2H), 5.14 (s, 1.2H), 5.03 (s, 0.8H), 4.51 (s, 0.8H), 4.32 (t, 2H), 4.27 (s, 1.2H), 4.24 (t, 1.2H), 4.08 (t, 0.8H), 4.04 (t, 1.2H), 3.85 (t, 0.8H), 2.75 (t, 2H), 2.12 (s, 3H).

Example 73

1-(5-Chloro-benzothiazole-2-sulfonyl)-4-{[2-N-(benzhydryloxycarbonyl)-guanin-9-yl]-acetyl}-piperazin-2-one The title compound was synthesized by the reaction of 1-(5-chloro-benzothiazole-2-sulfonyl)-piperazin-2-one trifluoroacetic acid salt with [2-N-(benzhydryloxycarbonyl)-guanin-9-yl]-acetic acid as per the procedure of Example 52. $^1$H NMR (500 MHz; DMSO-$d_6$) δ 11.62 (brs, H), 11.25 (brs, 1H), 8.42-8.39 (m, 1H), 7.96 (s, 0.6H), 7.82 (s, 0.4H), 7.78 (m, 1H), 7.46 (d, 4H), 7.39 (t, 4H), 7.31 (t, 2H), 6.87 (s, 1H), 5.17 (s, 1.2H), 5.06 (s, 0.8H), 4.53 (s, 0.8H), 4.29 (s, 1.2H), 4.25 (t, 1.2H), 4.08-4.06 (m, 2H), 3.87 (t, 0.8H).

Example 74

1-(Benzothiazole-2-sulfonyl)-4-[thymin-1-yl]-acetyl-3-methyl-piperazin-2-one

The title compound was synthesized by the reaction of 1-(benzothiazole-2-sulfonyl)-3-methyl-piperazin-2-one trifluoroacetic acid salt with (thymin-1-yl)-acetic acid as per the procedure of Example 52. $^1$H NMR (500 MHz; DMSO-$d_6$) δ 11.31 (brs, 1H), 8.34 (m, 1H), 8.25 (m, 1H), 7.72 (m, 2H), 7.36 (s, 1H), 4.85~4.60 (m, 2.5H), 4.55~4.40 (m, 0.5H), 4.25~4.10 (m, 2.5H), 3.85~3.74 (m, 0.5H), 3.50~3.30 (m, 1H), 1.75 (s, 3H), 1.44 (d, 1H), 1.29 (d. 2H).

Example 75

1-(Benzothiazole-2-sulfonyl)-4-[(thymin-1-yl)-acetyl]-piperazin-2-one

Method A
To a solution of N-[2-(benzothiazole-2-sulfonylamino)-ethyl]-N-[(thymin-1-yl)-acetyl]-glycine (963 mg, 2 mmole) in tetrahydrofuran (50 mL) was added N-methyl morpholine (3.3 mL, 3 mmole) and then the mixture was cooled to −20° C. After stirring for 5 min at the same temperature, chloroisobutylformate (3.4 mL, 26 mmole) was added to the reaction mixture. The resulting mixture was slowly warmed to 0° C. for 1 h. Then the reaction mixture was evaporated in vacuo and dissolved in a mixture of ethyl acetate and acetonitrile. The solution was washed with brine and dried over sodium sulfate and filtered. The filtrate was evaporated in vacuo and triturated with TETRAHYDROFURAN-ethyl ether (1/1, v/v) to precipitate solid. The solid was filtered off, washed with ethyl ether, and dried in vacuo to give the titled compound (834 mg, 90%).

Method B
The mixture of N-[2-(benzothiazole-2-sulfonylamino)-ethyl]-N-[(thymin-1-yl)-acetyl]-glycine (963 mg, 2 mmol) and EDC (460 mg, 2.4 mmol) in DMF (10 mL) was stirred for 6 h at room temperature. The solvent was removed by evaporation in vacuo and the residue was dissolved in dichloromethane (30 mL). The solution was washed with 1N HCl solution (20 mL) and water (30 mL). The organic layer was dried over MgSO$_4$, filtered, and concentrated to give a yellow residue. The residue was dissolved in acetone and passed on a short silica gel. The filtrate was evaporated and the residue was dissolved in tetrahydrofuran. The organic solution was slowly added to ethyl ether to precipitate a white solid, which was collected by filtration, washed with tetrahydrofuran/ethyl ether (1/2, v/v) and then dried to give the titled compound (862 mg, 93%). $^1$H NMR (500 MHz; DMSO-$d_6$) data are the same as Example 52.

Example 76

1-(Benzothiazole-2-sulfonyl)-4-{[4-N-(benzhydryloxycarbonyl)-cytosin-1-yl]acetyl}-piperazin-2-one The title compound was synthesized from N-[2-benzothiazole-2-sulfonylamino)-ethyl]-N-{[4-N-(benzhydryloxycarbonyl)]-cytosin-1-yl}-acetyl}-glycine as per the procedures of method A or B of Example 75. Yield: method A (87%), method B (92%). $^1$H NMR (500 MHz; DMSO-$d_6$) data are the same as Example 55.

Example 77

1-(Benzothiazole-2-sulfonyl)-4-{[4-N-(4-methoxybenzyloxycarbonyl)-cytosin-1-yl]acetyl}-piperazin-2-one The title compound was synthesized from N-[2-(benzothiazole-2-sulfonylamino)-ethyl]-N-{[4-N-(4-methoxybenzyloxycarbonyl)]-cytosin-1-yl}-acetyl}-glycine as per the procedures of method A or B of Example 75. Yield: method A (85%), method B (90%). $^1$H NMR (500 MHz; DMSO-$d_6$) data are the same as Example 56.

Example 78

1-(Benzothiazole-2-sulfonyl)-4-{[4-N-(3,4-dimethoxybenzyloxycarbonyl)-cytosin-1-yl]acetyl}-piperazin-2-one The title compound was synthesized from N-[2-(benzothiazole-2-sulfonylamino)-ethyl]-N-{[4-N-(3,4-dimethoxybenzyloxycarbonyl)]-cytosin-1-yl}-acetyl}-glycine as per the procedures of method A or B of Example 75. Yield: method A (85%), method B (90%). $^1$H NMR (500 MHz; DMSO-$d_6$) data are the same as Example 57.

Example 79

1-(Benzothiazole-2-sulfonyl)-4-{[4-N-(piperonyloxycarbonyl)-cytosin-1-yl]acetyl}-piperazin-2-one The title compound was synthesized from N-[2-(benzothiazole-2-sulfonylamino)-ethyl]-N-{[4-N-(piperonyloxycarbonyl)]-cytosin-1-yl}-acetyl}-glycine as per the procedures of method A or B of Example 75. Yield: method A (91%), method B (95%). $^1$H NMR (500 MHz; DMSO-$d_6$) data are the same as Example 58.

Example 80

1-(Benzothiazole-2-sulfonyl)-4-{[4-N-(2-methylthioethoxycarbonyl)-cytosin-1-yl]acetyl}-piperazin-2-one The title compound was synthesized from N-[2-(benzothiazole-2-sulfonylamino)-ethyl]-N-{[4-N-(2-methylthioethoxycarbonyl)]-cytosin-1-yl}-acetyl}-glycine as per the procedures of method A or B of Example 75. Yield: method A (90%), method B (93%). $^1$H NMR (500 MHz; DMSO-$d_6$) data are the same as Example 59.

Example 81

1-(Benzothiazole-2-sulfonyl)-4-{[6-N-(benzhydryloxycarbonyl)-adenin-9-yl]-acetyl}-piperazin-2-one The title compound was synthesized from N-[2-(benzothiazole-2-sulfonylamino)-ethyl]-N-{[6-N-(benzhydryloxycarbonyl)]-adenin-9-yl}-acetyl}-glycine as per the procedures of method A or B of Example 75. Yield: method A (89%), method B (94%). $^1$H NMR (500 MHz; DMSO-$d_6$) data are the same as Example 62.

Example 82

1-(Benzothiazole-2-sulfonyl)-4-{[6-N-(4-methoxybenzyloxycarbonyl)-adenin-9-yl]-acetyl}-piperazin-2-one The title compound was synthesized from N-[2-(benzothiazole-2-sulfonylamino)-ethyl]-N-{[6-N-(4-methoxybenzyloxycarbonyl)]-adenin-9-yl}-acetyl}-glycine as per the procedures of method A or B of Example 75. Yield: method A (89%), method B (94%). $^1$H NMR (500 MHz; DMSO-$d_6$) data are the same as Example 63.

Example 83

1-(Benzothiazole-2-sulfonyl)-4-{[6-N-(3,4-dimethoxybenzyloxycarbonyl)-adenin-9-yl]-acetyl}-piperazin-2-one The title compound was synthesized from N-[2-(benzothiazole-2-sulfonylamino)-ethyl]-N-{[6-N-(3,4-dimethoxybenzyloxycarbonyl)]-adenin-9-yl}-acetyl}-glycine as per the procedures of method A or B of Example 75. Yield: method A (84%), method B (89%). $^1$H NMR (500 MHz; DMSO-$d_6$) data are the same as Example 64.

Example 84

1-(Benzothiazole-2-sulfonyl)-4-{[6-N-(piperonyloxycarbonyl)-adenin-9-yl]-acetyl}-piperazin-2-one The title compound was synthesized from N-[2-(benzothiazole-2-sulfonylamino)-ethyl]-N-{[6-N-(piperonyloxycarbonyl)]-adenin-9-yl}-acetyl}-glycine as per the procedures of method A or B of Example 75. Yield: method A (80%), method B (88%). $^1$H NMR (500 MHz; DMSO-$d_6$) data are the same as Example 65.

Example 85

1-(Benzothiazole-2-sulfonyl)-4-{[6-N-(2-methylthioethoxycarbonyl)-adenin-9-yl]-acetyl}-piperazin-2-one The title compound was synthesized from N-[2-(benzothiazole-2-sulfonylamino)-ethyl]-N-{[6-N-(2-methylthioethoxycarbonyl)]-adenin-9-yl}-acetyl}-glycine as per the procedures of method A or B of Example 75. Yield: method A (88%), method B (93%). $^1$H NMR (500 MHz; DMSO-$d_6$) data are the same as Example 66.

Example 86

1-(Benzothiazole-2-sulfonyl)-4-{[2-N-(benzhydryloxycarbonyl)-guanin-9-yl]acetyl}-piperazin-2-one The title compound was synthesized from N-[2-(benzothiazole-2-sulfonylamino)-ethyl]-N-{[2-N-(benzhydryloxycarbonyl)]-guanin-9-yl}-acetyl}-glycine as per the procedures of method A or B of Example 75. Yield: method A (90%), method B (92%). $^1$H NMR (500 MHz; DMSO-$d_6$) data are the same as Example 68.

Example 87

1-(Benzothiazole-2-sulfonyl)-4-{[2-N-(4-methoxybenzyloxycarbonyl)-guanin-9-yl]acetyl}-piperazin-2-one The title compound was synthesized from N-[2-(benzothiazole-2-sulfonylamino)-ethyl]-N-{[2-N-(4-methoxybenzyloxycarbonyl)]-guanin-9-yl}-acetyl}-glycine as per the procedures of method A or B of Example 75. Yield: method A (86%), method B (88%). $^1$H NMR (500 MHz; DMSO-$d_6$) data are the same as Example 69.

Example 88

1-(Benzothiazole-2-sulfonyl)-4-{[2-N-(3,4-dimethoxybenzyloxycarbonyl)-guanin-9-yl]acetyl}-piperazin-2-one The title compound was synthesized from N-[2-(benzothiazole-2-sulfonylamino)-ethyl]-N-{[2-N-(3,4-dimethoxybenzyloxycarbonyl)]-guanin-9-yl}-acetyl}-glycine as per the procedures of method A or B of Example 75. Yield: method A (83%), method B (86%). $^1$H NMR (500 MHz; DMSO-$d_6$) data are the same as Example 70.

Example 89

1-(Benzothiazole-2-sulfonyl)-4-{[2-N-(piperonyloxycarbonyl)-guanin-9-yl]acetyl}-piperazin-2-one The title compound was synthesized from N-[2-(benzothiazole-2-sulfonylamino)-ethyl]-N-{[2-N-(piperonyloxycarbonyl)]-guanin-9-yl}-acetyl}-glycine as per the procedures of method A or B of Example 75. Yield: method A (92%), method B (95%). $^1$H NMR (500 MHz; DMSO-$d_6$) data are the same as Example 71.

Example 90

1-(Benzothiazole-2-sulfonyl)-4-{[2-N-(2-methylth-ioethoxycarbonyl)-guanin-9-yl]acetyl}-piperazin-2-one The title compound was synthesized from N-[2-(benzothiazole-2-sulfonylamino)-ethyl]-N-{[2-N-(2-methylthio-ethoxycarbonyl)]-guanin-9-yl}-acetyl}-glycine as per the procedures of method A or B of Example 75. Yield: method A (86%), method B (88%). $^1$H NMR (500 MHz; DMSO-$d_6$) data are the same as Example 72.

Example 91

1-(Benzothiazole-2-sulfonyl)-4-[thymin-1-yl]-acetyl-3-methyl-piperazin-2-one

The title compound was synthesized by the reaction of 1-(benzothiazole-2-sulfonyl)-piperazin-2-one trifluoroacetic acid salt with (thymin-1-yl)-acetic acid as per the procedure of Example 75. Yield: method A (83%), method B (87%). $^1$H NMR (500 MHz; DMSO-$d_6$) data are the same as Example 74.

Solid phase Synthesis of PNA Oligomer
General Procedure

PNA oligomer synthesis was conducted manually on a Nova Syn TG amino resin (Nova biochem., 0.26 mmol/g loading) which is a PEG-grafted polystyrene resin with amine functionality. The resin was coupled with PAL linker (5-[4-(9-fluorenylmethoxycarbonyl)amino-3,5-dimethox-yphenoxy]pentanoic acid (Advanced ChemTech) by using HBTU as a coupling reagent in DMF. The resulting resin was treated with 20% piperidine in DMF to activate the amine functional group of PAL linker for PNA oligomer synthesis. The PNA oligomer was synthesized according to the following synthesis cycle. All reactions and washes of the resin were performed in a fritted vial.

Following is a non-limiting general procedure for solid phase synthesis of PNA oligomer:

1. Coupling with 10 equiv. of appropriate monomer (20 M in 0.5M acetic acid in DMF) for 2 h.
2. Washing with DMF 3 times.
3. Capping with acetic anhydride (5% acetic anhydride and 6% lutidine in DMF) for 5 min.
4. Washing with DMF 2 times.
5. Cleavage over-reacted acetyl group in sulfonamide with piperidine (1.0 M in DMF) for 5 min.
6. Washing with DMF 3 times.
7. Deprotection of benzothiazole-2-sulfonyl group with 4-methoxybenzenethiol for 15 min.
8. Washing with DMF 3 times After removal of the final benzothiazole-2-sulfonyl group, the resin is washed with DMF 3 times and dichloromethane 2 times and dried. The removal the protecting group of exocyclic amine and cleavage from the resin was performed in one step by treatment with 25% m-cresol in TFA for 1.5 h. The resin is filtered off and washed with TFA. Almost TFA of the combined filtrate is removed by blowing a steady stream of nitrogen. Then the residue was suspended with ethyl ether and centrifuged. The supernatant is carefully decanted off. The residue of crude PNA oligomer is washed one more time by suspension with ethyl ether, centrifuge, and removal of supernatant. The crude PNA oligomer is analyzed with HPLC and confirmed by Matrix Assisted Laser Desorption-Time of Flight (MALDI-TOF).

Example 92

Synthesis of PNA Oligomer Sequence
H$_2$N-CTCGTTTCCA-H (SEQ ID NO: 1)

Figure 17:
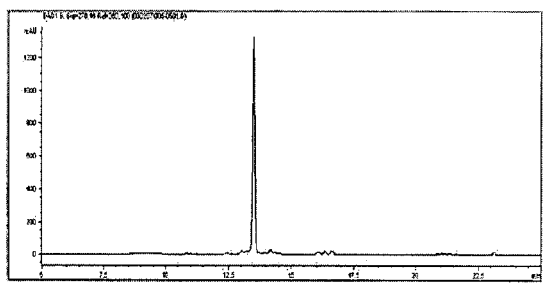
FIG. 17 shows HPLC and MALDI-TOF results for synthesized oligomer SEQ ID NO: 1
Figure 17:
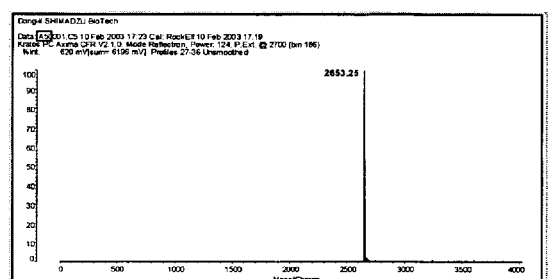

The title sequence was synthesized manually by the above general procedure using monomer of general formula I, wherein R1, R2, R3, R4, and R5 are H and the protecting group of exocyclic amine of nucleobases (A, C, and G) is benzhydryloxycarbonyl. FIGS. 17A-B show (A) HPLC and (B) MALDI-TOF profiles.

Example 93

Synthesis of PNA Oligomer Sequence
H$_2$N-TCGTGTCGTA-H (SEQ ID NO:2)

Figure 18:
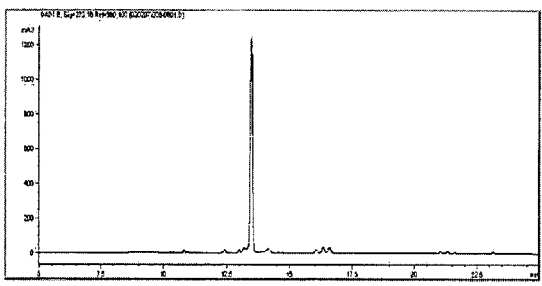
FIG. 18 shows HPLC and MALDI-TOF results for synthesized oligomer SEQ ID NO: 2
Figure 18:
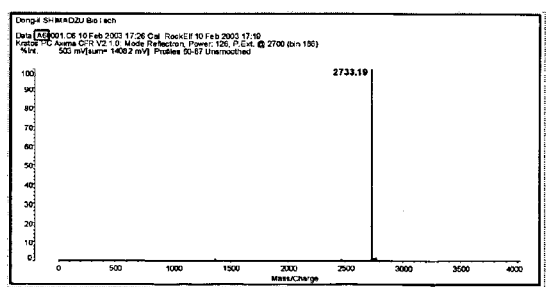

The title sequence was synthesized manually by the above general procedure using monomer of general formula I, wherein R1, R2, R3, R4, and R5 are H and the protecting group of exocyclic amine of nucleobases (A, C, and G) is benzhydryloxycarbonyl. FIGS. 18A-B show (A) HPLC and (B) MALDI-TOF profiles.

Example 94

Synthesis of PNA Oligomer Sequence
H$_2$N-ACCAGCGGCA-H (SEQ ID NO:3)

Figure 19:
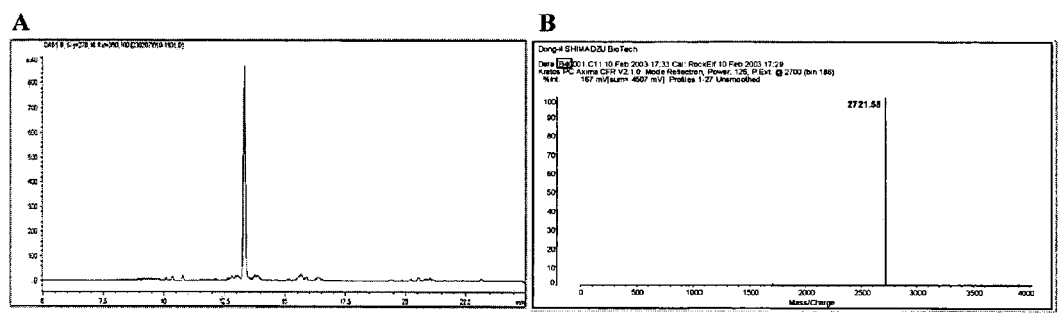
FIG. 19 shows HPLC and MALDI-TOF results for synthesized oligomer SEQ ID NO: 3

The title sequence was synthesized manually by the above general procedure using monomer of general formula I, wherein R1, R2, R3, R4, and R5 are H and the protecting group of exocyclic amine of nucleobases (A, C, and G) is benzhydryloxycarbonyl. FIGS. 19A-B show (A) HPLC and (B) MALDI-TOF profiles.

Example 95

Synthesis of PNA Oligomer Sequence
H$_2$N-TCTTCTAGTG-H (SEQ ID NO:4)

Figure 20:
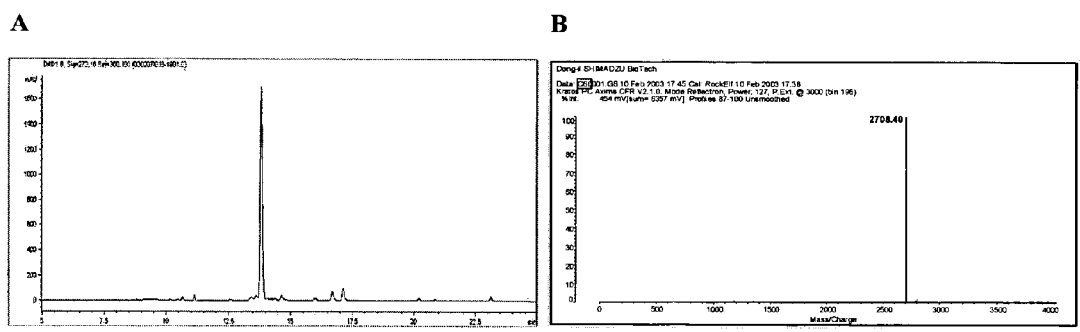
FIG. 20 shows HPLC and MALDI-TOF results for synthesized oligomer SEQ ID NO: 4

The title sequence was synthesized manually by the above general procedure using monomer of general formula I, wherein R1, R2, R3, R4, and R5 are H and the protecting group of exocyclic amine of nucleobases (A, C, and G) is benzhydryloxycarbonyl. FIGS. 20A-B show (A) HPLC and (B) MALDI-TOF profiles.

Example 96

Synthesis of PNA Oligomer Sequence
H$_2$N-GTGCTCCTCC-H (SEQ ID NO:5)

Figure 21:
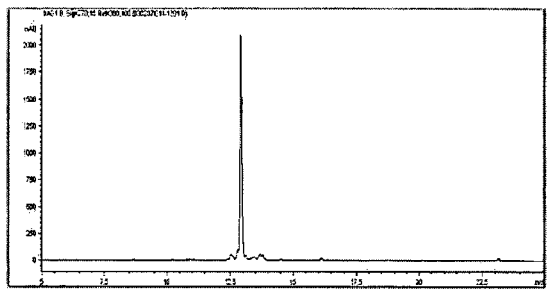
FIG. 21 shows HPLC and MALDI-TOF results for synthesized oligomer SEQ ID NO: 5
Figure 21:
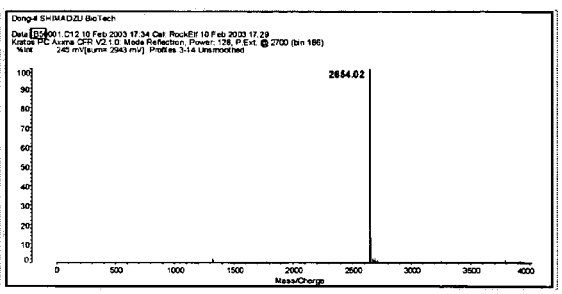

The title sequence was synthesized manually by the above general procedure using monomer of general formula I, wherein R1, R2, R3, R4, and R5 are H and the protecting group of exocyclic amine of nucleobases (C and G) is benzhydryloxycarbonyl. FIGS. 21A-B show (A) HPLC and (B) MALDI-TOF profiles.

Example 97

Synthesis of PNA Oligomer Sequence
H$_2$N-GTGCATGATG-H (SEQ ID NO:6)

Figure 22:
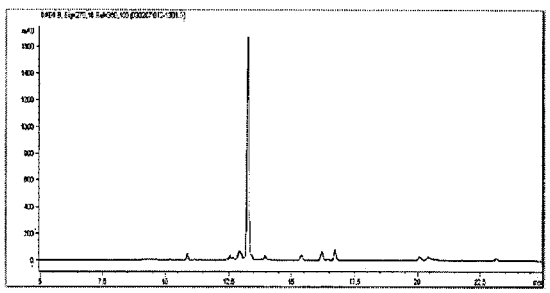
FIG. 22 shows HPLC and MALDI-TOF results for synthesized oligomer SEQ ID NO: 6
Figure 22:
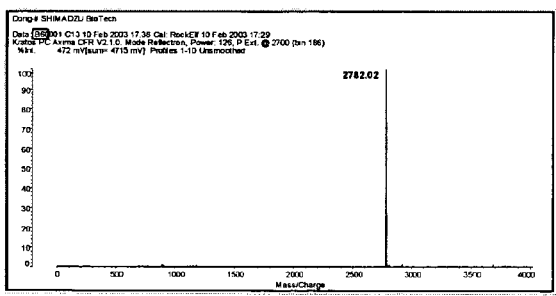

The title sequence was synthesized manually by the above general procedure using monomer of general formula I, wherein R1, R2, R3, R4, and R5 are H and the protecting group of exocyclic amine of nucleobases (A, C, and G) is benzhydryloxycarbonyl. FIGS. 22A-B show (A) HPLC and (B) MALDI-TOF profiles.

Example 98

Synthesis of PNA Oligomer Sequence
H$_2$N-CCCTACTGTG-H (SEQ ID NO:7)

Figure 23:
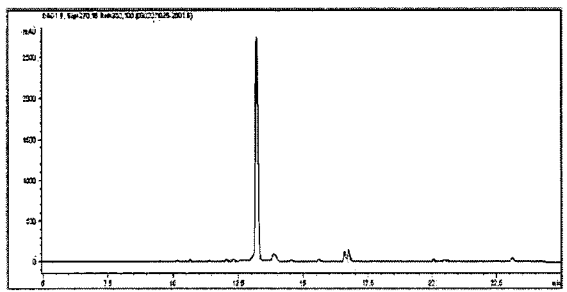
FIG. 23 shows HPLC and MALDI-TOF results for synthesized oligomer SEQ ID NO: 7
Figure 23:
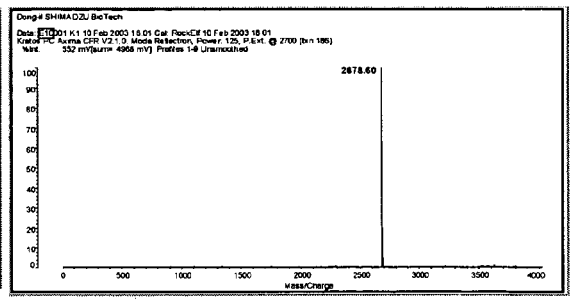

The title sequence was synthesized manually by the above general procedure using monomer of general formula I, wherein R1, R2, R3, R4, and R5 are H and the protecting group of exocyclic amine of nucleobases (A, C, and G) is benzhydryloxycarbonyl. FIGS. 23A-B show (A) HPLC and (B) MALDI-TOF profiles.

Example 99

Synthesis of PNA oligomer sequence
H$_2$N-CTCATTTCCA-H (SEQ ID NO:8)

Figure 24:
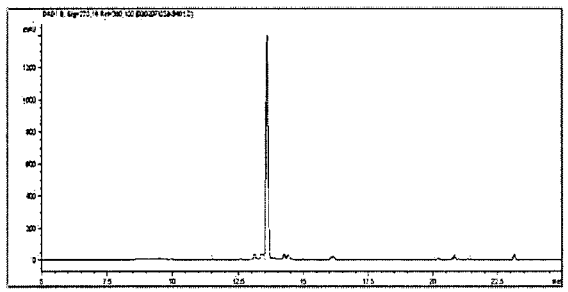
FIG. 24 shows HPLC and MALDI-TOF results for synthesized oligomer SEQ ID NO: 8
Figure 24:
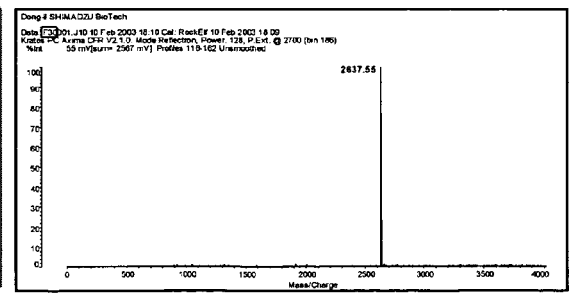

The title sequence was synthesized manually by the above general procedure using monomer of general formula I, wherein R1, R2, R3, R4, and R5 are H and the protecting group of exocyclic amine of nucleobases (A and C) is benzhydryloxycarbonyl. FIGS. 24A-B show (A) HPLC and (B) MALDI-TOF profiles.

Example 100

Synthesis of PNA Oligomer Sequence
H$_2$N-ACCCTACTGT-H (SEQ. ID NO:9)

Figure 25:
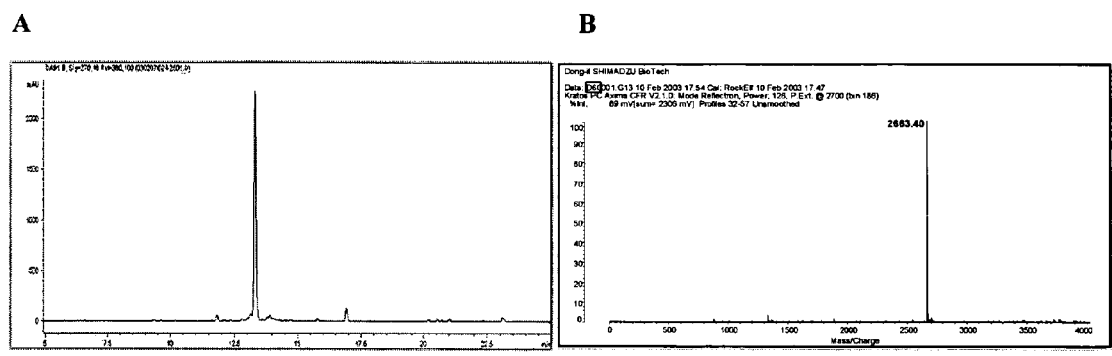
FIG. 25 shows HPLC and MALDI-TOF results for synthesized oligomer SEQ ID NO: 9

The title sequence was synthesized manually by the above general procedure using monomer of general formula I, wherein R1, R2, R3, R4, and R5 are H and the protecting group of exocyclic amine of nucleobases (A, C, and G) is benzhydryloxycarbonyl. FIGS. 25A-B show (A) HPLC and (B) MALDI-TOF profiles.

Those skilled in the art will recognize, or be able to ascertain using no more than routine experimentation, many equivalents to the specific embodiments of the invention specifically described herein. Such equivalents are intended to be encompassed in the scope of the claims.

---

What is claimed is:

1. A compound having formula I:

wherein
E is nitrogen or C—R'; J is sulfur or oxygen;
R', R1, R2, R3, R4 is independently H, halogen, alkyl, nitro, cyano, alkoxy, halogenated alkyl, halogenated alkoxy, phenyl or halogenated phenyl; and
R5 is H or protected or unprotected side chain of a naturally occurring α-amino acid.

2. The compound of claim 1, wherein E is nitrogen and J is sulfur.

3. The compound of claim 1, wherein E is nitrogen and J is oxygen.

4. The compound of claim 1, wherein E is CH and J is sulfur.

5. The compound of claim 1, wherein E is CH and J is oxygen.

6. The compound of claim 1, wherein R5 is H or unprotected side chain of a naturally occurring α-amino acid.

7. The compound of claim 1, wherein R' is H, $CF_3$, F, Cl, Br, I, methyl, phenyl, nitro, or nitrile.

8. The compound of claim 1, wherein R1, R2, R3, and R4 are H.

9. The compound of claim 1, wherein R2 is Cl, and R1, R3 and R4 are H.

10. The compound of claim 1, wherein R1 is Cl, R2 is methoxy, and R3, R4 and R5 are H.

11. The compound of claim 1, wherein R1, R2, R3, and R4 are H; E is nitrogen; and J is sulfur.

12. A method of making the compound of claim 1, comprising cyclizing a compound of formula VI in the presence of a coupling reagent that is customarily used in peptide synthesis or an anhydride, wherein the formula VI is represented as follows:

wherein

E is nitrogen or C—R'; J is sulfur or oxygen;

R', R1, R2, R3, R4 is independently H, halogen, alkyl, nitro, cyano, alkoxy, halogenated alkyl, halogenated alkoxy, phenyl or halogenated phenyl;

R5 is H, or a side chain of a naturally occurring α-amino acid, or a protected side chain of a naturally occurring α-amino acid.

13. A method of making the compound of claim 1, comprising coupling reaction of a compound of formula IV with a nucleobase acetic acid moiety in the presence of non-nucleophilic organic base and a coupling reagent that is customarily used in peptide synthesis, wherein said formula IV is represented as follows:

wherein

HX is an organic or inorganic acid;

E is nitrogen or C—R'; J is sulfur or oxygen;

R', R1, R2, R3, R4 is independently H, halogen, alkyl, nitro, cyano, alkoxy, halogenated alkyl, halogenated alkoxy, phenyl or halogenated phenyl; and R5 is H, or a side chain of a naturally occurring α-amino acid, or a protected side chain of a naturally occurring α-amino acid, wherein said nucleobase acetic acid moiety is represented as follows:

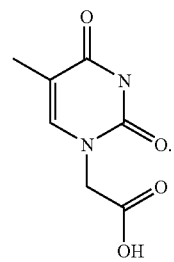

* * * * *